US009951340B2

(12) United States Patent
Lesser et al.

(10) Patent No.: US 9,951,340 B2
(45) Date of Patent: Apr. 24, 2018

(54) COMPOSITIONS AND METHODS FOR BACTERIAL DELIVERY OF POLYPEPTIDES

(71) Applicants: The General Hospital Corporation, Boston, MA (US); President and Fellows of Harvard College, Cambridge, MA (US)

(72) Inventors: Cammie Lesser, Cambridge, MA (US); Amy Jo Wagers, Cambridge, MA (US); Analise Z. Reeves, Brookline, MA (US)

(73) Assignees: The General Hospital Corporation, Cambridge, MA (US); President and Fellows of Harvard College, Boston, MA (US)

( * ) Notice: Subject to any disclaimer, the term of this patent is extended or adjusted under 35 U.S.C. 154(b) by 0 days.

(21) Appl. No.: 14/772,697

(22) PCT Filed: Mar. 6, 2014

(86) PCT No.: PCT/US2014/020972

§ 371 (c)(1),
(2) Date: Sep. 3, 2015

(87) PCT Pub. No.: WO2014/138324

PCT Pub. Date: Sep. 12, 2014

(65) Prior Publication Data

US 2016/0046951 A1 Feb. 18, 2016

Related U.S. Application Data

(60) Provisional application No. 61/774,282, filed on Mar. 7, 2013.

(51) Int. Cl.

| | |
|---|---|
| *C12N 15/70* | (2006.01) |
| *C12N 15/74* | (2006.01) |
| *A61K 35/74* | (2015.01) |
| *A61K 48/00* | (2006.01) |

(52) U.S. Cl.
CPC .............. *C12N 15/70* (2013.01); *A61K 35/74* (2013.01); *C12N 15/74* (2013.01); *A61K 48/00* (2013.01)

(58) Field of Classification Search
None
See application file for complete search history.

(56) References Cited

U.S. PATENT DOCUMENTS

| | | | | |
|---|---|---|---|---|
| 6,306,387 B1 * | 10/2001 | Galan | A61K 39/00 424/9.1 |
| 2010/0120124 A1 * | 5/2010 | Fernandez Herrero | C07K 16/00 435/252.3 |
| 2012/0021517 A1 * | 1/2012 | Jin | C07K 14/21 435/377 |
| 2015/0359909 A1 * | 12/2015 | O'Sullivan | A61K 49/0097 424/9.2 |

FOREIGN PATENT DOCUMENTS

| | | |
|---|---|---|
| JP | 2001/522605 A | 11/2001 |
| WO | 1998/053854 B1 | 12/1998 |
| WO | 1999/024576 A1 | 5/1999 |
| WO | 2012/012605 B2 | 1/2012 |

OTHER PUBLICATIONS

Singh et al ., LcrH, a Class II Chaperone from the Type Three Secretion System, Has a Highly Flexible Native Structure The Journal of Biological Chemistry vol. 288, No. 6, pp. 4048-4055, Feb. 8, 2013.*

Lee et al Review Molecular Mechanisms of Host Cytoskeletal Rearrangements by Shigella Invasins Int. J. Mol. Sci. 2014, 15, 18253-18266.*

Sha et al Further characterization of a type III secretion system (T3SS) and of a new effector protein from a clinical isolate of Aeromonas hydrophila—Part I ,Microbial Pathogenesis 43 (2007) 127-146.*

Eichelberg et al., Differential Regulation of *Salmonella typhimurium* Type III Secreted Proteins by Pathogenicity Island 1 (SPI-1)-Encoded Transcriptional Activators InvF and HilA Infection and Immunity 1999, p. 4099-4105.*

Nguyen et al Phylogenetic Analyses of the Constituents of Type III Protein Secretion Systems J. Mol. Microbiol. Biotechnol. (2000) 2(2): 125-144.*

(Continued)

*Primary Examiner* — Maria Leavitt
(74) *Attorney, Agent, or Firm* — Nixon Peabody LLP; David S. Resnick; Nicole D. Kling

(57) ABSTRACT

The methods and compositions described herein relate to the delivery of polypeptides to a target cell, e.g. by utilizing engineered non-pathogenic bacteria comprising a type three secretion system (T3SS) and T3SS-compatible substrates. In one aspect, described herein are non-pathogenic microbial cells that have been engineered to express both a functional type three secretion system (T3SS) and at least one polypeptide that is compatible with the T3SS. Due to the wide variety of polypeptides that can be delivered to a target eukaryotic cell using the compositions and systems described herein, a commensurately wide variety of applications is contemplated, e.g. therapeutics and reprogramming.

11 Claims, 1 Drawing Sheet

(56) References Cited

OTHER PUBLICATIONS

Galan et alMolecular and Functional Characterization of the *Salmonella* Invasion Gene invA: Homology of Inv A to Members of a New Protein Family, Journal of Bacteriology, Jul. 1992, p. 4338-4349.*
Carayol et al Tips and tricks about Shigella invasion of epithelial cells Current Opinion in Microbiology 2013, 16:32-37.*
O'Callaghan et al., A novel host-responsive sensor mediates virulence and type III secretion during Pseudomonas aeruginosa—host cell interactions Microbiology (2012), 158, 1057-1070.*
Hensel et al Genes encoding putative effector proteins of the type III secretion system of *Salmonella* pathogenicity island 2 are required for bacterial virulence and proliferation in macrophages Molecular Microbiology (1998) 30(1), 163-174.*
Hegazy et al., "Evaluations of *Salmonella enterica* Type III Secretion System Effector Proteins as Carriers for Heterologous Vaccine Antigens", Infection and Immunity, 1193-1202 (2012).
Juarez-Rodriguez et al., "Live Attenuated *Salmonella* Vaccines against *Mycobactyerium tuberculosis* with Antigen Delivery via the Type III Secretion System", Infection and Immunity, 798-814 (2012).
Wieser et al., "First multi-epitope subunit vaccine against extraintestinal pathogenic *Escherichia coli* delivered by a bacterial type-3 secretaion system (T3SS)", International Journal of Medical Microbiology, 302:10-18 (2012).
Maurelli et al., "Cloning of plasmid DNA Sequences Involved in Invasion of HeLa Cells by Shigella flexneri." Infection and Immunity 49(1):164-171 (1985).
Mirsky, Ethan, "Refactoring the *Salmonella* type III secretion system" Dissertation. University of California, San Francisco 2012 (60 pages).
Moest et al, "*Salmonella* T3SSs: successful mission of the secret (ion) agents." Current Opinion in Microbiology 16(1):38-44 (2013).
Reeves et al., "Engineering *Escherichia coli* into a Protein Delivery System for Mammalian Cells." ACS Synthetic Biology 4(5):644-654 (2015).
Buchrieser et al., "The virulence plasmid pWR100 and the repertoire of proteins secreted by the type III secretion apparatus of Shigella flexneri." Molecular Microbiology 38(4):760-771 (2000).
Paetzold et al., "Shigella flexneri phagosomal escape is independent of invasion." Infection and immunity 75(10):4826-4830 (2007).
Sansonetti et al., "Alterations in the pathogenicity of *Escherichia coli* K-12 after transfer of plasmid and chromosomal genes from Shigella flexneri." Infection and Immunity 39(3):1392-1402 (1983).
Wilson et al., "Cloning of a functional *Salmonella* SPI-1 type III secretion system and development of a method to create mutations and epitope fusions in the cloned genes." Journal of Biotechnology 122(2):147-160 (2006).
Botteaux et al., "MxiC is secreted by and controls the substrate specificity of the Shigella flexneri type III secretion apparatus." Molecular Microbiology 71(2):449-460 (2009).
Deane et al., "Molecular model of a type III secretion system needle: Implications for host-cell sensing." PNAS 103(33):12529-12533 (2006).
Kenjale et al., "The needle component of the type III secreton of Shigella regulates the activity of the secretion apparatus." Journal of Biological Chemistry 280(52):42929-42937 (2005).
Martinez-Argudo et al., "The Shigella T3SS needle transmits a signal for MxiC release, which controls secretion of effectors." Molecular Microbiology 78(6):1365-1378 (2010).
Veenendaal et al., , Andreas KJ, et al. "The type III secretion system needle tip complex mediates host cell sensing and translocon insertion." Molecular Microbiology 63(6):1719-1730 (2007).
Chamekh et al., "Delivery of biologically active anti-inflammatory cytokines IL-10 and IL-1ra in vivo by the Shigella type III secretion apparatus", J Immunol, 180(6):4292-8 (2008).
Costa et al., "A new means to identify type 3 secreted effectors: functionally interchangeable class IB chaperones recognize a conserved sequence", Mbio, 3(1):e00243-11 (2012).
Kuhlman et al., "Site-specific chromosomal integration of large synthetic constructs", Nucleic Acids Res, 38(6):e92 (2010).
Parsot , "*Shigella* spp. and enteroinvasive *Escherichia coli* pathogenicity factors." FEMS microbiology letters 252(1):11-18 (2005).
Schroeder et al., "Molecular pathogenesis of *Shigella* spp.: controlling host cell signaling, invasion, and death by type III secretion." Clinical microbiology reviews 21(1):134-156 (2008).
Widmaier et al., "Engineering the *Salmonella* type III secretion system to export spider silk monomers", Mol Syst Biol, 5:309 (2009).
Wilson et al., "Cloning and transfer of the *Salmonella* pathogenicity island 2 type III secretion system for studies of a range of gram-negative genera", Appl Environ Microbiol, 73(18):5911-8 (2007).

* cited by examiner

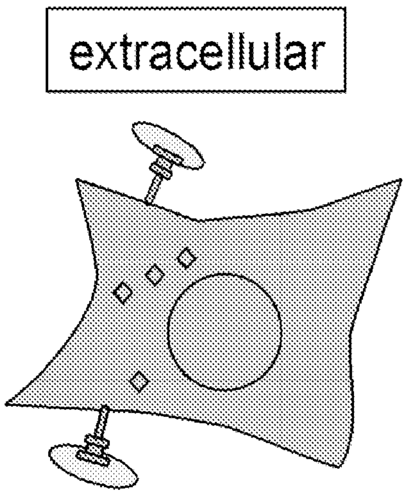
extracellular
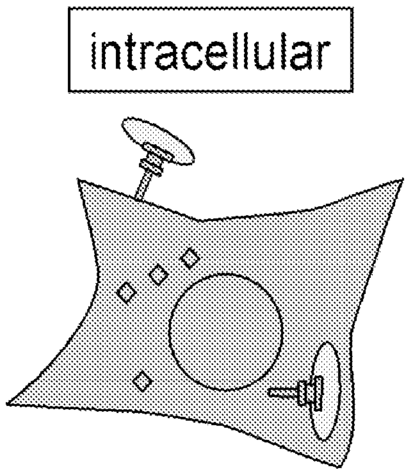
intracellular

COMPOSITIONS AND METHODS FOR BACTERIAL DELIVERY OF POLYPEPTIDES

CROSS-REFERENCE TO RELATED APPLICATIONS

This application is a 35 U.S.C. § 371 National Phase Entry Application of International Application No. PCT/US2014/020972 filed Mar. 6, 2014, which designates the U.S., and which claims benefit under 35 U.S.C. § 119(e) of U.S. Provisional Application No. 61/774,282 filed Mar. 7, 2013, the contents of which are incorporated herein by reference in their entirety.

GOVERNMENT SUPPORT

This invention was made with government support under Grant Nos. ROAGM094941, AI064285, DP2 OD004345, and DK036836 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 5, 2014, is named 030258-075551-PCT_SL.txt and is 201,687 bytes in size.

TECHNICAL FIELD

The technology described herein relates to delivery of polypeptides to target cells.

BACKGROUND

The introduction of exogenous proteins to cells can be accomplished by introduction of a transgene or the protein itself. Transgenic methods, while powerful, typically represent a permanent introduction of the exogenous material and the resulting alterations of the target cell's genome present complications, particularly in therapeutic contexts. Current methods of protein delivery are limited by labor-intensive purification processes, low protein yield and inefficient intracellular targeting, styming a number of technologies, ranging from therapeutic applications to the reprogramming of cells.

SUMMARY

The technology described herein is directed to compositions and methods for delivering polypeptides to a target cell. The novel methods of delivery are based at least in part upon the discovery that one can utilize non-pathogenic bacteria to deliver polypeptides to target cells if the bacteria are modified to comprise a type three secretion system (T3SS) and T3SS-compatible substrates.

In one aspect, described herein is an engineered non-pathogenic microbial cell comprising a first nucleic acid sequence comprising genes encoding a functional type three secretion system (T3SS), a second nucleic acid sequence encoding an T3SS-compatible polypeptide, wherein the engineered microbial cell is non-pathogenic with respect to the target cell or target organism. In some embodiments, the T3SS-compatible polypeptide is exogenous to the microbial cell. In some embodiments, the T3SS-compatible polypeptide is ectopic with respect to the target cell. In some embodiments, the cell comprises a third nucleic acid sequence encoding a master T3SS regulator. In some embodiments, the master T3SS regulator is selected from the group consisting of VirB and VirF. In some embodiments, the genes encoding a functional type three secretion system (T3SS) comprise: virB; acp; ipaA; ipaB; ipaC; ipaD; ipgC; ipgB1; ipgA; icsB; ipgD; ipgE; ipgF; mxiG; mxiH; mxiI; mxiJ; mxiK; mxiN; mxiL; mxiM; mxiE; mxiD; mxiC; mxiA; spa15; spa47; spa13; spa32; spa33; spa24; spa9; spa29; and spa40. In some embodiments, the type three secretion system (T3SS) comprises polypeptides endogenous to a bacterium selected from the group consisting of: *Shigella* spp; *Salmonella* spp; enteropathogenic *E. coli*; and *Yersinia* spp.

In some embodiments, the first nucleic acid sequence is located on a plasmid. In some embodiments, the first nucleic acid sequence is located on a chromosome. In some embodiments, the non-pathogenic organism is selected from the group consisting of *E. coli* NISSLE 1917 (EcN); *E. coli* K12; and derivative strains. In some embodiments, the strain which is derivative of *E. coli* K12 is selected from the group consisting of *E. coli* DH10β and *E. coli* DH5α. In some embodiments, the non-pathogenic organism is *E. coli* MinT3. In some embodiments, the non-pathogenic organism is engineered by deletion or mutation of one or more T3SS components. In some embodiments, the one or more T3SS components is selected from the group consisting of a toxin; a T3SS effector; a structural T3SS polypeptide; and a master regulator of T3SS components. In some embodiments, the T3SS component is located on a plasmid. Typically, if the bacteria are *E. coli*, the T3SS also comprises a master regulator.

In some embodiments, the pathogenic microbial cell is selected from the group consisting of: *Salmonella* spp.; *Shigella* Spp; and *Yersinia* spp. In some embodiments, the pathogenic microbial cell is selected from the group consisting of *Salmonella typhimurium* SPI1 and *Shigella flexneri* mxi-spa.

In some embodiments, the cell further comprises a nucleic acid sequence encoding one or more polypeptides that increase adhesion to the target cell. In some embodiments, the polypeptides that increase adhesion to the target cell comprise Tir and intimin. In some embodiments, the polypeptide that increases adhesion to the target cell is selected from a group consisting of a bacterial adhesion; Afa1; AIDA; invasion; or a single chain antibody specific for an extracellular epitope of a target cell polypeptide.

In some embodiments, the polypeptide comprises an N-terminal type three secretion system (T3SS) signal. In some embodiments, the nucleic acid sequence encoding the polypeptide is operatively linked to a type three secretion system (T3SS)-associated promoter or promoter element. In some embodiments, the type three secretion system (T3 SS)-associated promoter or promoter element is selected from the group consisting of MxiE recognition sequences; and an inducible promoter. In some embodiments, the nucleic acid encoding the polypeptide is operatively linked to an inducible promoter. In some embodiments, the nucleic acid encoding the polypeptide is located on a chromosome. In some embodiments, the polypeptide is an anti-inflammatory polypeptide. In some embodiments, the anti-inflammatory polypeptide is selected from the group consisting of a bacterial anti-inflammatory polypeptide; a bacterial polypeptide that inhibits NF-κB signaling; OspG; OspF; IpaH9.8; SseL; YopJ; NleB; NleC; NleE; NleH1; OspL.

In some embodiments, the non-pathogenic microbial cell is a commensal intestinal microbial cell. In some embodiments, the commensal intestinal microbial cell is *E. coli*, for example, *E. coli* NISSLE 1917 (EcN).

In some embodiments, the type three secretion system (T3SS)-compatible polypeptide is a toxin. In some embodiments, the type three secretion system (T3SS)-compatible polypeptide is a tumor suppressor polypeptide. In some embodiments, the type three secretion system (T3SS)-compatible polypeptide is a reprogramming factor. In some embodiments, the reprogramming factor is selected from the group consisting of Oct3/4; Sox2; Klf4; c-Myc; Lin28; Nanog; Sa14; Dppa2; Ezh2; and Esrrb. In some embodiments, the type three secretion system (T3SS)-compatible polypeptide is a transdifferentiation factor. In some embodiments, the transdifferentiation factor is a myocyte transdifferentiation factor selected from the group consisting of myoD. In some embodiments, the transdifferentiation factor is a cardiomyocyte transdifferentiation factor selected from the group consisting of Gata4; Mec2F; and Tbs5. In some embodiments, the type three secretion system (T3SS)-compatible polypeptide is an antigen. In some embodiments, the antigen is derived from an enteric pathogen.

In one aspect, the technology described herein relates to a method of introducing a polypeptide into a target cell, the method comprising contacting the target cell with an engineered microbial cell as described herein.

In one aspect, the technology described herein relates to a method of reducing inflammation in a subject, the method comprising administering an engineered microbial cell as described herein. In some embodiments, the subject is in need of treatment for an auto-immune disease. In some embodiments, the inflammation is inflammation of the gastrointestinal tract. In some embodiments, the subject is in need of treatment for a condition selected from the group consisting of asthma; inflammatory bowel disease; Crohn's disease; obesity; and ulcerative colitis. In some embodiments, the engineered microbial cell is administered orally.

In one aspect, the technology described herein relates to a method of treating a proliferative disease in a subject, the method comprising, administering an engineered microbial cell as described herein. In some embodiments, the proliferative disease is cancer. In some embodiments, the cancer is a cancer of the gastrointestinal tract and the microbial cell is administered orally.

In one aspect, the technology described herein relates to a method of treating a proliferative disease in a subject, the method comprising, administering an engineered microbial cell as described herein. In some embodiments, the microbial cell is administered orally.

In one aspect, the technology described herein relates to a method of reprogramming/transdifferentiating a target cell or increasing the efficiency of the reprogramming/transdifferenation of a target cell, the method comprising contacting the cell with an engineered microbial cell as described herein. In some embodiments, the method further comprises the steps of: contacting the target cell and engineered microbial cell with an antibiotic; removing unattached microbial cells and the antibiotic; and contacting the target cell with a second engineered microbial cell. In some embodiments, the steps are repeated at least once. In some embodiments, the target cell is contacted with an engineered microbial cell at least daily for a period of at least 5 days. In some embodiments, the target cell is a cell which is reprogrammed to an induced pluripotent stem cell (iPSC) phenotype. In some embodiments, the target cell is a cell which is transdifferentiated.

In one aspect, the technology described herein relates to a kit comprising the engineered microbial cell as described herein. In one aspect, the technology described herein relates to a kit comprising: an engineered microbial cell comprising a first nucleic acid sequence comprising genes encoding a functional type three secretion system (T3SS); and a second nucleic acid sequence encoding an T3SS-compatible polypeptide which is exogenous to a target cell; wherein the engineered microbial cell is non-pathogenic with respect to the target cell.

BRIEF DESCRIPTION OF THE FIGURES

FIG. 1 depicts a diagram of the two strains described in Example 6.

DETAILED DESCRIPTION

Some bacterial pathogens comprise a type three secretion system (T3SS), which serves as a needle-like system for delivering bacterial polypeptides (effectors) into host cells. These effector polypeptides typically contribute to the virulence of the bacterial cell. In contrast, commensal microbes have not been described to comprise a T3SS.

Described herein is a novel way to introduce a diverse array of peptides to a target eukaryotic cell by engineering non-pathogenic bacterial cells which express a functional T3SS to create a biological delivery system. Also described herein are compositions and methods that relate to non-pathogenic microbial cells that have been engineered to express both 1) a functional type three secretion system (T3SS) and at least one polypeptide that is compatible with the T3SS. Due to the wide variety of polypeptides that can be delivered to a target eukaryotic cell using the compositions and systems described herein, a commensurately wide variety of applications is contemplated, e.g. therapeutics and reprogramming.

In one aspect, described herein is an engineered non-pathogenic microbial cell comprising (1) a first nucleic acid sequence comprising genes encoding a functional type three secretion system (T3SS); (2) a second nucleic acid sequence encoding an T3SS-compatible polypeptide; wherein the engineered microbial cell is non-pathogenic with respect to the target cell or target organism.

For example, as described in the Examples herein, a plasmid comprising two operons encoding a functional *Shigella* T3SS (covering 31 kb) was created.

As described in the Examples herein, a vector (e.g. a plasmid) comprising one or more anti-inflammatory T3SS substrates under the control of an inducible promoter (e.g. an IPTG-regulatable promoter) is used in some applications. As described in the Examples herein, a construct comprising one or more anti-inflammatory T3SS substrates under the control of a MxiE-responsive promoter and integrated into the bacterial genome is used in some applications. Exemplary anti-inflammatory T3SS substrates used in the experiments described in the Examples herein include NleH1 (e.g., NCBI Gene ID No: 8215433 (DNA sequence disclosed as SEQ ID NO: 1; PRT sequence disclosed as SEQ ID NO: 2)); OspG (e.g., NCBI Gene ID No: 13917115 (DNA sequence disclosed as SEQ ID NO: 3; PRT sequence disclosed as SEQ ID NO: 4)); OspF (e.g., NCBI Gene ID No: 13917039 (DNA sequence disclosed as SEQ ID NO: 5; PRT sequence disclosed as SEQ ID NO: 6)); IpaH9.8 (e.g., NCBI Gene ID No: 13917118 (DNA sequence disclosed as SEQ ID NO: 7; PRT sequence disclosed as SEQ ID NO: 8)); SseL (e.g., NCBI Gene ID No: 1253809 (DNA sequence disclosed as SEQ ID NO: 9; PRT sequence disclosed as SEQ ID NO: 10)); YopJ (e.g., NCBI Gene ID No: 1149272 (DNA sequence disclosed as SEQ ID NO: 11; PRT sequence disclosed as SEQ ID NO: 12)); NleB (e.g., NCBI Gene ID No: 8869954 (DNA sequence disclosed as SEQ ID NO: 13; PRT sequence disclosed as SEQ ID NO: 14)); NleC (e.g., NCBI Gene ID No: 8869955 (DNA sequence disclosed as SEQ ID NO: 15; PRT sequence disclosed as SEQ ID NO: 16)); and NleE (e.g., NCBI Gene ID No: 8872603 (DNA sequence disclosed as SEQ ID NO: 17; PRT sequence disclosed as SEQ ID NO: 18)). As described in the Examples herein, a construct comprising a gene encoding MyoD is used in some applications (e.g. to induce transdifferentiation to a muscle cell phenotype as described elsewhere herein).

For example, a construct comprising a gene encoding MyoD is delivered to fibroblast cells (e.g. mouse embryonic fibroblasts) as described in the Examples herein. By way of further example, a construct comprising a an anti-inflammatory T3SS substrate (e.g. NleH1; OspG; OspF; IpaH9.8; SseL; YopJ; NleB; NleC; and/or NleE) is delivered to intestinal epithelial cells as described in the Examples herein.

As used herein, a “target cell” is a cell which can receive a polypeptide delivered by a bacterial T3SS. In some embodiments, a target cell is a eukaryotic cell. In some embodiments, a target cell is a cell comprised by, or originating from, a vertebrate. In some embodiments, a target cell is a cell comprised by, or originating from, a mammal. A “target organism” is an organism comprising at least one “target cell.” A target cell can be located in vitro or in vivo. In some embodiments, a target cell is an isolated target cell. In some embodiments, a target cell is not an isolated target cell. In some embodiments, the target cell is part of the target organism. As described in the Examples herein, fibroblasts (e.g. mouse embryonic fibroblasts) are used as exemplary target cells in some applications (e.g. when creating iPSC cells as described elsewhere herein). As described in the Examples herein, epithelial cells (e.g. polarized intestinal epithelial cells, e.g. Caco-2 cells) are used as exemplary target cells in some applications (e.g. when delivering anti-inflammatory peptides as described elsewhere herein). As described in the Examples herein, HEK293 are used as exemplary target cells in some applications (e.g. when delivering peptides as described elsewhere herein). As described in the Examples herein, TRUC (T-bet−/−× Rag2−/− ulcerative colitis) mice were used as exemplary target organisms in some applications (e.g. when delivering anti-inflammatory peptides as described elsewhere herein).

As used herein, the term “non-pathogenic” refers to a microbial cell which does not have a deleterious effect upon a target cell, i.e. in the presence of the non-pathogenic microbial cell, a target cell will not have a statistically significantly increased rate of cell death, nor a statistically significantly decreased metabolic rate or altered rate of growth and/or division. It is recognized that, therefore, whether a cell is non-pathogenic with respect to a target cell may vary depending upon, e.g. the environment in which the target cell is located and the concentration of the microbial cells. In some embodiments, a non-pathogenic microbial cell is non-pathogenic if it does not have a deleterious effect upon a target cell in vitro when the microbial cell is present at a concentration of less than 50× relative to the target cell. In some embodiments, a non-pathogenic microbial cell can be one that does not express a toxin having a deleterious effect upon the target cell. In some embodiments, a non-pathogenic microbial cell can be one that does not replicate within the target cell. In some embodiments, a non-pathogenic microbial cell can be one that is not found in the cytoplasm of the target cell. In some embodiments a non-pathogenic microbial cell can be one that is not found in the cytoplasm of the target cell but is found in the phagosome of the target cell. In some embodiments, a non-pathogenic microbial cell can be a commensal microbial cell. In some embodiments, a non-pathogenic microbial cell can be a non-immunogenic microbial cell, i.e. a cell that does not cause a target cell to secrete increased levels of, e.g. IL-8 when the microbial cell is present.

Non-limiting examples of non-pathogenic microbial cells with respect to human target cells can include, but are not limited to: *E. coli* K12; *E. coli* DH5α, *E. coli* HB101, *E. coli* BL21, *E. coli* DH10beta, *E. coli* JM110, *E. coli* MinT3, and virulence-cured *Shigella* strains (e.g. those missing the virulence plasmid encoding the T3SS and >20T3SS-compatible effectors). Non-limiting examples of commensal microbial cells with respect to human subjects include, but are not limited to: *E. coli* NISSLE 1917 (EcN); *E. coli* 83972; *E. coli* M17. As described in the Examples herein, *E. coli* NISSLE 1917 are used in some applications. As described in the Examples herein, *E. coli* K12 and/or DH5α are used in some applications. As described in the Examples herein, avirulent *S. flexneri* and/or *S. typhimurium* strains that no longer encode or at least no longer express any of the known effectors (e.g. strains deleted for effectors and/or known master transcription regulators that control the expression of effectors) are used in some applications.

A T3SS is a multi-protein structure found in gram negative bacteria. It moves polypeptides from the cytoplasm of the bacterial cell through the interior of the T3SS “needle” into the cytoplasm of a target cell. T3SS's are found in pathogenic strains and have been observed in pathogenic isolates of, e.g., *Shigella, Salmonella, E. coli, Burkholderia, Yersinia, Chlamydia, Pseudomonas, Erwinia, Ralstonia, Rhizobium, Vibrio*, and *Xanthamonas*. Further discussion of T3SS's can be found, e.g. in Izore et al. Structure 2011 19:603-612; Korotkov et al. Nature Reviews Microbiology 2012 10:336-351; Wooldridge, K. (ed) Bacterial Secreted Proteins. Caster Academic Press 2009; Snyder and Champness (eds.) Molecular Genetics of Bacteria. $3^{rd}$ Ed. ASM Press: 2007; each of which is incorporated by reference herein in its entirety.

The suite of T3SS-related proteins in a given wild-type cell is typically divided into structural proteins (those proteins which form the needle itself), substrate proteins (those proteins which are transported through the needle to the host), and chaperones (those proteins that bind effectors in the cytoplasm to protect, process, and/or shuttle the effectors to the needle). As used herein, a “functional T3SS” refers, minimally, to the set of structural proteins which are required in order to transfer at least one polypeptide to a target cell. In some embodiments, a functional T3SS system can comprise one or more chaperone proteins. In some embodiments, a functional T3SS can comprise one or more, for example, two, three, or four, substrates which are not virulence factor (e.g. certain translocators). In some embodiments, a functional T3SS does not comprise a virulence factor which is delivered to the target cell.

As used herein, a “virulence factor” refers to those substrates which affect and/or manipulate a target cell in a manner which is beneficial to infection and deleterious to the target cell, i.e. they perturb the normal function of the target cell. Examples of actions of virulence factors include, but are not limited to, modulation of actin polymerization, induction of apoptosis, modulation of the cell cycle, modulation of gene transcription. Not all substrates are necessarily virulence factors. By way of non-limiting example, a T3SS (and a functional T3SS) can comprise proteins referred to as translocators. These substrates are secreted by the T3SS as it nears a complete form and create a pore in the target cell membrane, allowing further substrates to be delivered into the cytoplasm of the target cell, i.e. translocators are substrates in that they travel through the needle to the target cell and are also structural proteins in that they form part of the structure through which other substrates are delivered into the target cell. In some embodiments, a single polypeptide can be both a translocator and a virulence factor (e.g. IpaB of *Shigella*).

In some embodiments, a functional T3SS can comprise one or more translocators.

In some embodiments, a functional T3SS does not comprise a translocator that also has virulence factor activity.

The minimal set of proteins required for a functional T3SS can vary depending upon, e.g. the identity of the polypeptide which is to be transferred, the origin of the T3SS, the identity of the non-pathogenic bacterial cell, and/or the identity of the host cell.

In some embodiments, a functional T3SS can comprise one or more of a needle monomer polypeptide, an inner rod polypeptide, ring polypeptides, one or more translocators, a needle-tip polypeptide, a ruler polypeptide, and/or an ATPase.

In some embodiments, a functional T3SS can comprise a needle monomer polypeptide (e.g. MxiH (e.g., NCBI Gene ID No: 1238256 (DNA sequence disclosed as SEQ ID NO: 19; PRT sequence disclosed as SEQ ID NO: 20)); PrgI (e.g., NCBI Gene ID No: 1254396 (DNA sequence disclosed as SEQ ID NO: 21; PRT sequence disclosed as SEQ ID NO: 22)); YscF (e.g., NCBI Gene ID No: 1172700 (DNA sequence disclosed as SEQ ID NO: 23; PRT sequence disclosed as SEQ ID NO: 24)); and/or EscF (e.g., NCBI Gene ID No: 8873370 (DNA sequence disclosed as SEQ ID NO: 25; PRT sequence disclosed as SEQ ID NO: 26))), an inner rod polypeptide (e.g. MxiI (e.g., NCBI Gene ID No: 1238257 (DNA sequence disclosed as SEQ ID NO: 27; PRT sequence disclosed as SEQ ID NO: 28)); PrgJ (e.g., NCBI Gene ID No: 1254395 (DNA sequence disclosed as SEQ ID NO: 29; PRT sequence disclosed as SEQ ID NO: 30)); YscI (e.g., NCBI Gene ID No: 2767498 (DNA sequence disclosed as SEQ ID NO: 31; PRT sequence disclosed as SEQ ID NO: 32)); and/or EscI (e.g., NCBI Gene ID No: 8219253 (DNA sequence disclosed as SEQ ID NO: 33; PRT sequence disclosed as SEQ ID NO: 34))), ring polypeptides, one or more translocators (e.g. IpaC (e.g., NCBI Gene ID No: 876448 (DNA sequence disclosed as SEQ ID NO: 35; PRT sequence disclosed as SEQ ID NO: 36)); SipB (e.g., NCBI Gene ID No: 1254408 (DNA sequence disclosed as SEQ ID NO: 37; PRT sequence disclosed as SEQ ID NO: 38)); SipC (e.g., NCBI Gene ID No: 1254407 (DNA sequence disclosed as SEQ ID NO: 39; PRT sequence disclosed as SEQ ID NO: 40)); YopB (e.g., NCBI Gene ID No: 1449456 (DNA sequence disclosed as SEQ ID NO: 41; PRT sequence disclosed as SEQ ID NO: 42)); YopD (e.g., NCBI Gene ID No: 1449455 (DNA sequence disclosed as SEQ ID NO: 43; PRT sequence disclosed as SEQ ID NO: 44)); EspD (e.g., NCBI Gene ID No: 885777 (DNA sequence disclosed as SEQ ID NO: 45; PRT sequence disclosed as SEQ ID NO: 46)); and/or EspB (e.g., NCBI Gene ID No: 8474872 (DNA sequence disclosed as SEQ ID NO: 47; PRT sequence disclosed as SEQ ID NO: 48))); a needle-tip polypeptide (e.g. IpaD (e.g., NCBI Gene ID No: 876444 (DNA sequence disclosed as SEQ ID NO: 49; PRT sequence disclosed as SEQ ID NO: 50)); SipD (e.g., NCBI Gene ID No: 1254406 (DNA sequence disclosed as SEQ ID NO: 51; PRT sequence disclosed as SEQ ID NO: 52)); LcrV (e.g., NCBI Gene ID No: 1172676 (DNA sequence disclosed as SEQ ID NO: 53; PRT sequence disclosed as SEQ ID NO: 54)); and/or EspA (e.g., NCBI Gene ID No: 960865 (DNA sequence disclosed as SEQ ID NO: 55; PRT sequence disclosed as SEQ ID NO: 56))); a ruler polypeptide (e.g. Spa32 (e.g., NCBI Gene ID No: 876502 (DNA sequence disclosed as SEQ ID NO: 57; PRT sequence disclosed as SEQ ID NO: 58)); InvJ (e.g., NCBI Gene ID No: 1254415 (DNA sequence disclosed as SEQ ID NO: 59; PRT sequence disclosed as SEQ ID NO: 60)); YscP (e.g., NCBI Gene ID No: 5798302 (DNA sequence disclosed as SEQ ID NO: 61; PRT sequence disclosed as SEQ ID NO: 62)); and/or Orf16 (e.g., NCBI Gene ID No: 8219247 (DNA sequence disclosed as SEQ ID NO: 63; PRT sequence disclosed as SEQ ID NO: 64))), and an ATPase (e.g. Spa47 (e.g., NCBI Gene ID No: 876429 (DNA sequence disclosed as SEQ ID NO: 65; PRT sequence disclosed as SEQ ID NO: 66)); InvC (e.g., NCBI Gene ID No: 1254417 (DNA sequence disclosed as SEQ ID NO: 67; PRT sequence disclosed as SEQ ID NO: 68)); YscN (e.g., NCBI Gene ID No: 10216379 (DNA sequence disclosed as SEQ ID NO: 69; PRT sequence disclosed as SEQ ID NO: 70)); and/or SepB (also known as EscN) (e.g., NCBI Gene ID No: 8873386 (DNA sequence disclosed as SEQ ID NO: 71; PRT sequence disclosed as SEQ ID NO: 72))). In some embodiments, a functional T3SS can further comprise a chaperone for the one or more translocators (e.g. IpgC (e.g., NCBI Gene ID No: 1238043 (DNA sequence disclosed as SEQ ID NO: 73; PRT sequence disclosed as SEQ ID NO: 74)); SicA (e.g., NCBI Gene ID No: 1254409 (DNA sequence disclosed as SEQ ID NO: 75; PRT sequence disclosed as SEQ ID NO: 76)); SycD (e.g., NCBI Gene ID No: 2767486 (DNA sequence disclosed as SEQ ID NO: 77; PRT sequence disclosed as SEQ ID NO: 78)); and/or CesD (e.g., NCBI Gene ID No: 7063867 (DNA sequence disclosed as SEQ ID NO: 79; PRT sequence disclosed as SEQ ID NO: 80))). In some embodiments, a functional T3SS can further comprise one or more of a switch polypeptide (e.g. Spa40 (e.g., NCBI Gene ID No: 876433 (DNA sequence disclosed as SEQ ID NO: 81; PRT sequence disclosed as SEQ ID NO: 82)); SpaS (e.g., NCBI Gene ID No: 1254410 (DNA sequence disclosed as SEQ ID NO: 83; PRT sequence disclosed as SEQ ID NO: 84)); YscU (e.g., NCBI Gene ID No: 2767517 (DNA sequence disclosed as SEQ ID NO: 85; PRT sequence disclosed as SEQ ID NO: 86)); and/or EscU (e.g., NCBI Gene ID No: 7062687 (DNA sequence disclosed as SEQ ID NO: 87; PRT sequence disclosed as SEQ ID NO: 88))) and a gatekeeper polypeptide (e.g. MxiC (e.g., NCBI Gene ID No: 876426 (DNA sequence disclosed as SEQ ID NO: 89; PRT sequence disclosed as SEQ ID NO: 90)); InvE (e.g., NCBI Gene ID No: 1254420 (DNA sequence disclosed as SEQ ID NO: 91; PRT sequence disclosed as SEQ ID NO: 92)); YopN (e.g., NCBI Gene ID No: 2767534 (DNA sequence disclosed as SEQ ID NO: 93; PRT sequence disclosed as SEQ ID NO: 94)); and/or SepL (e.g., NCBI Gene ID No: 8873375 (DNA sequence disclosed as SEQ ID NO: 95; PRT sequence disclosed as SEQ ID NO: 96))).

In some embodiments, the functional type three secretion system (T3SS) can comprise polypeptides endogenous to a bacterium selected from the group consisting of: *Shigella* spp; *Salmonella* spp; enteropathogenic *E. coli*; and *Yersinia* spp. In some embodiments, the genes encoding a functional type three secretion system (T3SS) comprise: virB; acp; ipaA; ipaB; ipaC; ipaD; ipgC; ipgB1; ipgA; icsB; ipgD; ipgE; ipgF; mxiG; mxiH; mxiI; mxiJ; mxiK; mxiN; mxiL;

mxiM; mxiE; mxiD; mxiC; mxiA; spa15; spa47; spa13; spa32; spa33; spa24; spa9; spa29; and spa40 and/or homologs thereof.

In some embodiments, the first nucleic acid sequence comprising genes encoding a functional type three secretion system (T3SS) can comprise one contiguous sequence. In some embodiments, the first nucleic acid sequence comprising genes encoding a functional type three secretion system (T3SS) is located on a plasmid. In some embodiments, the first nucleic acid sequence comprising genes encoding a functional type three secretion system (T3SS) is located on a chromosome (e.g. a naturally-occurring chromosome, a modified endogenous chromosome, or a bacterial artificial chromosome (BAC)). In some embodiments, the first nucleic acid sequence comprising genes encoding a functional type three secretion system (T3SS) can comprise one or more operons, e.g. one operon, two operons, three operons, or more operons. In some embodiments, the first nucleic acid sequence comprising genes encoding a functional type three secretion system (T3SS) can comprise one or more separate sequences and/or molecules (e.g. a portion of the genes are found on one plasmid and another portion of the genes are found on a second plasmid). In some embodiments, the first nucleic acid sequence can be integrating into the chromosome using, for example, landing pad technology, see, e.g. Kuhlman and Cox, 2010 Nucleic Acids Research 38:e92; which is incorporated by reference herein in its entirety.

In some embodiments, a functional T3SS system can be introduced into a non-pathogenic bacterial cell. In alternative embodiments, a pathogenic bacterial cell comprising a functional T3SS can be engineered to be non-pathogenic, e.g. by deleting or mutation one or more T3SS components. Non-limiting examples of T3 SS components that can be deleted or mutated to engineer a non-pathogenic bacterial cell include: a toxin; a T3SS substrate; a structural T3SS polypeptide; a master regulator of T3SS components; and any combination thereof. Such deletions and/or mutations have been described in the art, e.g. non-limiting examples include virulence-curing of *S. typhimurium* by removing a virulence plasmid (see, e.g. Gulig and Curtiss. Infect Immun 1987 55:2891-2901; which is incorporated by reference herein in its entirety) and virulence-curing of *S. typhimurium* by mutation and/or of master regulators, e.g. master regulators of genes encoding endogenous T3SS substrates (see, e.g., Eichelberg and Galan. Infect immune 1999 67:4099-4105; which is incorporated by reference herein in its entirety). In some embodiments, the T3SS component is located on a plasmid. For example, *Yersinia* and *Shigella* encode type 3 secretion systems in plasmids. In some embodiments, a plasmid comprising the T3SS component is removed from the bacterial cell, such as *Shigella*. In some embodiments, the pathogenic microbial cell is selected from the group consisting of: *Salmonella* spp.; *Shigella* Spp; and *Yersinia* spp. In some embodiments, the pathogenic microbial cell is selected from the group consisting of: *Salmonella typhimurium* SPI1 and *Shigella flexneri* mxi-spa. For example, one can introduce the T3SS encoding plasmid into virulence plasmid cured strains of *Shigella*.

The delivery of a polypeptide via a T3SS requires close proximity of the microbial cell and the target cell. Accordingly, in some embodiments, delivery of a polypeptide can be increased or enhanced by causing and/or increasing adhesion of the microbial cell to the target cell. In some embodiments, the engineered microbial cell further comprises a nucleic acid sequence encoding one or more polypeptides that increase adhesion to the target cell. A number of polypeptides can increase adhesion.

In some embodiments, the polypeptides that increase adhesion to the target cell comprise Tir and intimin, e.g. from enteropathogenic *E. coli*. Intimin is an outer membrane protein and Tir is a substrate of the T3SS which, upon delivery to a target cell, integrates into the plasma membrane and acts as a receptor for intimin. In some embodiments, an engineered microbial cell comprising a nucleic acid sequence encoding intimin and Tir can also comprise a nucleic acid sequence encoding the Tir chaperone CesT.

In some embodiments, the polypeptide that increases adhesion to the target cell can be selected from the group consisting of a bacterial adhesin; AfaI; AIDA; invasin; or a single chain antibody specific for an extracellular epitope of a target cell polypeptide. In some embodiments, the extracellular epitope of the target cell can be specific for a certain type of target cell, e.g. a cancer-cell specific epitope and/or a tissue-specific epitope in order to target delivery of polypeptides to a particular cell type.

As described herein, four endogenous *Shigella* polypeptides, when secreted by a functional type 3 secretion system, are sufficient to enable a bacterial cell to mediate its uptake into a target cell. Accordingly, engineered bacterial cells as described herein that comprise these four polypeptides (or homologs thereof) can be internalized by a target cell and can deliver their T3 SS-compatible polypeptide(s) before, during, and/or after internalization into the target cell. Their uptake by the target cell can also trigger, e.g. innate immune responses leading to cell death. In some embodiments, uptake can trigger innate immune responses potentially leading to cell death. Such engineered bacterial cells can be suitable, for example, for use in methods where it is desired to kill the target cell, e.g. in treating a solid tumor. In some embodiments, a commensal cell is engineered to comprise the four *Shigella* polypeptides and/or homologs thereof. In some embodiments, a pathogenic cell engineered to be avirulent is engineered such that it retains the four *Shigella* polypeptides and/or homologs thereof. In some embodiments, any one of the four *Shigella* polypeptides is sufficient to induce the uptake of the bacterial cell. In some embodiments, an engineered cell is engineered such that the engineered cell introduces less than four *Shigella* polypeptides and/or homologs thereof, e.g. only one of the polypeptides, only two of the polypeptides, or only three of the polypeptides.

Conversely, cells lacking all four of these endogenous *Shigella* polypeptides cannot mediate uptake by the target cell and remain in the extracellular environment. Such engineered bacterial cells can be suitable for use in methods where is undesirable to activate innate immune responses, e.g. when reprogramming the target cell or delivering anti-inflammatory proteins to the target cell. In some embodiments, a commensal cell is engineered such that it does not any of the four *Shigella* polypeptides and/or homologs thereof, e.g. it retains none of the polypeptides. In some embodiments, a pathogenic cell engineered to be avirulent is engineered such that it does not any of the four *Shigella* polypeptides and/or homologs thereof, e.g. it retains none of the polypeptides.

The four endogenous *Shigella* polypeptides referred to above are IpgB1 (e.g., NCBI Ref Seq: NP_858263 (SEQ ID NO: 97)); IpgD (e.g., NCBI Ref Seq: NP_085296 (SEQ ID NO: 98)); IpaA (e.g., NCBI Ref Seq: NP_858264 (SEQ ID NO: 99)) and IcsB (e.g., NCBI Ref Seq: NP_085294 (SEQ ID NO: 100)). Homologs of the foregoing *Shigella* polypeptides are also contemplated for use in the compositions and methods described herein. By way of non-limiting example, SopB (e.g., NCBI Ref Seq: NP_460064 (SEQ ID NO: 101)) is a homolog of IpgD and SipA (e.g., NCBI Ref Seq: NP 461803 (SEQ ID NO: 102)) is a homolog of IpaA. Numerous species have a Rho GTP exchange factor that is a homolog of IpgB1.

Homologs of any given polypeptide or nucleic acid sequence can be found using, e.g., BLAST programs (freely available on the world wide web at http://blast.ncbi.nlm.nih.gov/), e.g. by searching freely available databases of sequence for homologous sequences, or by querying those databases for annotations indicating a homolog (e.g. search strings that comprise a gene name or describe the activity of a gene). The homologous amino acid or DNA sequence can be at least 90%, at least 95%, at least 96%, at least 97%, at least 98%, at least 99%, or more, identical to a reference sequence. The degree of homology (percent identity) between a reference and a second sequence can be determined, for example, by comparing the two sequences using freely available computer programs commonly employed for this purpose on the world wide web.

In some embodiments of any of the aspect described herein, a homolog can be a polypeptide with the same function, functional characteristics, and/or activity as the reference polypeptide. By way of non-limiting example, a homolog with the same function as one of the four endogenous *Shigella* polypeptides mentioned above (i.e. IpgB1; IpgD; IpaA; and IcsB) can be identified by engineering a bacteria to not express one of IpgB1; IpgD; IpaA; and IcsB and to instead express a putative functional homolog and then measuring the ability of the bacteria to invade a target cell. If the bacteria retains at least 10% of the reference ability to invade a target cell, the putative functional homolog is demonstrated to be a functional homolog. In some embodiments, a functional homolog has at least 10% of the activity of the reference polypeptide, e.g. 10% or more, 20% or more, 30% or more, 50% or more, 75% or more, 80% or more, 90% or more, 95% or more, or 100% or more of the activity of the reference polypeptide.

In addition to a first nucleic acid sequence comprising genes encoding a functional type three secretion system (T3SS), the engineered non-pathogenic microbial cells described herein further comprise a second nucleic acid sequence encoding a T3SS-compatible polypeptide. As used herein the term "T3SS-compatible polypeptide" refers to any polypeptide expressed in the microbial cell that, in the presence of a functional T3SS, can be delivered to the cytoplasm of a target cell. A T3SS-compatible polypeptide can be from any source, e.g. the polypeptide can have a prokaryotic origin, a eukaryotic origin, or a synthetic origin. A T3 SS-compatible polypeptide can be a naturally-occurring polypeptide or a mutant and/or variant thereof. In a variant T3SS-compatible polypeptide, one or more residues can be altered, deleted, and/or added as compared to a naturally-occurring and/or wild-type polypeptide so long as the function remains substantially the same.

In some embodiments, the T3SS-compatible polypeptide is exogenous to the microbial cell. In some embodiments, the T3SS-compatible polypeptide is endogenous to the microbial cell. In some embodiments, the T3SS-compatible polypeptide is ectopic to the microbial cell. In some embodiments, the T3SS-compatible polypeptide is ectopic with respect to the target cell. In some embodiments, the T3SS-compatible polypeptide is exogenous with respect to the target cell. In some embodiments, the T3SS-compatible polypeptide is endogenous with respect to the target cell.

The term "exogenous" refers to a substance present in a cell other than its native source. The term "exogenous" when used herein can refer to a nucleic acid (e.g. a nucleic acid encoding a T3SS-compatible polypeptide) or a polypeptide (e.g., T3SS-compatible polypeptide) that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in low amounts and one wishes to increase the amount of the nucleic acid or polypeptide in the cell or organism. A substance (e.g. a nucleic acid encoding T3SS-compatible polypeptide and/or a T3SS-compatible polypeptide) will be considered exogenous if it is introduced into a cell or an ancestor of the cell from which the cell has inherited the substance. In contrast, the term "endogenous" refers to a substance that is native to the biological system or cell (e.g. the microbial cell and/or target cell). As used herein, "ectopic" refers to a substance that is found in an unusual location and/or amount. An ectopic substance can be one that is normally found in a given cell, but at a much lower amount and/or at a different time.

In some embodiments, the T3SS-compatible polypeptide can be a naturally-occurring bacterial polypeptide which is delivered to a target cell via a T3SS, e.g. a T3SS substrate with anti-inflammatory action (described further below herein). In some embodiments, the T3SS-compatible polypeptide is exogenous to the microbial cell, e.g. the microbial cell is a naturally non-pathogenic microbial cell which has been engineered to comprise a functional T3SS and the T3SS-compatible polypeptide is a polypeptide which is exogenous to the microbial cell. In some embodiments, the T3SS-compatible polypeptide is endogeouns to the microbial cell, e.g. the microbial cell is one that has an endogenous T3SS and has been engineered to be non-pathogenic and the T3SS-compatible polypeptide is an endogenous T3SS substrate.

In some embodiments, the T3SS-compatible polypeptide is ectopic with respect to the target cell. As described further below herein, in some embodiments, the microbial cells described herein can be used to deliver eukaryotic polypeptides which may be encoded by a nucleic acid sequence found in the target cell. In such embodiments, delivery via the microbial cells can permit the level of the polypeptide in the target cell to be increased, e.g. causing a certain level of a polypeptide to be present in a cell type that typically does not express the desired level of the polypeptide. In a further non-limiting embodiment, delivery via the microbial cells can permit the level of the polypeptide to be increased in a cell type that typically does not express the desired level of the polypeptide.

In some embodiments, e.g where the T3SS-compatible polypeptide comprises a polypeptide sequence which is not endogenously delivered via a T3SS (e.g. the polypeptide sequence is endogenous to a eukaryotic cell, the polypeptide is endogenous to a prokaryotic cell but is not naturally a T3SS substrate, or is endogenously a prokaryotic polypeptide delivered by a different T3SS than the one present in the engineered microbial cell), the T3SS-compatible polypeptide can comprise an N-terminal type three secretion system (T3SS) signal.

Naturally-occurring T3SS substrates comprise a secretion signal within the first 20 amino acids of the polypeptide.

Certain naturally-occurring T3SS substrates comprise a chaperone-binding domain within the first 50 amino acids of the polypeptide.

Accordingly, in some embodiments, the T3SS-compatible peptide can comprise an N-terminal type three secretion system (T3SS) signal, wherein the T3SS signal comprises a T3SS secretion signal. In some embodiments, the T3SS-compatible peptide can comprise an N-terminal type three secretion system (T3SS) signal, wherein the T3SS signal comprises the first 20 amino acids of a naturally occurring T3SS substrate. In some embodiments, the T3SS-compatible peptide can comprise an N-terminal type three secretion system (T3SS) signal, wherein the T3SS signal comprises a T3SS chaperone-binding domain. In some embodiments, the T3SS-compatible peptide can comprise T3SS chaperone-binding domain and an N-terminal type three secretion system (T3SS) signal, wherein the T3SS signal comprises from about the first 50 to about the first 70 amino acids of a naturally occurring T3SS substrate. In some embodiments, in the context of a T3SS signal polypeptide, the term "about" can refer to ±3 amino acids. In some embodiments, in the context of a T3SS signal polypeptide, the term "about" can refer to ±2 amino acids. In some embodiments, in the context of a T3SS signal polypeptide, the term "about" can refer to ±1 amino acid.

Examples of T3SS secretion signals and chaperone-binding domains are known in the art, see, e.g. Schmitz et al. Nat Methods 2009 6:500-2; which described the signals and domains of *Shigella* effectors and which is incorporated by reference herein in its entirety. Additional examples are known in the art, e.g. Sory et al. PNAS 1995 92:11998-20002; which is incorporated by reference herein in its entirety. It is contemplated that a T3SS signal may reduce the activity of the non-T3SS signal portion of the T3SS-compatible polypeptide once it is delivered to the target cell. Accordingly, in some embodiments, the T3SS-compatible polypeptide can comprise a cleavage site after the T3SS signal sequence. In some embodiments, the cleavage site is a site recognized by an endogenous component of the target cell, e.g. a calpain, sumo, and/or furin cleavage site. In some embodiments, instead of a cleavage site, the T3SS-compatible polypeptide can comprise a ubiquitin molecule after the T3SS signal sequence such that the ubiquitin molecule and the sequence N-terminal of it is removed from the remainder of the polypeptide by a eukaryotic target cell. In some embodiments, the first amino acid C-terminal of the ubiquitin molecule can be a methionine.

In order for the T3SS-compatible polypeptide to be expressed, the nucleic acid encoding the T3 SS-compatible polypeptide can be operatively linked to a promoter. In some embodiments, the T3SS-compatible polypeptide can be constitutively expressed. In some embodiments, nucleic acids encoding the T3SS-compatible polypeptide can be operatively linked to a constitutive promoter. In some embodiments, the T3SS-compatible polypeptide can be inducibly expressed. In some embodiments, nucleic acids encoding the T3SS-compatible polypeptide can be operatively linked to an inducible promoter.

As described herein, an "inducible promoter" is one that is characterized by initiating or enhancing transcriptional activity when in the presence of, influenced by, or contacted by an inducer or inducing agent than when not in the presence of, under the influence of, or in contact with the inducer or inducing agent. An "inducer" or "inducing agent" may be endogenous, or a normally exogenous compound or protein that is administered in such a way as to be active in inducing transcriptional activity from the inducible promoter. In some embodiments, the inducer or inducing agent, e.g., a chemical, a compound or a protein, can itself be the result of transcription or expression of a nucleic acid sequence (e.g., an inducer can be a transcriptional repressor protein), which itself may be under the control or an inducible promoter. Non-limiting examples of inducible promoters include but are not limited to, the lac operon promoter, a nitrogen-sensitive promoter, an IPTG-inducible promoter, a salt-inducible promoter, and tetracycline, steroid-responsive promoters, rapamycin responsive promoters and the like. Inducible promoters for use in prokaryotic systems are well known in the art, see, e.g. the beta.-lactamase and lactose promoter systems (Chang et al., Nature, 275: 615 (1978, which is incorporated herein by reference); Goeddel et al., Nature, 281: 544 (1979), which is incorporated herein by reference), the arabinose promoter system, including the araBAD promoter (Guzman et al., J. Bacteriol., 174: 7716-7728 (1992), which is incorporated herein by reference; Guzman et al., J. Bacteriol., 177: 4121-4130 (1995), which is incorporated herein by reference; Siegele and Hu, Proc. Natl. Acad. Sci. USA, 94: 8168-8172 (1997), which is incorporated herein by reference), the rhamnose promoter (Haldimann et al., J. Bacteriol., 180: 1277-1286 (1998), which is incorporated herein by reference), the alkaline phosphatase promoter, a tryptophan (trp) promoter system (Goeddel, Nucleic Acids Res., 8: 4057 (1980), which is incorporated herein by reference), the $P_{LtetO\text{-}1}$ and $P_{lac/are\text{-}1}$ promoters (Lutz and Bujard, Nucleic Acids Res., 25: 1203-1210 (1997), which is incorporated herein by reference), and hybrid promoters such as the tac promoter. deBoer et al., Proc. Natl. Acad. Sci. USA, 80: 21-25 (1983), which is incorporated herein by reference.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent may comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Appropriate environmental inducers can include, but are not limited to, exposure to heat (i.e., thermal pulses or constant heat exposure), various steroidal compounds, divalent cations (including Cu2+ and Zn2+), galactose, tetracycline, IPTG (isopropyl-(3-D thiogalactoside), as well as other naturally occurring and synthetic inducing agents and gratuitous inducers.

Inducible promoters useful in the methods and systems as disclosed herein also include those that are repressed by "transcriptional repressors" that are subject to inactivation by the action of environmental, external agents, or the product of another gene. Such inducible promoters may also be termed "repressible promoters" where it is required to distinguish between other types of promoters in a given module or component of the biological switch converters described herein. Preferred repressors for use in the present invention are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause the dissociation of the tet repressor from the engineered promoter and allow transcription of the sequence downstream of the engineered promoter to occur.

Expression of the T3SS-compatible polypeptide can be most appropriate at the times that the functional T3SS is expressed and/or active. One way of permitting the T3SS-compatible polypeptide to be expressed with the functional T3SS is expressed and/or active is for the polypeptide to be operatively linked to a type three secretion system (T3 SS)-associated promoter or promoter element. In some embodiments, a T3 SS-associated promoter and/or promoter element is a promoter and/or promoter element which endogenously controls the expression of a structural T3SS component, and/or a T3SS chaperone, and/or a T3SS substrate. Non-limiting examples of T3SS-associated promoters and/or promoter elements include MxiE or VirB recognition sequences, which are described, e.g. in Mavris et al. J Bact 2002 184:4409-19 and Beloin et al. JBC 2002 277:15333-15344; which are incorporated by reference herein in their entirety.

In some embodiments, a nucleic acid encoding a T3SS-compatible polypeptide is present within the prokaryotic genome, e.g. the nucleic acids can be incorporated into the genome. Typically, in bacteria, one uses homologous recombination to target genes to specific sites on bacterial chromosomes. In some embodiments, a nucleic acid encoding a T3SS-compatible polypeptide is present within a vector. The term "vector", as used herein, refers to a nucleic acid construct designed for delivery to a host cell or transfer between different host cells. As used herein, a vector can be viral or non-viral. Many vectors useful for transferring exogenous genes into target cells are available, e.g. the vectors may be episomal, e.g., plasmids, virus derived vectors or may be integrated into the target cell genome, through homologous recombination or random integration. In some embodiments, a vector can be an expression vector. As used herein, the term "expression vector" refers to a vector that has the ability to incorporate and express heterologous nucleic acid fragments in a cell. An expression vector may comprise additional elements. The nucleic acid incorporated into the vector can be operatively linked to an expression control sequence when the expression control sequence controls and regulates the transcription and translation of that polynucleotide sequence.

In some embodiments, a nucleic acid encoding a T3SS-compatible polypeptide is present within a portion of a plasmid. Plasmid vectors can include, but are not limited to, pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif, which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference in its entirety).

As used herein, the term "viral vector" refers to a nucleic acid vector construct that includes at least one element of viral origin and has the capacity to be packaged into a viral vector particle. The viral vector can contain a transgenic gene in place of non-essential viral genes. The vector and/or particle may be utilized for the purpose of transferring any nucleic acids into cells either in vitro or in vivo. Numerous viral vectors are known in the art and can be used as carriers of a nucleic acid into a cell, e.g. lambda vector system gt11, gt WES.tB, Charon 4.

Anti-Inflammatory.

In some embodiments, the T3SS-compatible polypeptide can comprise an anti-inflammatory polypeptide. Non-limiting examples of anti-inflammatory polypeptides include a bacterial anti-inflammatory polypeptide; a bacterial polypeptide that inhibits NF-κB signaling; OspG; OspF; IpaH9.8; SseL; YopJ; NleB; NleC; NleE; NleH1; and OspF (for further discussion of bacterial anti-inflammatory proteins, see, e.g. Table 1 herein and Kim et al. PNAS 2005 102:14046-51; Arbibe et al.; Nat Immunol 2007 8:47-56; Ashida et al. Nat Cell Biol 2010 12:66-73; Sanada et al. Nature 2012 483:623-6; Le Negrate et al. J Immunol 2008 180:5045-56; Zhou et al. J Exp Med 2005 202:1327-32; Newton et al. PLoS Pathog 2010 6:e1000898; Baruch et al. EMBO J 2011 30:221-231; Zhang et al. Nature 2011 481: 204-8; Gao et al. PLoS Pathog 2009 5:e1000708; each of which is incorporated by reference herein). In some embodiments, the non-pathogenic microbial cell is a commensal intestinal microbial cell. A non-limiting example of a commensal intestinal microbial cell is *E. coli* NISSLE 1917 (EcN). In one aspect, the technology described herein relates to a method of reducing inflammation in a subject, the method comprising administering an engineered microbial cell comprising an anti-inflammatory T3SS-compatible polypeptide to the subject. In some embodiments, the subject is in need of treatment for an auto-immune disease. In some embodiments, the inflammation is inflammation of the gastrointestinal tract. In some embodiments, the subject is in need of treatment for a condition selected from the group consisting of asthma; inflammatory bowel disease; Crohn's disease; obesity; and ulcerative colitis. In some embodiments, the engineered microbial cell is administered orally. In certain pathologies, e.g. obesity and asthma, the flora of a subject is altered (i.e. the species of microbes and the proportion of the total population comprised by any given species is different than that observed in healthy individuals). It is contemplated herein that administration of a an engineered microbial cell comprising an anti-inflammatory T3SS-compatible polypeptide, by altering the inflammatory status of the subject, can cause the population of microbes present within the subject to revert to a population which more closely resembles that in a healthy or normal subject. This modulation of the flora can, in and of itself, have a therapeutic and/or beneficial effect upon the subject in addition to modulation of the inflammatory status.

Proliferative Disease Treatment.

In some embodiments, the T3SS-compatible polypeptide is a toxin. In some embodiments, the T3SS-compatible polypeptide is a toxin with respect to the target cell. In some embodiments, the toxin can be a naturally occurring T3SS substrate which inhibits the growth of a target cell. In some embodiments, the T3SS-compatible polypeptide is a tumor suppressor polypeptide. In some embodiments, the T3SS-compatible polypeptide can be a Talens or zinc finger nuclease that can excise activated oncogenes and/or other proteins essential to the growth of a tumor cell. In some embodiments, the protein essential to the growth of a tumor cell can be non-essential for the growth of a healthy cell. In some embodiments, the T3SS-compatible polypeptide blocks the function of a protein essential for tumor growth. In some embodiments, the engineered microbial can home to, or preferentially adhere to tumor cells. By way of non-limiting example, *E. coli* NISSLE 1917 can home to tumors (see, e.g., Stritzker et al. I J Med Micro 2007 297:151-162 and Zhang et al. Appl Environ Microbiol 2012 78:7603-10; each of which is incorporated by reference herein in its entirety), a microbial cell expressing *Yersinia* invasin can preferentially bind colorectal cancer cells (which express on their apical surface beta-integrins which are normally found only on the basolateral surface of colonic epithial cells) or a microbial cell as described herein can be further engineered to express an antibody (e.g. a single chain antibody) that recognizes a tumor-specific cell surface protein. In one aspect, described herein is a method of treating a proliferative disease in a subject, the method comprising, administering an engineered microbial cell comprising a T3SS-compatible toxin and/or tumor suppressor polypeptide to the subject. In some embodiments, the proliferative disease is cancer. In some embodiments, the cancer is a cancer of the gastrointestinal tract and the microbial cell is administered orally.

Reprogramming & Transdifferentiation.

In some embodiments, the T3SS-compatible polypeptide is a reprogramming factor, e.g. a polypeptide that causes (or increases the rate/efficiency thereof) an at least partially differentiated cell to assume a less differentiated state. Reprogramming factors are known in the art and include, by way of non-limiting example, Oct3/4; Sox2; Klf4; c-Myc; Lin28; Nanog; Sa14; Dppa2; Ezh2; and Esrrb. Further discussion of reprogramming factors can be found, e.g. in Sterneckert et al. Stem Cells 2012 30:15-21; Plath et al. Nature Reviews Genetics 2011 12:253-265; Wang et al. EMBO Reports 2011 12:373-8; Mali et al. Stem cells 30:75-81; and Papp and Plath. Cell Res 2011 21:486-501; each of which is incorporated by reference herein in its entirety. In some embodiments, the T3SS-compatible polypeptide is a transdifferentiation factor, e.g. a protein that causes (or increases the rate/efficiency thereof) a cell to assume a new differentiated phenotype (e.g. causes a fibroblast cell to transdifferentiate to a myocyte and/or cardiomyocte phenotype). Transdifferentiation factors are known in the art and include, e.g. myoD, which can cause transdifferentiation from a fibroblast phenotype to myocyte phenotype and Gata4; Mec2F; and Tbs5 which can cause transdifferentiation from a fibroblast phenotype to cardiomyocyte phenotype. Further discussion of transdifferentiation factors can be found, e.g. in Pournasr et al. Stem Cells 2011 29:1933-1941; Masip et al. Molecular Human Reproduction 2010 16:856-868; and Ma et al. Circ Res 2013 112:562-574; each of which is incorporated by reference herein in its entirety. In one aspect, described herein is a method of reprogramming and/or transdifferentiating a target cell or increasing the efficiency of the reprogramming and/or transdiffereniation of a target cell, the method comprising contacting the cell with an engineered microbial cell comprising a T3SS-compatible reprogramming and/or transdifferentiation factor polypeptide. In some embodiments, the target cell is an isolated target cell. In some embodiments, the method further comprises the steps of a) contacting the target cell and engineered microbial cell with an antibiotic; b) removing unattached microbial cells and the antibiotic; and c) contacting the target cell with a second engineered microbial cell. In some embodiments, steps a-c are repeated at least once. In some embodiments, the target cell is contacted with an engineered microbial cell at least daily for a period of at least 5 days. In some embodiments, the target cell is a cell which is reprogrammed to an induced pluripotent stem cell (iPSC) phenotype. In some embodiments, the target cell is a cell which is transdifferentiated. It is specifically contemplated that the method described herein for reprogramming and/or transdifferentiation permits a viral-free method of reprogramming and/or transdifferentiation which does not genetically modify the target cell.

Mucosal Vaccine.

In some embodiments, the T3SS-compatible polypeptide is an antigen.

In some embodiments, the antigen is an antigen derived from an enteric pathogen. In one aspect, described herein is a method of treating a proliferative disease in a subject, the method comprising, administering an engineered microbial cell comprising a T3SS-compatible antigen polypeptide to the subject. In some embodiments, the microbial cell is administered orally.

In one aspect, the technology described herein relates to a method of introducing a polypeptide into a target cell, the method comprising contacting the target cell with an engineered microbial cell comprising a T3SS and a T3SS-compatible substrate as described herein.

In the various embodiments described herein, it is further contemplated that variants (naturally occurring or otherwise), alleles, homologs, conservatively modified variants, and/or conservative substitution variants of any of the specific polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe.

Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are also known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In addition to a first nucleic acid sequence comprising genes encoding a functional type three secretion system (T3SS) and a second nucleic acid sequence encoding a T3SS-compatible polypeptide, in some embodiments, the engineered non-pathogenic microbial cells described herein further comprise a third nucleic acid sequence encoding a master T3SS regulator. A master T3SS regulator can induce the expression of one or more components of a functional T3SS system and/or T3SS substrates. This can be desirable in instances where constitutive expression of at least one of polypeptides encoded by the first and second nucleic acid sequences is not desired, e.g. to avoid introducing the T3SS-compatible polypeptide to cells other than the target cell, and/or to avoid high fitness costs associated with constitutive expression of the polypeptides encoded by the first and second nucleic acid sequences.

Conversely, in some systems, e.g. *E. coli*, the polypeptides encoded by the first and second nucleic acid sequences may not be expressed in the absence of a T3SS master regulator. In other words, one typically adds the master regulator to obtain expression of the T3SS system, e.g., in *E. coli*. The lack of this plasmid may result in no expression of the T3SS.

Non-limiting examples of T3SS master regulators include VirB, VirF, and/or homologs thereof. A number of master regulators of T3SS's are known in the art, see, e.g. Fass and Groisman. Current Opinion in Microbiology 2009 12:199-204; which is incorporated by reference herein in its entirety).

In some embodiments, an engineered microbial cell can comprise nucleic acid sequence(s) encoding multiple T3SS-compatible polypeptides. The multiple T3SS-compatible polypeptides can be encoded as part of the same operon and/or as part of separate operons.

In one aspect, described herein is a kit comprising an engineered microbial cell as described herein. In one aspect, described herein is a kit comprising an engineered microbial cell comprising a first nucleic acid sequence comprising genes encoding a functional type three secretion system (T3SS); and a second nucleic acid sequence encoding an T3SS-compatible polypeptide; wherein the engineered microbial cell is non-pathogenic with respect to a target cell.

In some embodiments, the methods described herein relate to treating a subject. Subjects having a condition described here (e.g. inflammation or cancer) can be identified by a physician using current methods of diagnosing such conditions. Symptoms and/or complications which characterize these conditions and aid in diagnosis.

The compositions and methods described herein can be administered to a subject in need of treatment, e.g. in need of treatment for inflammation or cancer. In some embodiments, the methods described herein comprise administering an effective amount of compositions described herein, e.g. engineered microbial cells to a subject in order to alleviate a symptom. As used herein, "alleviating a symptom" is ameliorating any condition or symptom associated with a given condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, subcutaneous, transdermal, airway (aerosol), cutaneous, topical, injection, or intratumoral administration. Administration can be local or systemic.

The term "effective amount" as used herein refers to the amount of engineered microbial cells needed to alleviate at least one or more symptom of the disease or disorder, and relates to a sufficient amount of pharmacological composition to provide the desired effect. The term "therapeutically effective amount" therefore refers to an amount of engineered microbial cells that is sufficient to effect a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an engineered microbial cell which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammation, among others. The dosage can be determined by a physician and adjusted, as necessary, to suit observed effects of the treatment.

In some embodiments, the technology described herein relates to a pharmaceutical composition comprising an engineered microbial cell as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutical compositions comprising an engineered microbial cell can be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

The methods described herein can further comprise administering a second agent and/or treatment to the subject, e.g. as part of a combinatorial therapy.

The methods described herein can further comprise administering a second agent and/or treatment to the subject, e.g. as part of a combinatorial therapy. By way of non-limiting example, if a subject is to be treated for inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

Non-limiting examples of a second agent and/or treatment for a subject in need of treatment for cancer can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In certain embodiments, an effective dose of a composition comprising engineered microbial cells as described herein can be administered to a patient once. In certain embodiments, an effective dose of a composition comprising engineered microbial cells can be administered to a patient repeatedly. In some embodiments, the dose can be a daily administration, for example oral administration, of, e.g., a capsule comprising bacterial cells as described herein. In some embodiments, the dose can be, e.g. an injection of bacterial cells into the desired area, e.g. a tumor. In some embodiments, the dose can be administered systemically, e.g. by intravenous injection. In some embodiments, a dose can comprise from $10^6$ to $10^{12}$ cells. In some embodiments, a dose can comprise from about $10^8$ to $10^{10}$ cells. A composition comprising engineered microbial cells can be administered over a period of time, such as over a 5 minute, 10 minute, 15 minute, 20 minute, or 25 minute period. The administration can be repeated, for example, on a regular basis, such as hourly for 3 hours, 6 hours, 12 hours, daily (i.e. one a day) or longer or such as once a week, or biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to engineered microbial cells. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of engineered microbial cells, according to the methods described herein depend upon, for example, the form of the cells, their potency, and the extent to which symptoms, markers, or indicators of a condition described herein are desired to be reduced, for example the percentage reduction desired. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of engineered microbial cells in, e.g. the treatment of a condition described herein, or to induce a response as described herein can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein. When using an experimental animal model, efficacy of treatment is evidenced when a statistically significant change in a marker is observed.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or more or any decrease of at least 10% as compared to a reference level. In some embodiments, the terms can represent a 100% decrease, i.e. a non-detectable level as compared to a reference level. In the context of a marker or symptom, a "decrease" is a statistically significant decrease in such level. The decrease can be, for example, at least 10%, at least 20%, at least 30%, at least 40% or more, and is preferably down to a level accepted as within the range of normal for an individual without such disorder. In some instances, the symptom can be essentially eliminated which means that the symptom is reduced, i.e. the individual is in at least temporary remission.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or non-human animal. Usually the non-human animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a given condition. A subject can be male or female.

A subject can be one who has been previously diagnosed with or identified as suffering from or having a condition in need of treatment or one or more complications related to such a condition, and optionally, have already undergone treatment. Alternatively, a subject can also be one who has not been previously diagnosed as having a condition or one or more complications related to the condition. For example, a subject can be one who exhibits one or more risk factors or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term “expression” refers to the cellular processes involved in producing RNA and proteins and as appropriate, secreting proteins, including where applicable, but not limited to, for example, transcription, transcript processing, translation and protein folding, modification and processing. “Expression products” include RNA transcribed from a gene, and polypeptides obtained by translation of mRNA transcribed from a gene. The term “gene” means the nucleic acid sequence which is transcribed (DNA) to RNA in vitro or in vivo when operatively linked to appropriate regulatory sequences. A gene may or may not include regions preceding and following the coding region, e.g. 5' untranslated (5'UTR) or “leader” sequences and 3' UTR or “trailer” sequences.

The term “operatively linked” includes having an appropriate start signal (e.g., ATG) in front of the polynucleotide sequence to be expressed, and maintaining the correct reading frame to permit expression of the polynucleotide sequence under the control of the expression control sequence, and, optionally, production of the desired polypeptide encoded by the polynucleotide sequence. In some examples, transcription of a nucleic acid is under the control of a promoter sequence (or other transcriptional regulatory sequence) which controls the expression of the nucleic acid in a cell-type in which expression is intended. It will also be understood that the nucleic acid can be under the control of transcriptional regulatory sequences which are the same or which are different from those sequences which control transcription of the naturally-occurring form of a protein.

The term “isolated” or “partially purified” as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered “isolated.”

The term “reprogramming” as used herein refers to a process that alters or reverses the developmental potential of a cell or population of cells (e.g., a somatic cell). Stated another way, reprogramming refers to a process of driving a cell to a state with higher developmental potential, i.e., backwards to a less differentiated state. The cell to be reprogrammed can be either partially or terminally differentiated prior to reprogramming. In some embodiments of the aspects described herein, reprogramming encompasses a complete or partial reversion of the differentiation state, an increase in the developmental potential of a cell to a cell having a pluripotent state. In some embodiments, reprogramming encompasses driving a somatic cell to a pluripotent state, such that the cell has the developmental potential of an embryonic stem cell, i.e., an embryonic stem cell phenotype. In some embodiments, reprogramming also encompasses a partial reversion of the differentiation state or a partial increase of the developmental potential of a cell, such as a somatic cell or a unipotent cell, to a multipotent state. Reprogramming also encompasses partial reversion of the differentiation state of a cell to a state that renders the cell more susceptible to complete reprogramming to a pluripotent state when subjected to additional manipulations. In certain embodiments, reprogramming of a cell causes the cell to assume a multipotent state (e.g., is a multipotent cell). In some embodiments, reprogramming of a cell (e.g. a somatic cell) causes the cell to assume a pluripotent-like state or an embryonic stem cell phenotype. The resulting cells are referred to herein as “reprogrammed cells.” The term “partially reprogrammed somatic cell” as referred to herein refers to a cell which has been reprogrammed from a cell with lower developmental potential by the methods as disclosed herein, wherein the partially reprogrammed cell has not been completely reprogrammed to a pluripotent state but rather to a non-pluripotent, stable intermediate state. Such a partially reprogrammed cell can have a developmental potential lower that of a pluripotent cell, but higher than a multipotent cell. A partially reprogrammed cell can, for example, differentiate into one or two of the three germ layers, but cannot differentiate into all three of the germ layers.

The term a “reprogramming factor,” as used herein, refers to a polypeptide, the expression of which contributes to the reprogramming of a cell, e.g. a somatic cell, to a less differentiated or undifferentiated state, e.g. to a cell of a pluripotent state or partially pluripotent state. A reprogramming factor can be, for example, transcription factors that can reprogram cells to a pluripotent state, such as SOX2, OCT3/4, KLF4, NANOG, LIN-28, c-MYC, and the like, including as any gene, protein, RNA or small molecule, that can substitute for one or more of these in a method of reprogramming cells in vitro.

As used herein, the term “transdifferentiation” refers to the differentiation of one cell type to another cell type, preferably, in one step; thus a method that modifies the differentiated phenotype or developmental potential of a cell without the formation of a pluripotent intermediate cell; i.e. does not require that the cell be first dedifferentiated (or reprogrammed) and then differentiated to another cell type. Instead, the cell type is merely “switched” from one cell type to another without going through a less differentiated phenotype.

As used herein, the terms “treat,” “treatment,” “treating,” or “amelioration” refer to therapeutic treatments, wherein the object is to reverse, alleviate, ameliorate, inhibit, slow down or stop the progression or severity of a condition associated with a disease or disorder, e.g. cancer or inflammation. The term “treating” includes reducing or alleviating at least one adverse effect or symptom of a condition, disease or disorder. Treatment is generally “effective” if one or more symptoms or clinical markers are reduced. Alternatively, treatment is “effective” if the progression of a disease is reduced or halted. That is, “treatment” includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An engineered non-pathogenic microbial cell comprising:
   a first nucleic acid sequence comprising genes encoding a functional type three secretion system (T3SS);
   a second nucleic acid sequence encoding an T3SS-compatible polypeptide;
   wherein the engineered microbial cell is non-pathogenic with respect to the target cell or target organism.
2. The engineered microbial cell of paragraph 1, wherein the T3SS-compatible polypeptide is exogenous to the microbial cell.
3. The engineered microbial cell of any of paragraphs 1-2, wherein the T3SS-compatible polypeptide is ectopic with respect to the target cell.
4. The engineered microbial cell of any of paragraphs 1-3, wherein the cell comprises a third nucleic acid sequence encoding a master T3SS regulator.
5. The engineered microbial cell of any of paragraphs 1-4, wherein the master T3SS regulator is selected from the group consisting of:
   VirB and VirF.
6. The engineered microbial cell of any of paragraphs 1-5, wherein the genes encoding a functional type three secretion system (T3SS) comprise one or more of:
   virB; acp; ipaA; ipaB; ipaC; ipaD; ipgC; ipgB1; ipgA; icsB; ipgD; ipgE; ipgF; mxiG;
   mxiH; mxiI; mxiJ; mxiK; mxiN; mxiL; mxiM; mxiE; mxiD; mxiC; mxiA; spa15;
   spa47; spa13; spa32; spa33; spa24; spa9; spa29; and spa40.
7. The engineered microbial cell of paragraph 6, wherein the type three secretion system (T3SS) comprises polypeptides endogenous to a bacterium selected from the group consisting of:
   *Shigella* spp; *Salmonella* spp; enteropathogenic *E. coli*; and *Yersinia* spp.
8. The engineered microbial cell of any of paragraphs 1-7, wherein the first nucleic acid sequence is located on a plasmid.
9. The engineered microbial cell of any of paragraphs 1-7, wherein the first nucleic acid sequence is located on a chromosome.
10. The engineered microbial cell of any of paragraphs 1-9, wherein the non-pathogenic organism is selected from the group consisting of:
   *E. coli* NISSLE 1917 (EcN); *E. coli* K12; and derivative strains.
11. The engineered microbial cell of paragraph 10, wherein the strain which is derivative of *E. coli* K12 is selected from the group consisting of:
   *E. coli* DH10β and *E. coli* DH5α.
12. The engineered microbial cell of any of paragraphs 1-9, wherein the non-pathogenic organism is engineered by deletion or mutation of one or more T3SS components.
13. The engineered microbial cell of paragraph 12, wherein the one or more T3SS components is selected from the group consisting of:
   a toxin; a T3SS effector; a structural T3SS polypeptide; and a master regulator of T3SS components.
14. The engineered microbial cell of any of paragraphs 12-13, wherein the T3SS component is located on a plasmid.
15. The engineered microbial cell of any of paragraphs 12-14, wherein the pathogenic microbial cell is selected from the group consisting of:
   *Salmonella* spp.; *Shigella* Spp; and *Yersinia* spp.
16. The engineered microbial cell of paragraph 15, wherein the pathogenic microbial cell is selected from the group consisting of:
   *Salmonella typhimurium* SPI1 and *Shigella flexneri* mxi-spa.
17. The engineered microbial cell of any of paragraphs 1-16, wherein the cell comprises genes encoding IpgB1; IpgD; IpaA; and IcsB or homologs thereof
18. The engineered microbial cell of any of paragraphs 1-16, wherein the cell comprises genes encoding no more than three T3SS secreted polypeptides selected from the group consisting of:
   IpgB1; IpgD; IpaA; and IcsB or homologs thereof
19. The engineered microbial cell paragraph 18, wherein the cell does not comprise genes encoding IpgB1; IpgD; IpaA; and IcsB or homologs thereof
20. The engineered microbial cell of any of paragraphs 1-19, wherein the cell further comprises a nucleic acid sequence encoding one or more polypeptides that increase adhesion to the target cell.
21. The engineered microbial cell of paragraph 20, wherein the polypeptides that increase adhesion to the target cell comprise Tir and intimin.
22. The engineered microbial cell of paragraph 21, wherein the polypeptide that increases adhesion to the target cell is selected from a group consisting of:
   a bacterial adhesion; Afa1; AIDA; invasion; or a single chain antibody specific for an extracellular epitope of a target cell polypeptide.
23. The engineered microbial cell of any of paragraphs 1-22, wherein the polypeptide comprises an N-terminal type three secretion system (T3SS) signal.
24. The engineered microbial cell of any of paragraphs 1-23, wherein the nucleic acid sequence encoding the polypeptide is operatively linked to a type three secretion system (T3SS)-associated promoter or promoter element.
25. The engineered microbial cell of paragraph 24, wherein the type three secretion system (T3SS)-associated promoter or promoter element is selected from the group consisting of:
   MxiE recognition sequences; and an inducible promoter.
26. The engineered microbial cell of any of paragraphs 1-25, wherein the nucleic acid encoding the polypeptide is operatively linked to an inducible promoter.
27. The engineered microbial cell of any of paragraphs 1-26, wherein the nucleic acid encoding the polypeptide is located on a chromosome.
28. The engineered microbial cell of any of paragraphs 1-27, wherein the polypeptide is an anti-inflammatory polypeptide.
29. The engineered microbial cell of paragraph 28, wherein the anti-inflammatory polypeptide is selected from the group consisting of:

a bacterial anti-inflammatory polypeptide; a bacterial polypeptide that inhibits NF-κB signaling; OspG; OspF; IpaH9.8; SseL; YopJ; NleB; NleC; NleE; NleH1; OspL.

30. The engineered microbial cell of any of paragraphs 28-29, wherein the non-pathogenic microbial cell is a commensal intestinal microbial cell.

31. The engineered microbial cell of any of paragraphs 28-30, wherein the commensal intestinal microbial cell is *E. coli* NISSLE 1917 (EcN).

32. The engineered microbial cell of any of paragraphs 1-27, wherein the type three secretion system (T3SS)-compatible polypeptide is a toxin.

33. The engineered microbial cell of any of paragraphs 1-27, wherein the type three secretion system (T3SS)-compatible polypeptide is a tumor suppressor polypeptide.

34. The engineered microbial cell of any of paragraphs 1-27, wherein the type three secretion system (T3SS)-compatible polypeptide is a reprogramming factor.

35. The engineered microbial cell of paragraph 34, wherein the reprogramming factor is selected from the group consisting of:

Oct3/4; Sox2; Klf4; c-Myc; Lin28; Nanog; Sa14; Dppa2; Ezh2; and Esrrb.

36. The engineered microbial cell of any of paragraphs 1-27, wherein the type three secretion system (T3SS)-compatible polypeptide is a transdifferentiation factor.

37. The engineered microbial cell of paragraph 36, wherein the transdifferentiation factor is a myocyte transdifferentiation factor selected from the group consisting of:

myoD.

38. The engineered microbial cell of paragraph 36, wherein the transdifferentiation factor is a cardiomyocyte transdifferentiation factor selected from the group consisting of:

Gata4; Mec2F; and Tbs5.

39. The engineered microbial cell of any of paragraphs 1-27, wherein the type three secretion system (T3SS)-compatible polypeptide is an antigen.

40. The engineered microbial cell of paragraph 39, wherein the antigen is derived from an enteric pathogen.

41. A method of introducing a polypeptide into a target cell, the method comprising contacting the target cell with an engineered microbial cell of any of paragraphs 1-40.

42. A method of reducing inflammation in a subject, the method comprising administering an engineered microbial cell of any of paragraphs 28-31 to the subject.

43. The method of paragraph 42, wherein the subject is in need of treatment for an auto-immune disease.

44. The method of paragraph 42, wherein the inflammation is inflammation of the gastrointestinal tract.

45. The method of any of paragraphs 42-44, wherein the subject is in need of treatment for a condition selected from the group consisting of:

asthma; inflammatory bowel disease; Crohn's disease; obesity; and ulcerative colitis.

46. The method of any of paragraphs 42-45, wherein the engineered microbial cell is administered orally.

47. A method of treating a proliferative disease in a subject, the method comprising, administering an engineered microbial cell of any of paragraphs 32-33 to the subject.

48. The method of paragraph 47, wherein the proliferative disease is cancer.

49. The method of paragraph 48, wherein the cancer is a cancer of the gastrointestinal tract and the microbial cell is administered orally.

50. A method of treating a proliferative disease in a subject, the method comprising, administering an engineered microbial cell of any of paragraphs 39-40 to the subject.

51. The method of paragraph 50, wherein the microbial cell is administered orally.

52. A method of reprogramming/transdifferentiating a target cell or increasing the efficiency of the reprogramming/transdiffereniation of a target cell, the method comprising contacting the cell with an engineered microbial cell of any of paragraphs 34-38.

53. The method of paragraph 52, wherein the method further comprises the steps of:

a) contacting the target cell and engineered microbial cell with an antibiotic;

b) removing unattached microbial cells and the antibiotic; and c) contacting the target cell with a second engineered microbial cell.

54. The method of paragraph 53, wherein steps a-c are repeated at least once.

55. The method of any of paragraphs 52-54, wherein the target cell is contacted with an engineered microbial cell at least daily for a period of at least 5 days.

56. The method of any of paragraphs 52-55, whereby the target cell is a cell which is reprogrammed to an induced pluripotent stem cell (iPSC) phenotype.

57. The method of any of paragraphs 52-55, whereby the target cell is a cell which is transdifferentiated.

58. A kit comprising the engineered microbial cell of any of paragraphs 1-40.

59. A kit comprising:

an engineered microbial cell comprising a first nucleic acid sequence comprising genes encoding a functional type three secretion system (T3SS); and a second nucleic acid sequence encoding an T3SS-compatible polypeptide which is exogenous to a target cell;

wherein the engineered microbial cell is non-pathogenic with respect to the target cell.

60. The use of an engineered microbial cell of any of paragraphs 23-31 or 39-40 to reduce inflammation, comprising administering the cell to a subject in need of reduction of inflammation.

61. The use of paragraph 60, wherein the subject is in need of treatment for an auto-immune disease.

62. The use of paragraph 60, wherein the inflammation is inflammation of the gastrointestinal tract.

63. The use of any of paragraphs 60-62, wherein the subject is in need of treatment for a condition selected from the group consisting of:

asthma; inflammatory bowel disease; Crohn's disease; obesity; and ulcerative colitis.

64. The use of any of paragraphs 60-63, wherein the engineered microbial cell is administered orally.

65. The use of an engineered microbial cell of any of paragraphs 32-33 or 39-40 to reduce treat a proliferative disease, comprising administering the cell to a subject in need of treatment for a proliferative disease.

66. The use of paragraph 65, wherein the proliferative disease is cancer.

67. The use of paragraph 66, wherein the cancer is a cancer of the gastrointestinal tract and the microbial cell is administered orally.

EXAMPLES

Example 1

Described herein is the introduction of a specialized type 3 secretion system capable of delivering proteins directly from bacteria into mammalian cells into non-pathogenic laboratory and commensal strains of *E. coli*, which are then engineered to deliver defined therapeutic molecules rather than virulence proteins into eukaryotic cells. Also described herein is the development of: *E. coli* strains capable of delivering reprogramming factors into mammalian cells in order to generate viral free induced pluripotent stem cells; *E. coli* strains capable of delivery of reprogramming factors into mammalian cells in order to generate viral transdifferentiated cells, i.e. the reprogramming of fibroblasts into muscle cells via MyoD delivery; commensal *E. coli* strains that deliver anti-inflammatory promoting proteins (ones that are normal substrates of the secretion systems of pathogenic bacteria) into host cells in vivo as a potential treatment for autoimmune diseases including inflammatory bowel disease; commensal *E. coli* strains that deliver toxic proteins to tumors; commensal *E. coli* strains that deliver tumor suppressor proteins to tumor cells; commensal *E. coli* strains that deliver defined eukaryotic proteins into mammalian cells.

The technology described herein relates to the introduction of all of the genes required to make a functional transkingdom secretion system (e.g. from *Shigella*) into laboratory and commensal strains of *E. coli*. No commensal bacteria have previously been identified or engineered to encode such a secretion system. The compositions described herein can be applied in the following ways:

- iPS/transdifferentiation strains: development of viral-free reprogrammed cells using an inexpensive, efficient and safe delivery mechanism (bacteria)
- anti-inflammatory promoting bacteria: ability to target down-regulation of inappropriate inflammatory responses to sites of disease which should alleviate many of the side effects observed with the use of systemic immunosuppressive drugs.
- anti-tumor bacteria: ability to deliver toxic proteins or tumor suppressor proteins into cancer cells to slow or stop the growth of tumors.
- new inexpensive viral-free means to generate induced pluripotent stem cells and transdifferentiated cells, which can be used for cell therapy or for drug discovery.
- modified commensal bacteria that can be given orally to patients for the treatment of a variety of diseases including inflammatory bowel disease and cancer.

Example 2

A hallmark of the pathogenesis of inflammatory bowel disease (IBD) is dysregulation of cytokine production by intestinal cells, including lymphocytes, macrophages, epithelial and dendritic cells. Each of these cell types exhibits inappropriate activation of NF-κB resulting in the production of pro-inflammatory cytokines. There is evidence that the amount of activated NF-κB parallels the severity of intestinal inflammation and a major breakthrough in the treatment of IBD has been the use of antibodies directed against TNFα, presumably by limiting much of the signaling that results in activation of NF-κB. This intervention has dramatically improved the symptoms, disease course and quality of life of patients with IBD (1). However, the systemic immunosuppression associated with the use of these agents greatly increases the susceptibility of these patients for developing serious infectious diseases like reactivation of latent tuberculosis, the development of brain abscess and disseminated fungal diseases. This methods and compositions described herein provide a microbe-based approach to treat IBD, which would limit immunosuppression to the main site of disease, the intestines. Specifically, described herein is the generation of commensal *E. coli* strains capable of delivering bacterial proteins that inhibit NF-κB activation directly into intestinal cells and the testing of whether these strains can act, at least transiently, to suppress intestinal inflammation in an experimental model of spontaneous colitis. The methods and compositions described herein are a powerful new therapeutic paradigm for the treatment of IBD that can circumvent issues associated with systemic immunosuppression.

IBD and Innate Immunity.

The innate immune system is a surveillance system that serves as the host's first line of defense in recognizing foreign molecules that signal the beginnings of an infection. This response is triggered when the host senses microbial-associated molecular patterns (MAMPs) like lipopolysaccharide and peptidoglycan. These MAMPs are recognized by TLR (Toll-like receptors) and NOD receptors, which then activate downstream signaling cascades that result in the expression of cytokines. These cytokines act to establish the inflammatory response including the recruitment of neutrophils and macrophages to sites of infection. The innate immune response initiates the activation of the humoral and cellular immune systems. In the context of IBD, each of these cell types exhibits inappropriate activation of the transcription factor NF-κB. Interestingly, the amount of activated NF-κB has been linked to the severity of intestinal inflammation (2). Local administration of antisense oligonucleotides directed at p65, one of the subunits of NF-κB, has been demonstrated to markedly decrease inflammation in an experimental mouse model of IBD (3). These observations suggest that targeted therapies that block NF-κB are likely to prove to be effective treatments for IBD.

Targeted Inhibition of NF-κB Activation by Pathogenic Bacterial Proteins.

Bacterial pathogens have evolved numerous mechanisms to suppress or combat host responses. For example, many Gram-negative intestinal pathogens including *Salmonella*, *Shigella*, enteropathogenic *E. coli* and *Yersinia* species utilize specialized type 3 secretion systems to directly inject tens of proteins (effectors) into eukaryotic host cells. These secretion systems are complex machines composed of 20-25 proteins that span both the inner and outer bacteria membranes that forms a needle capped by pore-forming proteins that insert into host cell membrane essentially forming a channel for the deliver of bacterial proteins into host cells. While the components of the T3SSs are highly conserved, each bacterium injects its own unique set of effectors into host cells. Interestingly, over the past several years multiple effectors that inhibit signaling pathways that lead to inhibition of NF-κB activation have been identified. As summarized in Table 1, these effectors target a variety of steps required for the activation of NF-κB.

TABLE 1

Summary of effectors currently known to inhibit NF-κB signaling

| organism | effector | mechanism |
|---|---|---|
| *Shigella* | OspG | binds E2 ubiquitin ligase inhibiting IκB ubiquitination and degradation |
| | OspF | phosphothreonine lyase; epigenetic modifications of histones involved in NF-κB access to promotors |
| | IpaH9.8 | E3 ubiquitin ligase; targets NEMO for ubiquitination and degradation |
| *Salmonella* | SseL | deubiquitinase; inhibits ubiquitination and degradation |
| *Yersinia* | YopJ | acetyltransferase; inactivates IκKα |
| *E. coli* | NleB | unknown mechanism; blocks TNFα signaling upstream of TAK1 complex |
| | NleC | metalloprotease; cleaves RelA |
| | NleE | Inhibits IκKβ activation |
| | NleH1 | Inhibits interaction of NF-κB with some promoters |

Generation of Laboratory Strains Type 3 Competent *E. coli.*

In the case of *Shigella*, all of the genes encoding the 20-25 proteins required to form a functional T3SS are encoded within two large adjacent operons located on a virulence plasmid [26]. Through a series of homologous-recombination based approaches [33, 34], this entire 31 kb region was captured onto a smaller, autonomously replicating plasmid. The introduction of this plasmid into laboratory strains of *E. coli* (DH10B) and BL21 is sufficient to generate strains capable of secreting *Shigella* effectors into the media as well as delivering the effectors directly into host cells. Notably, by specifically capturing this region of the virulence plasmid that encodes the type 3 secretion machinery, the genes encoding >20 effectors are encoded elsewhere on the *Shigella* virulence plasmid are not introduced into the *E. coli* strains. Thus, these type 3 secretion competent *E. coli* strains are non-pathogenic, as the few organisms that invade host cells do not replicate and are confined to the phagosome. In addition, human cells infected with these strains demonstrate no IL-8 secretion, indicating that a non-immunogenic delivery strain has been generated.

Recognition of Heterologous Effectors Via the *Shigella* T3SS.

Experiments have demonstrated that the *Shigella* T3SS recognizes and secrets effectors from *Salmonella, Yersinia* and enteropathogenic *E. coli.*

Development of Anti-Inflammatory Promoting Strains of Commensal *E. coli.*

NISSLE 1917 strains capable of secreting anti-inflammatory effectors can be generated. Currently, despite extensive sequencing efforts, no bacterial species present in the mammalian microbiota has been identified to encode a T3SS (or any other higher order bacterial secretion system, i.e. one capable of delivery multiple proteins into host cells). The generation of such a strain de novo by introducing the plasmid carrying the *Shigella* T3SS into the commensal human *E. coli* NISSLE 1917 strain (EcN), a strain previously demonstrated to be a safe and effective vehicle for delivering therapeutic molecules to the mouse intestines (4) is described herein. The ability of this strain to secrete each of the 9 anti-inflammatory effectors described in Table 1 into the media as well as directly into host cells can be tested by using quantitative immunoblot assays to determine the amount of each effector to be secreted into the media as well as directly delivered into host cells when FLAG-tagged. In the unlikely case that one of the heterologous effectors is not recognized by the *Shigella* type 3 secretion system (which can be introduced into EcN), their N-termini can be replaced with the N-termini of a *Shigella* effector.

Determine the Ability of Commensal Anti-Inflammatory Promoting *E. coli* Strains to Inhibit NF-κB Signaling and the Production of Pro-Inflammatory Cytokines.

The ability of type 3 secretion competent EcN strains that secrete each of the nine effectors listed in Table 1 to inhibit NF-κB activation can be compared using two complementary approaches. This will be the first time that the individual roles of single effectors in suppressing innate immune responses will be studied. First, the levels of IL-8 present in the supernatants of polarized intestinal (Caco-2) epithelial cells infected with the 9 type 3 competent EcN strains after exposure to TNFα can be compared. Supernatants of infected and uninfected cells can be collected for 24 hours and IL-8 levels determined using a commercially available IL-8 ELISA kit (BD Scientific). These results can be confirmed by measuring IL-8 mRNA levels by qPCR using gene specific primers. Second, the ability of the nine type 3 competent EcN strains to inhibit NF-κB activation using a firefly luciferase reporter assay. Given the technically difficulties associated with the introduction of plasmids into Caco-2 cells, in this case, highly transfectable HEK293 cells can be used. Twenty-four hours after introducing NF-κB luciferase and constitutive renilla reporter plasmids into HEK293 cells, the cells can be infected with each of the 9 anti-inflammatory promoting EcN strains. After one hour, TNFα can be added to the media to induce signaling pathways that lead to NF-κB activation. The ability of each strain to inhibit NF-κB activation can be compared by monitoring luciferase activity over time using the commercially available Dual-Glo Luciferase Reporter Assay kit (Promega). Renilla levels will be measured to account for potential issues with transfection efficiency and/or cell viability.

Identify Effectors that Act Additively or Synergistically to Inhibit NF-κB Signaling.

The experiments described above can provide the first side-by-side comparison of the ability of single type 3 effectors to inhibit NF-κB activation. However, for the treatment of IBD, a strain that delivers multiple effectors into host cells can be generated, as presumably the effectors will work additively or perhaps even synergistically to inhibit NF-κB activation. To identify such effectors, the levels of IL-8 secreted when Caco-2 cells infected with type 3 competent EcN strains that inject each of the potential 72 effector pairs in host cells are exposed to TNFα can be compared. For these studies, rather than introducing two effectors into the same EcN strain, the Caco-2 cells can be infected with a 1:1 mixture of the two strains at experimentally determined multiplicity of infection (MOI) to ensure that both effectors will be injected into the cells at similar levels. Based on these results and the information regarding the sites of action of each effector (Table 1), more complex combinations of effectors can be examined to test for synergy. Rational criteria will be used as opposed to testing all possible combinations, which would entail over 3,000 potential combinations. A combination of up to 4 effectors that results in the most significant and consistent inhibition of IL-8 production when the strains are infected at the lowest overall multiplicity of infection can be identified.

Generate Strains of Commensal *E. coli* with Stably Integrated Anti-Inflammatory Effectors that are Co-Regulated with the *Shigella* T3SS.

For initial in vitro applications, the genes encoding the anti-inflammatory promoting effectors can be carried on a low copy number plasmid expressed via an IPTG-regulatable promotor. However, for mouse studies, strains where genes encoding the anti-inflammatory effectors are present on the EcN chromosome under control of MxiE, a transcription factor that regulates the expression of at least 12 *Shigella* effectors can be generated. The transcriptional start sites of eight MxiE-regulated genes have been mapped (5). This information can guide the choice of sequences to place upstream of the anti-inflammatory effectors to ensure that they are coordinately transcribed at the correct time.

Described herein is the generation of a type 3 competent EcN strain that delivers up to 4 anti-inflammatory promoting effectors into host cells and acts to effectively inhibit NF-κB activation when cells are exposed to TNFα.

Evaluate Whether Anti-Inflammatory Promoting EcN Strains are Capable of Suppressing Inflammation in a Mouse Model of IBD.

Described herein are experiments which determine whether the anti-inflammatory promoting EcN stain described above herein is capable of suppressing intestinal inflammation in a mouse model of IBD. Wild type EcN has already been established to be safe in humans and in clinical trials is as effective as 5-ASA (an oral anti-inflammatory intestinal agent) in maintaining a state of remission when administered daily to patients with IBD (6). There is also evidence that EcN is capable of persistently colonizing the intestines of mice for at least two weeks after being administered orally for 3 days (7) as well as for at least 40 days after a single oral dose along with a single dose of ampicillin (4). However, EcN has not yet been demonstrated to suppress colitis flares in humans or mice. There are many animal models for studying IBD. In the experiments described herein the TRUC (T-bet−/−×Rag2−/− ulcerative colitis) model is used. These mice develop a spontaneous, highly penetrant, and communicable colitis that 1) is detectable histologically by 3.5 weeks of age, 2) resembles human ulcerative colitis and 3) is associated with altered colonic barrier function and elevated TNFα (8).

Determine Whether and where the Anti-Inflammatory Strains are Capable of Colonizing the Intestines.

The ability of "wild type" EcN, and T3 secretion competent anti-inflammatory promoting EcN to colonize normal and inflamed intestines can be compared. Colonization can be measured by quantifying the shedding of EcN in stool and by tissue examination upon sacrifice. To facilitate visualization of the EcN, versions of each strain that stably express eGFP can be generated. On post-natal day 21, wild type and TRUC mice can be given an oral inoculum [1-2×109 colony forming units (CFU)] for three consecutive days. Over the following 30-day period, individual mice (n=5 per strain) can be evaluated by both daily fecal sampling and by tissue examination upon sacrifice (1 mouse/strain genotype on d7, d14, d21, d28 post inoculum) for evidence of the eGFP expressing *E. coli* along the mucosal and across the bowel wall. In order to favor the detection of the commensal *E. coli* in the fecal pellets, the bacteria can be plated on MacConkey's media that enriches for Enterobacteriaceae and facilitate visualization of fluorescence bacteria by exposure to UV light and/or direct measurement of eGFP by qPCR. Tissues can be evaluated for eGFP signal using freshly mounted small and large intestinal tissue samples. Tissues can also be fixed, embedded, and stained with anti-eGFP antibodies for further analysis of colonization pattern. Mesenteric lymph nodes can also be sampled and analyzed to qPCR for detection of the strains using EcN specific primers (9). Whether daily administration permits the strains to adhere to regions of the intestines can also be determined.

Determine Whether Anti-Inflammatory Promoting Effectors are Delivered Via EcN into Intestinal Cells.

In order to identify the cell types targeted by the type 3 competent EcN strain, an in vivo based assay that has been successfully used to identify intestinal cell types targeted by the *Yersinia* and *Salmonella* type 3 secretion systems (10) can be used. In this assay, bacterial strains that express a type 3 secreted form of the TEM-1 are used. TEM-1 is a beta-lactamase whose activity inside mammalian cells can be monitored via a fluorescence-based assay. Wild type and TRUC mice can be orally inoculated as described above with the anti-inflammatory promoting EcN strain, which in addition to the anti-inflammatory promoting effectors expresses a version of TEM-1 that is recognized as a type III secreted substrate. Over the following 4 weeks, 2-3 mice can be sacrificed at weekly intervals to identify cells targeted by the EcN strain. Epithelial cell preparations and single cell suspensions enriched for immunocytes can be generated from small intestine and colon using well-established protocols. Cells can then be incubated with CCF2-AM, a FRET reporter of TEM-1 activity. If the type 3 secreted TEM-1 protein is delivered into the cells, the CCF2-AM will be cleaved such that its fluorescence changes from green (520 nm) to blue (450 nm). Cells can then be analyzed by flow cytometry to identify the subsets expressing the green (520 nm) vs. blue (450 nm) emission spectra. Cells from tissues of mice that were inoculated with the unaltered *E. coli* strain can be used as negative controls.

It is possible that the anti-inflammatory promoting EcN strain will colonize the intestines, but not stably adhere to the intestinal cells such that the type 3 secretion system is engaged is able to efficiently inject effectors into the host cells. Two modifications can be made to the strain to increase its ability to adhere to intestinal cells. First, a version of the type 3 competent EcN strain that forms stable contacts with the host cells can be generated by adapting a strategy from enteropathogenic *E. coli*, an enteric pathogen. Enteropathogenic *E. coli* use the Tir/intimin system to support their attachment to intestinal epithelial cells. Intimin is an outer membrane bacterial protein while Tir is a substrate of the *E. coli* T3SS. Once Tir is delivered into host cells by the T3SS, it integrates into the mammalian plasma membrane and serves as the receptor for intimin. Tir has already been demonstrated to be recognized as a substrate of a heterologous type III secretion system, as long as it was co-expressed with its cognate chaperone, CesT (11). Intimin is an autotransporter and as such is classified as a type V secreted protein. It is highly likely that intimin will be expressed and correctly targeted to the outer membrane of the *E. coli* as it has recently been demonstrated that autotransporters from a variety of bacterium are correctly targeted to the outer membrane when expressed in *E. coli* (12). Second, the utility of introducing a bacterial adhesin from uropathogenic *E. coli*, AfaI, into the type 3 competent EcN strains can be investigated. At least in vitro, the presence of this adhesin greatly increases the ability of *Shigella* to adhere to a variety of cell types.

Test the Effects of the Strains on the Inflammatory Milieu.

Based on inoculation conditions determined in the experiments described above herein, 3-week-old TRUC mice can be inoculated with "wild type" and anti-inflammatory promoting EcN strains. The inflammatory milieu of the intestines can be determined after two and four weeks using three complementary assays. First, the overall effects on inflammation can be determined by directly examined intestinal tissues that are fixed and paraffin embedded for histology-based assessment of intestinal inflammation (13). Second, in order to monitor for specific changes in the cytokine present in the inflammatory milieu of the treated mice, the distal colon of T-bet−/−×Rag2−/− mice can be isolated (14) and explant supernatants analyzed using the Luminex platform to analyze IL-1α, IL-1β IL-2, IL-4, IL-6, KC, TNF-α, IFNγ, IL-10, IL-12p40, IL-12p70, IL-13, IL-17A, IL-21, and IL-23 levels. And, third, flow cytometry based experiments can be performed on mice to quantify different cell types present in the intestines in the presence of the two different EcN strains.

Described herein is the generation of type 3 competent EcN strains capable of delivering anti-inflammatory promoting effectors into mammalian cells and the establishment of whether these strains can suppress intestinal inflammation of TRUC mice. Future studies can be directed towards optimizing this system, for example, systematically screens for more complex combinations of anti-inflammatory promoting effectors that synergistically act to inhibit NF-κB activation and investigation of the utility of introducing other bacterial adhesins into the type 3 competent strains to promote or potentially direct the delivery of effectors into specific cell types. The efficacy of using anti-inflammatory bacteria in other animal models of IBD including the DSS and IL-10−/− models can be investigated, as well as possible long-term sequelae associated with the presence of anti-inflammatory promoting bacteria particularly as inhibition of NF-κB activity can be associated with delays in intestinal healing. The utility of transient versus persistent colonization of the anti-inflammatory promoting strain in preventing and treating IBD flares as well as means to control when the type 3 secretion system of the commensal EcN is expressed can be investigated i.e., it was recently demonstrated that it is possible to remotely control expression of genes under the control of arabinose or tetracycline inducible promotors of EcN present in the intestines of mice by orally introducing inducers (15).

REFERENCES

1. P. Rutgeerts et al., N Engl J Med 353, 2462 (Dec. 8, 2005).
2. G. Rogler et al., Gastroenterology 115, 357 (August, 1998).
3. S. Fichtner-Feigl, I. J. Fuss, J. C. Preiss, W. Strober, A. Kitani, J Clin Invest 115, 3057 (November, 2005).
4. A. M. Westendorf et al., FEMS Immunol Med Microbiol 43, 373 (Mar. 1, 2005).
5. M. Mavris, P. J. Sansonetti, C. Parsot, J Bacteriol 184, 6751 (December, 2002).
6. W. Kruis et al., Gut 53, 1617 (November, 2004).
7. A. M. Petersen, S. Schjorring, S. C. Gerstrom, K. A. Krogfelt, PLoS One 6, e22823.
8. W. S. Garrett et al., Cell 131, 33 (Oct. 5, 2007).
9. L. Grozdanov et al., J Bacteriol 186, 5432 (August, 2004).
10. K. Geddes, F. Cruz, F. Heffron, PLoS Pathog 3, e196 (December, 2007).
11. B. Kenny, J. Warawa, Infect Immun 69, 1444 (March, 2001).
12. S. Jain et al., J Bacteriol 188, 4841 (July, 2006).
13. M. F. Neurath et al., J Exp Med 195, 1129 (May 6, 2002).
14. R. A. Hegazi et al., J Exp Med 202, 1703 (Dec. 19, 2005).
15. H. Loessner et al., Microbes Infect 11, 1097 (December, 2009).

Example 3—Transdifferentiation By Bacterial Mediated Myod Protein Delivery

Forced exogenous gene expression has been well characterized as an effective method for directing both cellular differentiation and dedifferentiation. However, transgene expression is not amenable for therapeutic application due to the potential for insertional mutagenesis. Protein based techniques provide a safe alternative, but current protein delivery methods are quite limited by labor-intensive purification processes, low protein yield and inefficient intracellular targeting. Such limitations can be overcome by using a naturally occurring bacterial protein injection system as described herein.

*Pseudomonas aeruginosa* utilizes a Type III Secretion System to inject bacterial proteins directly into the eukaryotic cell cytoplasm. The inventors have demonstrated the ability of this system to easily deliver a high quantity of protein to both differentiated and pluripotent cells using a genetically attenuated strain. Utilizing Cre recombinase as a reporter, high frequency LoxP mediated recombination in the chromosome of the recipient cells has been demonstrated, suggesting the protein is not only efficiently targeted to the nucleus, but also retains its biological function.

MyoD is a key muscle regulatory factor, the over-expression of which is able to induce transdifferentiation of numerous cell types, such as fibroblasts, into functional myocytes. It is demonstrated herein that transient injection of MyoD protein by *P. aeruginosa* is sufficient to induce myogenic conversion of mouse embryonic fibroblasts. In addition to clear morphological changes, muscle speCific gene expression has been observed by immunostaining, as well as RT-PCR. These studies serve as a foundation for the bacterial delivery of transcription factors to efficiently modulate concentration-dependent and temporal activation of gene expression to direct cell fate without jeopardizing genonic integrity.

Example 4

Embryonic stem (ES) cells are embryo-derived pluripotent cell lines that can give rise to each and every cell type in the body. As such, these cells are invaluable tools for research into the mechanisms of tissue formation and the development of disease, and provide a promising source of "replacement cells" for tissue repair. However, research with embryo-derived ES cells, particularly with respect to their use as disease models or transplantable replacement cells, has been hampered by regulatory hurdles impeding the derivation of new lines and by difficulties in obtaining "patient-specific", histocompatible cells. Exciting recent discoveries enabling direct "reprogramming" of adult somatic cells to ES-like "induced pluripotent (iPS) cells" appear to have lowered these hurdles, providing a facile mechanism for the production of patient-specific pluripotent cells for research and therapy. The revolutionarily development of iPS technology has opened many new opportunities; perhaps the most exciting potential application being the use of patient-specific tissues for transplantation.

However, currently the most efficient ways to reprogram somatic cells involve the introduction of cDNAs that encode four mammalian transcription factors into somatic cells via retroviral vectors. There is great concern regarding the safety of returning these manipulate cells to patients given the risk that virus-mediated insertional events can activate oncogenes or inactive tumor suppressors thus raising concern for the tumorigenicity of the reprogrammed cells. Thus, described herein is the development of a new system to circumvent the issues associated with virally-generated iPS cells by reengineering specialized bacterial transkingdom secretion systems to deliver the iPS transforming proteins, rather than virulence proteins, directly into mammalian cells. This represents a major advance in somatic reprogramming and can have tremendous impact on accelerating the delivery of iPS-based transplant therapies to patients as well as provide a new means of potentially increasing the efficiency of the generation of iPS cells.

A major breakthrough in stem cell biology has emerged with the demonstration that differentiated somatic cells can be converted to pluripotent cells through the introduction of cDNAs into cells. These approaches hold tremendous potential for the patient-specific replacement based cell therapies, however currently a major roadblock in introducing replacement cells into patients is the possibility that the integration of DNA into the chromosomes of these cells can induce tumor formation. To circumvent this major roadblock in moving towards patient-specific therapies, described herein is a technology using re-engineered transkingdom bacterial secretion systems to directly introduce reprogramming proteins rather than the cDNAs that encode them into the differentiated cells.

Embryonic stem (ES) cells are embryo-derived pluripotent cell lines that can give rise to each and every cell type in the body. As such, these cells are invaluable tools for research into the mechanisms of tissue formation and the development of disease, and provide a promising source of "replacement cells" for tissue repair. However, research with embryo-derived ES cells, particularly with respect to their use as disease models or transplantable replacement cells, has been hampered by regulatory hurdles impeding the derivation of new lines and by difficulties in obtaining "patient-specific", histocompatible cells. Exciting recent discoveries enabling direct "reprogramming" of adult somatic cells to ES-like "induced pluripotent (iPS) cells" appear to have lowered these hurdles, providing a facile mechanism for the production of patient-specific pluripotent cells for research and therapy.

The revolutionarily development of iPS technology has opened many new opportunities perhaps the most exciting potential application being the use of patient-specific tissues for transplantation. However, currently the most efficient ways to reprogram somatic cells is to introduce cDNAs that encode four mammalian transcription factors into somatic cells via retroviral vectors. While iPS cells generated in this manner are powerful tools for in vitro studies, there is great concern regarding the safety of returning these manipulate cells to patients. The major concern being that virus-mediated insertional events can potentially activate oncogenes or inactive tumor suppressors thus raising concern for the tumorigenicity of these cells.

Notably, the expression of reprogramming TFs is only transiently required for reprogramming somatic cells. Once converted to iPS cells the activity of these factors is no longer required and indeed, silencing of these ectopic factors is essential to "normal" pluripotency of the iPS cells. Thus, delivery of cDNAs into these cells is not essential, and direct delivery of the proteins themselves into the somatic cells over a prolonged time may represent a more favorable approach. Described herein is the development of a system to circumvent the issues associated with virally-generated iPS cells by reengineering specialized bacterial transkingdom secretion systems to deliver the iPS transforming proteins, the TFs, rather than virulence proteins, directly into mammalian cells.

Development of this system can comprise: (A) the development of non-pathogenic bacteria that encode a TTSS, (B) the modification of mammalian TFs such that they are efficiently secreted by bacterial TTSSs and (C) development of a TTSS-based assay for reprogramming of somatic cells. The system described herein represents a major advance in somatic reprogramming and can have tremendous impact on accelerating the delivery of iPS-based transplant therapies to patients as well as provide a new means of potentially increasing the efficiency of the generation of iPS cells.

Induced pluripotent stem (iPS) are somatic cells that have been reprogrammed to a pluripotent state, which basically means that these cells maintain the capacity to generate each and every cell type in the body. As such these cells provide powerful tools to study basic biologic processes as well serve as a source for the development of patient-specific cell lines that can be used to unravel disease mechanisms, to discover new targets for disease treatment, and ultimately to provide patient-tailored cell therapies. Tremendous progress has been made over the past few years in the induced reprogramming of somatic cells into iPS cells. Remarkably the delivery of genes encoding three or four transcriptions factors (TFs) including Oct3/4, Sox2, Klf4, c-Myc Lin28 and/or Nanog is sufficient to reprogram mouse embryo fibroblasts (MEFs) and other adult stem cells into pluripotent cells [1, 2]. These cells appear to be functionally equivalent to embryonic stem (ES) cells. Currently the greatest success in reprogramming is observed with the delivery of cDNAs contained within retroviral or lentiviral vectors into somatic cells. Although recent evidence indicated that transient transfections [3], non-integrating adenoviral vectors [4] and purified proteins [5] can be used successfully to reprogram cells, albeit very inefficiently. The revolutionarily development of iPS technology has opened many new opportunities perhaps the most exciting potential application being the use of patient specific cells for the treatment of diseases including Parkinson's disease, spinal cord injuries, retinal diseases, type I diabetes and severe burns. However, it is currently accepted that vector free iPS cells must be generated before these pluripotent cells or the tissues derived from them can be introduced into patients. The major concern being that the integration of cDNAs via viral vectors can result in virus-mediated insertional events that activate oncogenes or inhibit tumor suppressor genes. In addition, the integration events often result in persistent low-level expression of the reprogramming factors, which can also significantly alter cell behavior in subsequent assays and predispose these cells to tumorigenesis.

Notably, the expression of reprogramming TFs is only transiently required for reprogramming somatic cells. Once converted to iPS cells the activity of these factors is no longer required and indeed, silencing of these ectopic factors is essential to "normal" pluripotency of the iPS cells. Thus, delivery of cDNAs into these cells is not essential, rather the direct delivery of the transforming proteins themselves into the somatic cells may represent a more favorable approach. Described herein is a system to circumvent the issues associated with virally-generated iPS cells by reengineering specialized bacterial transkingdom secretion systems, specifically type III secretion systems (TTSSs), to deliver the iPS transforming proteins, the TFs, rather than their normal repertoire virulence proteins, directly into mammalian cells.

TTSSs are common to gram-negative pathogens where they deliver tens of proteins involved in virulence into host cells. These complex cellular machines are composed of 20-25 proteins that span both the inner and outer bacterial membranes, forming a channel that extends from the bacterial cytoplasm, across the periplasm and eventually forms a pore in the mammalian host cell membrane [6]. It is well established that heterologous proteins, including mammalian proteins, can be modified such that they are substrates of the secretion system by the addition a type III secretion signal.

Described herein is the reengineering of bacterial TTSSs to deliver mammalian transcription factors rather than pathogenic proteins into host cells. This system would circumvent all of the issues observed with the introduction of viral vectors into somatic cells.

The development of a TTSS-based protein delivery system for the reprogramming of somatic cells would be a major technical advance in the development of the iPS cells The biggest potential impact would be in providing a means to generated viral-free iPS cells thus circumventing the risk of oncogenic events associated with the integration of viral vectors into chromosomes. Thus, this technology could provide a safe means to generate iPS cells and iPS-generated tissues that could be used therapeutically in patients and thus has the potential to impact numerous communities including basic scientists, clinicians and eventually many patients with debilitating diseases.

Furthermore, this protein-based delivery system has several additional potential advantages over the existing retroviral cDNA delivery systems. For example, little is currently known about the immediate early molecular events involved in reprogramming of somatic cells as these are difficult to study when the reprogramming factors are introduced as cDNAs in retroviral vectors given the proteins are not produced until the cDNAs are integrated into genome, transcribe and translated. Clearly, the direct delivery of retransforming proteins would circumvent these issues. In addition, when delivered via integrating vectors it is basically impossible to evaluate whether the ordered expression or stoichiometry of the TFs plays a role in reprogramming. The TTSS-based protein delivery system allows for flexibility in the timing and relative amounts of delivery of the proteins and thus can be used to address these questions. An understanding of early events can improve the efficiency of reprogramming as well accelerate the discovery of small molecules that on their own could potential mediate reprogramming in the absence of delivery of any biologic materials. And lastly, a TTSS-based protein delivery system can be adapted for additional therapeutic uses, like the delivery of tumor suppressors into cancer cells or wild type versions of proteins that complement mutant inherited alleles.

Described herein is a novel methodology for generating induced pluripotent stem (iPS) cells that circumvents many of the limitations that plague currently used viral vector systems. Rather than delivering cDNAs encoding the genes of interest, described herein are bacterial secretion systems that directly inject proteins into mammalian cells to deliver the transcription factors themselves. Specifically, described herein are engineered type III secretion systems (TTSSs) from pathogenic bacteria that specifically deliver mammalian transcription factors (TFs) rather than virulence proteins into mammalian cells.

(A) Development of Non-Pathogenic Bacteria that Encode a TTSS.

While TTSSs are found in endosymbionts, the majority of research has been focused on understanding these systems encoded within pathogenic bacteria, particularly *Shigella, Salmonella* and *Yersinia* species. These bacteria deliver on the order of tens of proteins, referred to as "effectors", directly into host cells. Described herein are several approaches to generate a non-pathogenic bacterial strain with an intact, fully functional TTSS that specifically delivers mammalian TFs rather than effectors into host cells. Two basic approaches can be taken to generate such a strain: (1) Genetically manipulate the pathogenic bacteria such that they no longer encode and produce most effectors and (2) introduce a functional TTSS into a common non-pathogenic laboratory *E. coli* strain like K12 or DH5a. Conditions that induce activation of *Salmonella typhimurium* SPI1 TTSS and the *Shigella flexneri* mxi-spa TTSSs under both in vivo and in vitro conditions are known. All the genes encoding the 20-25 proteins required to form a functional *Salmonella* SPI1 or *Shigella* mxi-spa TTSS are encoded within two large operons located adjacent to each other on the *Shigella* virulence plasmid as well as the *Salmonella* chromosome. Each of these secretion systems is functional and expressed when these operons are introduced into other bacteria [7], [8]. Given that the *Shigella* TTSS is expressed in *E. coli* and the *Salmonella* TTSS is expressed in *Shigella*, it is likely that the *Salmonella* TTSS will be expressed and functional when also expressed in *E. coli.*

*Salmonella* and *Shigella* are intracellular pathogens that mediate their own uptake into non-phagocytic cells. Their TTSSs play a major role in mediating invasion. However, notably, the components of the TTSS machinery themselves do not mediate uptake, rather the activity is dependent on the concerted efforts of several effector proteins [9]. Thus, it is highly unlikely that the engineered *E. coli* strains described herein will invade mammalian cells. Rather, it is likely that they will remain attached to the outer surface of the cells. Of note, although the bacteria selectively attach to specific cell types in vivo, in cell culture, the bacteria are capable of using their TTSS to deliver effectors to whatever cell type they encounter.

These observations suggest that it should be possible to introduce a functional TTSS into common avirulent laboratory strains like K12 *E. coli*. Specifically, homologous recombination can be used to generate bacterial plasmids or artificial chromosomes in yeast. We Shuttle vectors that are expressed as low copy number vectors in both yeast and bacteria can be used to achieve this goal. As this approach has recently been validated for moving an entire bacterial genome from yeast to bacteria [10], it should be suitable for shuttling operons encoding the TTSS which encompass only ~30-40 kB.

An alternative approach can be to create avirulent *S. flexneri* and/or *S. typhimurium* strains that no longer encode or at least no longer express any of the known effectors by creating strains deleted for effectors and/or known master transcription regulators that control their expression of effectors (but not components of the type three secretion machines).

B. Maximize the Secretion of the Transcription Factors Via TTSSs.

There are several variables that need to be optimized to maximize the secretion of functional mammalian TFs from the bacterial TTSS. Into host cells: (1) The proteins need to be modified such that they are recognized as type III secretion substrates, (2) The modified TFs still need to be capable of mediating reprogramming (3) The expression of these mammalian proteins in bacteria needs to be optimized and (4) The TFs need to expressed coordinately with the TTSS. Numerous heterologous proteins, including eukaryotic proteins, can be recognized and secreted by the bacterial TTSS [11]. Their secretion depends on the addition of a secretion signal to their amino termini. While there is no consensus type III secretion signal, the basic components of these signals are known [12]. All effectors encode a "secretion signal" within their first 20 amino acids. This sequence is sometimes sufficient to mediate the delivery of the effectors into host cells. However, in other cases, their secretion depends on the presence of a type III secretion chaperone. In these cases the effectors encode a chaperone-binding domain within their first 60-70 residues. The inventors have systematically determined which of the 25 *Shigella* effectors fall into each category and determined the relative efficiencies of secretion of all 25 effectors [13]. By systematically fusing a variety of secretion signals to the amino termini of the TFs, which sequence results in maximal secretion/translocation of the TFs into host cells can be determined Presumably modifications that add the fewest residues will be least likely to interfere with function. Modifications that result in the maximal delivery of the modified TFs to the nuclei of the infected cells can be screened for. Once these are identified, genes that express the modified TFs can be introduced into retroviral vectors and that these versions are capable of reprogramming the MEFs into iPS cells confirmed.

If a modified TF is not functional, the signal sequences can be cleaved after the TF is delivered into the cytoplasm of the mammalian cells. For example, a calpain or a furin cleavage site can be added between the secretion signal and the effector. Alternatively, a fusion protein that encodes a single ubiquitin molecule (or, e.g. sumo) between the secretion signal and the TF such that the injected protein is recognized by the N-end rule resulting in the removal of the ubiquitin molecule and its upstream sequence can be generated. In this case, the fusion can be engineered such that the newly exposed residues is at the amino terminus is a methionine, as proteins with this amino acid are stable for >20 hours after the ubiquitin is cleaved, at least in the case of GFP and β-galactosidase [14].

After establishing delivery of functional TFs via the TTSS, the conditions that maximize their delivery into mammalian cells can be determined. The levels of secretion when the TFs are expressed from an endogenous type III regulated promotor versus an IPTG or arabinose inducible promotor can be compared. The levels of secretion when encoded on different copy number plasmids can also be compared. More production may not correspond with maximal secretion as in some cases overexpression of effectors can "clog" the type III secretion machinery, although this may not be an issue as the strains used will no longer express the majority if not all of the usual substrates of the TTSS. If expression levels of the TFs in bacteria are low, assembly of synthetic versions of the genes such that their codon composition is optimized for bacterial expression can be explored.

C. Development of a TTSS-Based Assay for Reprogramming of Somatic Cells.

After four bacterial strains that each secrete one of the TFs that together mediate reprogramming have been constructed, a bacterial "infection" assay for the reprogramming of mouse embryo fibroblasts (MEFs) into iPS cells can be developed. The basic design of the assay can be to infect MEFs with the four bacterial strains (each TF encoded in a distinct bacterial strain) and screen for the generation of iPS cells. These experiments can use MEFs carrying GFP under control of the Oct4 promotor, which is expressed only after conversion of MEFs to iPS cells, thereby providing a simple, visual assay to score successful reprogramming to iPS cells [15]. As described below, this straightforward system will be optimized systematically to increase efficiency by addressing key aspects in bacterial protein expression and host cell interactions.

First, from the perspective of the bacteria, it may be necessary to limit the numbers of bacteria present in MEF co-cultures, as bacteria clearly can outgrow MEFs and could disturb the culture media conditions. The system may work best if bacteria are added to MEFs at cyclic intervals (e.g., 8-12 hrs), in which the bacteria can infect for 2-3 hours, after which a media-restricted antibiotic, like gentamicin, to kill the bacteria will be added. The bacteria can be engineered such that they cannot invade host cells, but maintain normal intracellular processes. To optimize these time points, a series of control experiments to determine the length of time the T3SS of the genetically modified bacteria actively delivers the TFs after contacting the MEFs can be performed.

T3SS are only activated once the bacteria contact host cells. To optimize the number of bacteria added to the cell culture that actually contact the MEFs, the utility of introducing one or two *E. coli* adhesins, e.g *E. coli* Afa1 and AIDA, into the genetic engineered strains can be tested. These adhesins play a major role in the adherence of *E. coli* to host cells. Addition of AfaI to *Shigella* results in a 1,000-fold increase in their ability to adhere to a variety of host cell types [16]. To circumvent the activation of innate immune signaling processes bacterial strains that do not produce flagellin or immunogenic LPS can be used.

Once the delivery of functional TFs into MEFs has been optimized and conditions that minimally impact MEF growth identified, MEF reprogramming by TF delivery can be focused upon. Although the reported efficiency of reprogramming (by viral transduction or gene induction approaches) is typically only 0.01-1%, the ability to detect these rare events can be enhanced by using MEFs that encode GFP under the control of the Oct4 promotor. This promotor is inactive in MEFs but is activated in iPS cells. Thus, visual screens for reprogrammed iPS cells can be conducted. Additionally, to increase the likelihood of producing iPS cells, these experiments can be performed in the presence of small molecules, like valproic acid (VPA) which is reported to increase the efficiency of reprogramming 100-fold [17]. Using such visual selection, reprogramming assays can be conducted in 24 or 48 well format thus allowing rapid screening of a variety of different conditions.

Different combinations of TFs have been reported to successfully reprogram somatic cells, including the combinations Oct4, Sox2, Klf4, and c-Myc, or Oct4, Sox2, Nanog and Lin28. Little is currently known about the specific requirements of each of these individual TFs, or their optimal stoichiometry, in reprogramming Thus, bacteria strains that each secrete one of the TFs will be constructed. Strains that secrete a single TF rather than all four can (a) maximize the secretion of each protein and (b) allow screening for different conditions that mediate reprogramming by exposing the MEFs to different ratios of three or four strains that each deliver a different TF. There is evidence suggesting that reprogramming TFs need to be present for at least 6-14 days [18, 19], thus, daily infections can be conducted for an extended time (2-4 weeks). Of note, in parallel, whether the T3SS-based assay can be used to reprogram MEFs into myoblasts, a relatively more simple manipulation, can also be tested. In this case, the expression of a single TF, MyoD, is sufficient to mediate reprogramming [20]. For this experiment, a bacterial strain capable of secreting MyoD via the T3SS can be generated and the ability of the T3SS system to generate muscle cells from MEFs tested. This assay involves infection with only one, rather than 3-4, different strains of bacteria.

The technology described herein is be broadly useful, particularly in that the system can be adapted to deliver designated proteins to specific cell types in vivo. For example, tumor suppressors could be targeted to tumors or anti-inflammatory promoting proteins could be targeted to tissues involved in autoimmune-mediated diseases, like Crohn's disease or ulcerative colitis.

The approach described herein to generate iPS cells using bacterial secretion systems has not, to the inventors' knowledge been previously proposed and tackles the biggest major technical hurdle in bringing iPS-based therapies to patients in the clinical arena.

REFERENCES

1. Takahashi, K., et al., Induction of pluripotent stem cells from adult human fibroblasts by defined factors. Cell, 2007. 131(5): p. 861-72.
2. Yu, J., et al., Induced pluripotent stem cell lines derived from human somatic cells. Science, 2007. 318(5858): p. 1917-20.
3. Okita, K., et al., Generation of mouse induced pluripotent stem cells without viral vectors. Science, 2008. 322 (5903): p. 949-53.
4. Stadtfeld, M., et al., Induced pluripotent stem cells generated without viral integration. Science, 2008. 322 (5903): p. 945-9.
5. Kim, D., et al., Generation of human induced pluripotent stem cells by direct delivery of reprogramming proteins. Cell Stem Cell, 2009. 4(6): p. 472-6.
6. Galan, J. E. and H. Wolf-Watz, Protein delivery into eukaryotic cells by type III secretion machines. Nature, 2006. 444(7119): p. 567-73.
7. Sansonetti, P. J., et al., Alterations in the pathogenicity of *Escherichia coli* K-12 after transfer of plasmid and chromosomal genes from *Shigella flexneri*. Infect Immun, 1983. 39(3): p. 1392-402.
8. Paetzold, S., et al., *Shigella flexneri* phagosomal escape is independent of invasion. Infect Immun, 2007. 75(10): p. 4826-30.
9. Zhou, D., et al., A *Salmonella* inositol polyphosphatase acts in conjunction with other bacterial effectors to promote host cell actin cytoskeleton rearrangements and bacterial internalization. Mol Microbiol, 2001. 39(2): p. 248-59.
10. Lartigue, C., et al., Creating bacterial strains from genomes that have been cloned and engineered in yeast. Science, 2009. 325(5948): p. 1693-6.
11. Chamekh, M., et al., Delivery of biologically active anti-inflammatory cytokines IL-10 and IL-1ra in vivo by the *Shigella* type III secretion apparatus. J Immunol, 2008. 180(6): p. 4292-8.
12. Ghosh, P., Process of protein transport by the type III secretion system. Microbiol Mol Biol Rev, 2004. 68(4): p. 771-95.
13. Schmitz, A. M., et al., Protein interaction platforms: visualization of interacting proteins in yeast. Nat Methods, 2009. 6(7): p. 500-2.
14. Bachmair, A., D. Finley, and A. Varshaysky, In vivo half-life of a protein is a function of its aminoterminal residue. Science, 1986. 234(4773): p. 179-86.
15. Lengner, C. J., et al., Oct4 expression is not required for mouse somatic stem cell self-renewal. Cell Stem Cell, 2007. 1(4): p. 403-15.
16. Clerc, P. and P. J. Sansonetti, Entry of *Shigella flexneri* into HeLa cells: evidence for directed phagocytosis involving actin polymerization and myosin accumulation. Infect Immun, 1987. 55(11): p. 2681-8.
17. Huangfu, D., et al., Induction of pluripotent stem cells by defined factors is greatly improved by small molecule compounds. Nat Biotechnol, 2008. 26(7): p. 795-7.
18. Stadtfeld, M., et al., Defining molecular cornerstones during fibroblast to iPS cell reprogramming in mouse. Cell Stem Cell, 2008. 2(3): p. 230-40.
19. Brambrink, T., et al., Sequential expression of pluripotency markers during direct reprogramming of mouse somatic cells. Cell Stem Cell, 2008. 2(2): p. 151-9.
20. Davis, R. L., H. Weintraub, and A. B. Lassar, Expression of a single transfected cDNA converts fibroblasts to myoblasts. Cell, 1987. 51(6): p. 987-1000.

Example 5—Integration of Region Encoding the Type 3 Secretion System Operons in the Chromosome of DH10b and Nissle *E. coli* 1917

Given the relative instability of the large plasmid that carries the type 3 secretion plasmid when introduced into bacteria, homologous recombination technology was used to introduce the operons into the chromosome to remove the instability factor. Specifically a variant of "landing pad" technology developed by Kuhlman and Cox (Nucleic Acids Research 2010 38:e92), was utilized. This modification has resulted in strains that stably express a functional type 3 secretion system and provides an important additional modification as stability can be a desired state when the strains are used as in vivo biologic agents.

Example 6 Development of Non-Invasive Type 3 Secretion Competent Strains of *E. coli*

It is demonstrated herein that the four type 3 endogenous secreted *Shigella* proteins present on the region of the *Shigella* plasmid DNA that contains the genes needed to make a functional machine are sufficient to mediate the uptake of minT3 bacteria into the cytosol of host cells. "MinT3" refers to an *E. coli* that expresses the minimal type 3 secretion system. The genes for the minimal type 3 secretion system can be present in the chromosome and/or on one or more plasmids. Given this observation, a version of minT3 bacteria has been developed that no longer encode any endogenous secreted proteins. This strain of *E. coli* binds to the outside surface of the cell and delivers proteins into human cells, but does not itself invade the cell (FIG. 1). It is specifically contemplated herein that the strains might have different therapeutic uses. By way of non-limiting example, strains that invade and trigger innate immune responses including cell death are advantageous for targeting solid tumors, while those that remain extracellular are beneficial, for example, for reprogramming or for delivering anti-inflammatory proteins into host cells.

There are four secreted proteins present in the operons that encode the components needed to make a functional *Shigella* type 3 secretion machine. These proteins are IpgB1, IpgD, IpaA and IcsB. Three of the proteins, IpgB1, IpgD and IpaA have been implicated to be involved in playing a role in the uptake of *Shigella*, an intracellular pathogen, into host cells. These include IpgB1, IpgD and IpaA. The fourth secreted protein, IcsB, plays a role in blocking autophagy and preventing the uptake of *Shigella* into autophagosomes. IpgD shares homology with a *Salmonella* protein, SopB, which is involved in the uptake of *Salmonella* into host cells. IpgB1 is a Rho GTP exchange favor that is thought to specifically target Rac to induce ruffles that mediate the uptake of *Shigella* into host cells.

Many other bacterial pathogens encode IpgB1 homologs, including *Shigella*, these homologs target a variety of Rho GTPases. IpaA shares some homology with *Salmonella* SipA, a protein involved in the uptake of *Salmonella* into host cells. But, IpaA likely interacts with vinculin while SipA interacts with actin.

What is claimed herein is:

1. An engineered microbial cell comprising:

a) a first nucleic acid sequence comprising genes encoding a functional type three secretion system (T3SS), wherein the genes encoding the functional T3SS are: Acyl Carrier Protein (acp); Invasion Plasmid Antigen (ipa) A, ipaB, ipaC, ipaD, ipgC), Invasion Plasmid Gene (ipgB)1, ipgA, Intra-Inter-Cellular Spread B (icsB), ipgD, ipgE, ipgF, Membrane expression of Invasion plasmid antigens (mxi) G, mxiH, mxiI, mxiJ, mxiK, mxiN, mxiL, mxiM, mxiE, mxiD, mxiC, mxiA, Surface Presentation Antigens (spa)15, spa47, spa13, spa32, spa33, spa24, spa9, spa29, and spa40 or homologs thereof, and b) a second nucleic acid sequence encoding a virF and/or VirB transcriptional regulator, or homologs thereof, wherein the genes encoding the functional T3SS are isolated from a pathogenic bacterium selected from the group consisting of *Salmonella* spp., *Shigella* Spp, and *Yersinia* spp, whereby the functional T3SS comprises a set of structural proteins which form a T3SS capable of transferring at least one polypeptide into an eukaryotic target cell; and c) a third nucleic acid sequence encoding a T3SS-compatible polypeptide wherein the T3SS-compatible polypeptide comprises a T3SS secretion signal, wherein the engineered microbial cell is *Escherichia coli* and wherein said *E. coli* did not comprise a native T3SS prior to being engineered to comprise the first and second nucleic acid sequences encoding the functional T3SS and the virF and/or VirB transcriptional regulator.

2. The engineered microbial cell of claim 1, wherein the T3SS-compatible polypeptide is exogenous or ectopic to the microbial cell.

3. The engineered microbial cell of claim 1, wherein the engineered microbial cell is a commensal intestinal microbial cell.

4. The engineered microbial cell of claim 1, wherein the *Escherichia coli* is selected from the group consisting of: *E. coli* NISSLE 1917 (EcN); *E. coli* K12; *E. coli* DH1013; *E. coli* HB101; *E. coli* BL21; *E. coli* JM110; *E. coli* MinT3; *E. coli* 83972; *E. coli* M17; and *E. coli* DH5a.

5. The engineered microbial cell of claim 1, wherein the cell further comprises a forth nucleic acid sequence encoding one or more polypeptides that increase adhesion to the target cell.

6. The engineered microbial cell of claim 5, wherein the polypeptides that increase adhesion to the target cell comprise Tir and intimin.

7. The engineered microbial cell of claim 5, wherein the polypeptide that increases adhesion to the target cell is selected from a group consisting of a bacterial adhesion, Afimbrial X-type Adhesin 1 (Afa1), Adhesin Involved in Diffuse Adherence (AIDA) and an invasion.

8. The engineered microbial cell of claim 1, wherein the third nucleic acid sequence encoding the T3SS-compatible polypeptide is operatively linked to a type three secretion system (T3SS)-associated promoter or promoter element.

9. The engineered microbial cell of claim 1, wherein the second nucleic acid encoding the T3SS-compatible polypeptide is operatively linked to an inducible promoter.

10. The engineered microbial cell of claim 1, wherein the T3SS-compatible polypeptide comprises an anti-inflammatory polypeptide, a toxin, a tumor suppressor polypeptide, a reprogramming factor, a transdifferentiation factor, antigen, or antigen derived from an enteric pathogen.

11. A method of introducing a polypeptide into a target cell, the method comprising contacting the target cell with an engineered microbial cell of claim 1.

* * * * *

SEQUENCE LISTING

<160> NUMBER OF SEQ ID NOS: 102

<210> SEQ ID NO 1
<211> LENGTH: 882
<212> TYPE: DNA
<213> ORGANISM: Escherichia coli

<400> SEQUENCE: 1

```
atgttatcgc catattctgt aaatttggga tgttcatgga attctttaac cagaaacctg      60

acttcgcctg ataatcgtgt tttatcctct gtaagggatg ctgccgttca ttctgataat     120

ggggcgcaag taaaggttgg caacagaaca tatcgtgttg ttgccaccga taataagttt     180

tgcgttacaa gagaaagtca tagtggttgt tttactaatc tgttgcacag gctgggatgg     240

cctaaggggg agattagcag gaaaattgag gtcatgctga atgcatcacc agtgagcgct     300

gctatggaaa gaggcattgt tcattcgaac agacctgatt tacctcctgt tgattatgca     360

ccgccagagt taccgagtgt ggactataac aggttgtcag tacctggtaa tgttattggc     420

aaagggggga acgctgtagt atatgaagat gctgaggatg caacaaaagt cctgaagatg     480

tttactacat ctcaaagcaa tgaagaggtg acaagcgaag ttcgttgctt caaccaatat     540

tatggtgccg ggagtgcaga aaaaatatat ggcaataatg gtgatattat tggtattaga     600

atggataaaa taaatggaga atcgctttta aatatttcgt ccttgccagc acaggctgag     660

catgctattt acgatatgtt tgatagactg gagcaaaaag gaattctttt tgtcgataca     720

acagagacaa atatcttata tgaccgcgcg aagaatgagt ttaatccaat agatatatca     780

tcttataatg tttccgaccg ttcatggagt gaaagtcaaa taatgcaatc ttatcatggc     840

ggaaagcaag atcttattag tgtggtatta agtaaaattt ag                        882
```

<210> SEQ ID NO 2
<211> LENGTH: 293
<212> TYPE: PRT
<213> ORGANISM: Escherichia coli

<400> SEQUENCE: 2

```
Met Leu Ser Pro Tyr Ser Val Asn Leu Gly Cys Ser Trp Asn Ser Leu
1               5                   10                  15

Thr Arg Asn Leu Thr Ser Pro Asp Asn Arg Val Leu Ser Ser Val Arg
            20                  25                  30

Asp Ala Ala Val His Ser Asp Asn Gly Ala Gln Val Lys Val Gly Asn
        35                  40                  45

Arg Thr Tyr Arg Val Val Ala Thr Asp Asn Lys Phe Cys Val Thr Arg
    50                  55                  60

Glu Ser His Ser Gly Cys Phe Thr Asn Leu Leu His Arg Leu Gly Trp
65                  70                  75                  80

Pro Lys Gly Glu Ile Ser Arg Lys Ile Glu Val Met Leu Asn Ala Ser
                85                  90                  95

Pro Val Ser Ala Ala Met Glu Arg Gly Ile Val His Ser Asn Arg Pro
            100                 105                 110

Asp Leu Pro Pro Val Asp Tyr Ala Pro Pro Glu Leu Pro Ser Val Asp
        115                 120                 125

Tyr Asn Arg Leu Ser Val Pro Gly Asn Val Ile Gly Lys Gly Gly Asn
    130                 135                 140

Ala Val Val Tyr Glu Asp Ala Glu Asp Ala Thr Lys Val Leu Lys Met
145                 150                 155                 160

Phe Thr Thr Ser Gln Ser Asn Glu Glu Val Thr Ser Glu Val Arg Cys
```

```
                165                 170                 175

Phe Asn Gln Tyr Tyr Gly Ala Gly Ser Ala Glu Lys Ile Tyr Gly Asn
            180                 185                 190

Asn Gly Asp Ile Ile Gly Ile Arg Met Asp Lys Ile Asn Gly Glu Ser
        195                 200                 205

Leu Leu Asn Ile Ser Ser Leu Pro Ala Gln Ala Glu His Ala Ile Tyr
    210                 215                 220

Asp Met Phe Asp Arg Leu Glu Gln Lys Gly Ile Leu Phe Val Asp Thr
225                 230                 235                 240

Thr Glu Thr Asn Ile Leu Tyr Asp Arg Ala Lys Asn Glu Phe Asn Pro
                245                 250                 255

Ile Asp Ile Ser Ser Tyr Asn Val Ser Asp Arg Ser Trp Ser Glu Ser
            260                 265                 270

Gln Ile Met Gln Ser Tyr His Gly Gly Lys Gln Asp Leu Ile Ser Val
        275                 280                 285

Val Leu Ser Lys Ile
    290


<210> SEQ ID NO 3
<211> LENGTH: 591
<212> TYPE: DNA
<213> ORGANISM: Shigella flexneri

<400> SEQUENCE: 3

atgaaaataa catctaccat tattcaaaca ccttttccat ttgagaataa taattctcat     60

gctggcatag taacggagcc cattctcggt aagttaatag gtcaggggtc gacagcagaa    120

atctttgaag atgtgaatga ttcatctgct ttgtataaaa agtatgatct tattggcaac    180

cagtacaatg agattctgga aatggcttgg caagaatctg agctttttaa tgctttttat    240

ggcgatgaag catccgttgt tatacagtat ggcggagatg tgtacctccg aatgctgcgc    300

gtgcctggga ctccccttag tgacattgat acagctgata tccctgataa tatagagagc    360

ctttatctac agttgatatg taaattgaat gagttgagta taatccatta cgatcttaat    420

acaggtaata tgctgtatga taaagaaagt gaaagtttat tcccaataga ttttcgcaat    480

atttatgctg aatattacgc tgcaaccaaa aaagataaag agattatcga ccgacgatta    540

caaatgcgta caaatgattt ttattcgtta ttaaacagga aatatttata g             591


<210> SEQ ID NO 4
<211> LENGTH: 196
<212> TYPE: PRT
<213> ORGANISM: Shigella flexneri

<400> SEQUENCE: 4

Met Lys Ile Thr Ser Thr Ile Ile Gln Thr Pro Phe Pro Phe Glu Asn
1               5                   10                  15

Asn Asn Ser His Ala Gly Ile Val Thr Glu Pro Ile Leu Gly Lys Leu
            20                  25                  30

Ile Gly Gln Gly Ser Thr Ala Glu Ile Phe Glu Asp Val Asn Asp Ser
        35                  40                  45

Ser Ala Leu Tyr Lys Lys Tyr Asp Leu Ile Gly Asn Gln Tyr Asn Glu
    50                  55                  60

Ile Leu Glu Met Ala Trp Gln Glu Ser Glu Leu Phe Asn Ala Phe Tyr
65                  70                  75                  80

Gly Asp Glu Ala Ser Val Val Ile Gln Tyr Gly Gly Asp Val Tyr Leu
                85                  90                  95
```

```
Arg Met Leu Arg Val Pro Gly Thr Pro Leu Ser Asp Ile Asp Thr Ala
            100                 105                 110

Asp Ile Pro Asp Asn Ile Glu Ser Leu Tyr Leu Gln Leu Ile Cys Lys
        115                 120                 125

Leu Asn Glu Leu Ser Ile Ile His Tyr Asp Leu Asn Thr Gly Asn Met
    130                 135                 140

Leu Tyr Asp Lys Glu Ser Glu Ser Leu Phe Pro Ile Asp Phe Arg Asn
145                 150                 155                 160

Ile Tyr Ala Glu Tyr Tyr Ala Ala Thr Lys Lys Asp Lys Glu Ile Ile
                165                 170                 175

Asp Arg Arg Leu Gln Met Arg Thr Asn Asp Phe Tyr Ser Leu Leu Asn
            180                 185                 190

Arg Lys Tyr Leu
        195
```

<210> SEQ ID NO 5
<211> LENGTH: 720
<212> TYPE: DNA
<213> ORGANISM: Shigella flexneri

<400> SEQUENCE: 5

```
atgcccataa aaaagccctg tctaaaacta aatttagatt ctttgaatgt tgtgaagtct      60

gaaataccgc agatgctttc tgcgaatgaa agattgaaaa ataacttcaa tatattgtac     120

aaccaaatac ggcaataccc agcgtactat ttcaaagtag catcgaacgt gccaacttac     180

tctgatatat gtcaattttt ttctgtcatg taccaaggat tccagattgt gaaccatagt     240

ggagatgtgt ttattcatgc atgtcgtgaa aatcctcaga gtaaggggga ttttgttggg     300

gacaagtttc atattagtat agctagggag caagttcctc tggcattcca aattttgtct     360

ggtttattat tttcagagga cagtcctata gataaatgga agataactga tatgaatcga     420

gtttctcagc aatctcgtgt ggggatagga gctcagttta cgctatatgt aaaatcagat     480

caggaatgct cgcaatatag tgctttatta cttcataaaa tacgacaatt tataatgtgt     540

ctcgagtcta atctattaag aagcaaaatc gctcccgggg agtatccggc gtcagatgtt     600

agacctgaag actggaaata tgtcagctat cgtaatgaac tacgaagcga tcgagatgga     660

agtgaaaggc aagagcaaat gttacgagag gaaccatttt atcgtttgat gatagagtag     720
```

<210> SEQ ID NO 6
<211> LENGTH: 239
<212> TYPE: PRT
<213> ORGANISM: Shigella flexneri

<400> SEQUENCE: 6

```
Met Pro Ile Lys Lys Pro Cys Leu Lys Leu Asn Leu Asp Ser Leu Asn
1               5                   10                  15

Val Val Lys Ser Glu Ile Pro Gln Met Leu Ser Ala Asn Glu Arg Leu
            20                  25                  30

Lys Asn Asn Phe Asn Ile Leu Tyr Asn Gln Ile Arg Gln Tyr Pro Ala
        35                  40                  45

Tyr Tyr Phe Lys Val Ala Ser Asn Val Pro Thr Tyr Ser Asp Ile Cys
    50                  55                  60

Gln Phe Phe Ser Val Met Tyr Gln Gly Phe Gln Ile Val Asn His Ser
65                  70                  75                  80

Gly Asp Val Phe Ile His Ala Cys Arg Glu Asn Pro Gln Ser Lys Gly
                85                  90                  95
```

-continued

```
Asp Phe Val Gly Asp Lys Phe His Ile Ser Ile Ala Arg Glu Gln Val
            100                 105                 110

Pro Leu Ala Phe Gln Ile Leu Ser Gly Leu Leu Phe Ser Glu Asp Ser
        115                 120                 125

Pro Ile Asp Lys Trp Lys Ile Thr Asp Met Asn Arg Val Ser Gln Gln
    130                 135                 140

Ser Arg Val Gly Ile Gly Ala Gln Phe Thr Leu Tyr Val Lys Ser Asp
145                 150                 155                 160

Gln Glu Cys Ser Gln Tyr Ser Ala Leu Leu Leu His Lys Ile Arg Gln
                165                 170                 175

Phe Ile Met Cys Leu Glu Ser Asn Leu Leu Arg Ser Lys Ile Ala Pro
            180                 185                 190

Gly Glu Tyr Pro Ala Ser Asp Val Arg Pro Glu Asp Trp Lys Tyr Val
        195                 200                 205

Ser Tyr Arg Asn Glu Leu Arg Ser Asp Arg Asp Gly Ser Glu Arg Gln
    210                 215                 220

Glu Gln Met Leu Arg Glu Glu Pro Phe Tyr Arg Leu Met Ile Glu
225                 230                 235


<210> SEQ ID NO 7
<211> LENGTH: 1668
<212> TYPE: DNA
<213> ORGANISM: Shigella flexneri

<400> SEQUENCE: 7

ttgtccaccg gctttaactg gatgcccatc atgttaccga taaataataa cttttcattg     60

ccccaaaatt ctttttataa cactatttcc ggtacatatg ctgattactt ttcagcatgg    120

gataaatggg aaaaacaagc gctccccggt gaagagcgtg atgaggctgt ctcccgactt    180

aaagaatgtc ttatcaataa ttccgatgaa cttcgactgg accgtttaaa tctgtcctcg    240

ctacctgaca acttaccagc tcagataacg ctgctcaatg tatcatataa tcaattaact    300

aacctacctg aactgcctgt tacgctaaaa aaattatatt ccgccagcaa taaattatca    360

gaattgcccg tgctacctcc tgcgctggag tcacttcagg tacaacacaa tgagctggaa    420

aacctgccag ctttacccga ttcgttattg actatgaata tcagctataa cgaaatagtc    480

tccttaccat cgctcccaca ggctcttaaa aatctcagag cgacccgtaa tttcctcact    540

gagctaccag cattttctga gggaaataat cccgttgtca gagagtattt ttttgataga    600

aatcagataa gtcatatccc ggaaagcatt cttaatctga ggaatgaatg ttcaatacat    660

attagtgata acccattatc atcccatgct ctgcaagccc tgcaaagatt aacctcttcg    720

ccggactacc acggcccacg gatttacttc tccatgagtg acggacaaca gaatacactc    780

catcgccccc tggctgatgc cgtgacagca tggttcccgg aaaacaaaca atctgatgta    840

tcacagatat ggcatgcttt tgaacatgaa gagcatgcca acacctttttc cgcgttcctt    900

gaccgccttt ccgataccgt ctctgcacgc aatacctccg gattccgtga acaggtcgct    960

gcatggctgg aaaaactcag tgcctctgcg gagcttcgac agcagtcttt cgctgttgct   1020

gctgatgcca ctgagagctg tgaggaccgt gtcgcgctca catggaacaa tctccggaaa   1080

accctcctgg tccatcaggc atcagaaggc cttttcgata atgataccgg cgctctgctc   1140

tccctgggca gggaaatgtt ccgcctcgaa attctggagg atattgcccg ggataaagtc   1200

agaactctcc attttgtgga tgagatagaa gtctacctgg ccttccagac catgctcgca   1260

gagaaacttc agctctccac tgccgtgaag gaaatgcgtt tctatggcgt gtcgggagtg   1320
```

```
acagcaaatg acctccgcac tgccgaagcc atggtcagaa gccgtgaaga gaatgaattt   1380

acggactggt tctccctctg gggaccatgg catgctgtac tgaagcgtac ggaagctgac   1440

cgctgggcgc aggcagaaga gcagaaatat gagatgctgg agaatgagta ccctcagagg   1500

gtggctgacc ggctgaaagc atcaggtctg agcggtgatg cggatgcgga gagggaagcc   1560

ggtgcacagg tgatgcgtga gactgaacag cagatttacc gtcagctgac tgacgaggta   1620

ctggccctgc gattgtctga aaacggctca caactgcacc attcataa                1668


<210> SEQ ID NO 8
<211> LENGTH: 555
<212> TYPE: PRT
<213> ORGANISM: Shigella flexneri

<400> SEQUENCE: 8

Met Ser Thr Gly Phe Asn Trp Met Pro Ile Met Leu Pro Ile Asn Asn
1               5                   10                  15

Asn Phe Ser Leu Pro Gln Asn Ser Phe Tyr Asn Thr Ile Ser Gly Thr
            20                  25                  30

Tyr Ala Asp Tyr Phe Ser Ala Trp Asp Lys Trp Glu Lys Gln Ala Leu
        35                  40                  45

Pro Gly Glu Glu Arg Asp Glu Ala Val Ser Arg Leu Lys Glu Cys Leu
    50                  55                  60

Ile Asn Asn Ser Asp Glu Leu Arg Leu Asp Arg Leu Asn Leu Ser Ser
65                  70                  75                  80

Leu Pro Asp Asn Leu Pro Ala Gln Ile Thr Leu Leu Asn Val Ser Tyr
                85                  90                  95

Asn Gln Leu Thr Asn Leu Pro Glu Leu Pro Val Thr Leu Lys Lys Leu
            100                 105                 110

Tyr Ser Ala Ser Asn Lys Leu Ser Glu Leu Pro Val Leu Pro Pro Ala
        115                 120                 125

Leu Glu Ser Leu Gln Val Gln His Asn Glu Leu Glu Asn Leu Pro Ala
    130                 135                 140

Leu Pro Asp Ser Leu Leu Thr Met Asn Ile Ser Tyr Asn Glu Ile Val
145                 150                 155                 160

Ser Leu Pro Ser Leu Pro Gln Ala Leu Lys Asn Leu Arg Ala Thr Arg
                165                 170                 175

Asn Phe Leu Thr Glu Leu Pro Ala Phe Ser Glu Gly Asn Asn Pro Val
            180                 185                 190

Val Arg Glu Tyr Phe Phe Asp Arg Asn Gln Ile Ser His Ile Pro Glu
        195                 200                 205

Ser Ile Leu Asn Leu Arg Asn Glu Cys Ser Ile His Ile Ser Asp Asn
    210                 215                 220

Pro Leu Ser Ser His Ala Leu Gln Ala Leu Gln Arg Leu Thr Ser Ser
225                 230                 235                 240

Pro Asp Tyr His Gly Pro Arg Ile Tyr Phe Ser Met Ser Asp Gly Gln
                245                 250                 255

Gln Asn Thr Leu His Arg Pro Leu Ala Asp Ala Val Thr Ala Trp Phe
            260                 265                 270

Pro Glu Asn Lys Gln Ser Asp Val Ser Gln Ile Trp His Ala Phe Glu
        275                 280                 285

His Glu Glu His Ala Asn Thr Phe Ser Ala Phe Leu Asp Arg Leu Ser
    290                 295                 300

Asp Thr Val Ser Ala Arg Asn Thr Ser Gly Phe Arg Glu Gln Val Ala
```

```
305                 310                 315                 320

Ala Trp Leu Glu Lys Leu Ser Ala Ser Ala Glu Leu Arg Gln Gln Ser
                325                 330                 335

Phe Ala Val Ala Ala Asp Ala Thr Glu Ser Cys Glu Asp Arg Val Ala
            340                 345                 350

Leu Thr Trp Asn Asn Leu Arg Lys Thr Leu Leu Val His Gln Ala Ser
        355                 360                 365

Glu Gly Leu Phe Asp Asn Asp Thr Gly Ala Leu Leu Ser Leu Gly Arg
    370                 375                 380

Glu Met Phe Arg Leu Glu Ile Leu Glu Asp Ile Ala Arg Asp Lys Val
385                 390                 395                 400

Arg Thr Leu His Phe Val Asp Glu Ile Glu Val Tyr Leu Ala Phe Gln
                405                 410                 415

Thr Met Leu Ala Glu Lys Leu Gln Leu Ser Thr Ala Val Lys Glu Met
            420                 425                 430

Arg Phe Tyr Gly Val Ser Gly Val Thr Ala Asn Asp Leu Arg Thr Ala
        435                 440                 445

Glu Ala Met Val Arg Ser Arg Glu Glu Asn Glu Phe Thr Asp Trp Phe
    450                 455                 460

Ser Leu Trp Gly Pro Trp His Ala Val Leu Lys Arg Thr Glu Ala Asp
465                 470                 475                 480

Arg Trp Ala Gln Ala Glu Glu Gln Lys Tyr Glu Met Leu Glu Asn Glu
                485                 490                 495

Tyr Pro Gln Arg Val Ala Asp Arg Leu Lys Ala Ser Gly Leu Ser Gly
            500                 505                 510

Asp Ala Asp Ala Glu Arg Glu Ala Gly Ala Gln Val Met Arg Glu Thr
        515                 520                 525

Glu Gln Gln Ile Tyr Arg Gln Leu Thr Asp Glu Val Leu Ala Leu Arg
    530                 535                 540

Leu Ser Glu Asn Gly Ser Gln Leu His His Ser
545                 550                 555


<210> SEQ ID NO 9
<211> LENGTH: 1023
<212> TYPE: DNA
<213> ORGANISM: Salmonella enterica

<400> SEQUENCE: 9

atgaatatat gtgtaaattc actttaccga ttgagcatac cgcaatttca cagcttatat      60

acagaagagg tgagcgatga ggcgcttaca ttgttgttta gcgccgtaga gaacggtgat     120

cagaattgta ttgatctgtt atgcaatctt gcgttacgca acgatgacct ggggcataga     180

gttgagaaat ttctttttga tctctttagc gggaaaagaa cgggatcatc agatatagac     240

aaaaaaatca atcaggcttg ccttgtatta catcaaatcg ccaataacga tataacaaaa     300

gataatactg agtggaaaaa gctacatgcc ccttccagat tactttatat ggcaggttcc     360

gcgacaaccg acctttctaa aaaaatagga atagcacata aaattatggg cgaccagttc     420

gctcagacag atcaagaaca ggtaggagtt gaaaatcttt ggtgtggtgc gcgaatgttg     480

tcgtcagatg agctagcagc tgcaacgcaa ggtctggttc aagaatcacc tcttctctcg     540

gtaaactatc ctattgggct gattcatcct accaccaaag aaaatatatt aagcactcag     600

ctacttgaaa agattgctca atcaggatta tctcacaatg aagtcttcct ggtaaataca     660

ggagatcact ggcttctctg tttattttat aaacttgcag aaaaaataaa atgccttata     720
```

```
tttaatactt attatgattt aaatgaaaat actaagcaag agattataga agcagcaaaa    780

attgcaggca tatcagaaag cgatgaggtt aattttattg aaatgaattt acagaacaat    840

gtacccaacg gctgtggtct attttgttac catacaattc aactcttatc gaatgccgga    900

caaaacgatc ctgctaccac actacgagaa tttgcggaaa atttcttaac gctttcagta    960

gaggaacaag cactatttaa cacccaaacc cggcggcaaa tatatgaata cagtctccag   1020

taa                                                                 1023
```

<210> SEQ ID NO 10
<211> LENGTH: 340
<212> TYPE: PRT
<213> ORGANISM: Salmonella enterica

<400> SEQUENCE: 10

```
Met Asn Ile Cys Val Asn Ser Leu Tyr Arg Leu Ser Ile Pro Gln Phe
1               5                   10                  15

His Ser Leu Tyr Thr Glu Glu Val Ser Asp Glu Ala Leu Thr Leu Leu
            20                  25                  30

Phe Ser Ala Val Glu Asn Gly Asp Gln Asn Cys Ile Asp Leu Leu Cys
        35                  40                  45

Asn Leu Ala Leu Arg Asn Asp Asp Leu Gly His Arg Val Glu Lys Phe
    50                  55                  60

Leu Phe Asp Leu Phe Ser Gly Lys Arg Thr Gly Ser Ser Asp Ile Asp
65                  70                  75                  80

Lys Lys Ile Asn Gln Ala Cys Leu Val Leu His Gln Ile Ala Asn Asn
                85                  90                  95

Asp Ile Thr Lys Asp Asn Thr Glu Trp Lys Lys Leu His Ala Pro Ser
            100                 105                 110

Arg Leu Leu Tyr Met Ala Gly Ser Ala Thr Thr Asp Leu Ser Lys Lys
        115                 120                 125

Ile Gly Ile Ala His Lys Ile Met Gly Asp Gln Phe Ala Gln Thr Asp
    130                 135                 140

Gln Glu Gln Val Gly Val Glu Asn Leu Trp Cys Gly Ala Arg Met Leu
145                 150                 155                 160

Ser Ser Asp Glu Leu Ala Ala Ala Thr Gln Gly Leu Val Gln Glu Ser
                165                 170                 175

Pro Leu Leu Ser Val Asn Tyr Pro Ile Gly Leu Ile His Pro Thr Thr
            180                 185                 190

Lys Glu Asn Ile Leu Ser Thr Gln Leu Leu Glu Lys Ile Ala Gln Ser
        195                 200                 205

Gly Leu Ser His Asn Glu Val Phe Leu Val Asn Thr Gly Asp His Trp
    210                 215                 220

Leu Leu Cys Leu Phe Tyr Lys Leu Ala Glu Lys Ile Lys Cys Leu Ile
225                 230                 235                 240

Phe Asn Thr Tyr Tyr Asp Leu Asn Glu Asn Thr Lys Gln Glu Ile Ile
                245                 250                 255

Glu Ala Ala Lys Ile Ala Gly Ile Ser Glu Ser Asp Glu Val Asn Phe
            260                 265                 270

Ile Glu Met Asn Leu Gln Asn Asn Val Pro Asn Gly Cys Gly Leu Phe
        275                 280                 285

Cys Tyr His Thr Ile Gln Leu Leu Ser Asn Ala Gly Gln Asn Asp Pro
    290                 295                 300

Ala Thr Thr Leu Arg Glu Phe Ala Glu Asn Phe Leu Thr Leu Ser Val
305                 310                 315                 320
```

```
Glu Glu Gln Ala Leu Phe Asn Thr Gln Thr Arg Arg Gln Ile Tyr Glu
                325                 330                 335

Tyr Ser Leu Gln
            340


<210> SEQ ID NO 11
<211> LENGTH: 867
<212> TYPE: DNA
<213> ORGANISM: Yersinia pestis

<400> SEQUENCE: 11

atgatcggac caatatcaca aataaatatc tccggtggct tatcagaaaa agagaccagt      60

tctttaatca gtaatgaaga gcttaaaaat atcataacac agttggaaac tgatatatcg     120

gatggatcct ggttccataa aaattattca cgtatggatg tagaagtcat gcccgcattg     180

gtaatccagg cgaacaataa atatccggaa atgaatctta atcttgttac atctccattg     240

gacctttcaa tagaaataaa aaacgtcata gaaaatggag ttagatcttc ccgcttcata     300

attaacatgg gggaaggtgg aatacatttc agtgtaattg attacaaaca tataaatggg     360

aaaacatctc tgatattgtt tgaaccagca aactttaaca gtatggggcc agcgatgctg     420

gcaataagga caaaaacggc tattgaacgt tatcaattac ctgattgcca tttctccatg     480

gtggaaatgg atattcagcg aagctcatct gaatgtggta tttttagttt ggcactggca     540

aaaaaacttt acatcgagag agatagcctg ttgaaaatac atgaagataa tataaaaggt     600

atattaagtg atggtgaaaa tcctttaccc cacgataagt tggacccgta tctcccggta     660

actttttaca aacatactca aggtaaaaaa cgtcttaatg aatatttaaa tactaacccg     720

cagggagttg gtactgttgt taacaaaaaa aatgaaacca tcgttaatag atttgataac     780

aataaatcca ttgtagatgg aaaggaatta tcagtttcgg tacataaaaa gagaatagct     840

gaatataaaa cacttctcaa agtataa                                         867


<210> SEQ ID NO 12
<211> LENGTH: 288
<212> TYPE: PRT
<213> ORGANISM: Yersinia pestis

<400> SEQUENCE: 12

Met Ile Gly Pro Ile Ser Gln Ile Asn Ile Ser Gly Gly Leu Ser Glu
1               5                   10                  15

Lys Glu Thr Ser Ser Leu Ile Ser Asn Glu Glu Leu Lys Asn Ile Ile
            20                  25                  30

Thr Gln Leu Glu Thr Asp Ile Ser Asp Gly Ser Trp Phe His Lys Asn
        35                  40                  45

Tyr Ser Arg Met Asp Val Glu Val Met Pro Ala Leu Val Ile Gln Ala
    50                  55                  60

Asn Asn Lys Tyr Pro Glu Met Asn Leu Asn Leu Val Thr Ser Pro Leu
65                  70                  75                  80

Asp Leu Ser Ile Glu Ile Lys Asn Val Ile Glu Asn Gly Val Arg Ser
                85                  90                  95

Ser Arg Phe Ile Ile Asn Met Gly Glu Gly Gly Ile His Phe Ser Val
            100                 105                 110

Ile Asp Tyr Lys His Ile Asn Gly Lys Thr Ser Leu Ile Leu Phe Glu
        115                 120                 125

Pro Ala Asn Phe Asn Ser Met Gly Pro Ala Met Leu Ala Ile Arg Thr
    130                 135                 140
```

Lys Thr Ala Ile Glu Arg Tyr Gln Leu Pro Asp Cys His Phe Ser Met
145 150 155 160

Val Glu Met Asp Ile Gln Arg Ser Ser Ser Glu Cys Gly Ile Phe Ser
165 170 175

Leu Ala Leu Ala Lys Lys Leu Tyr Ile Glu Arg Asp Ser Leu Leu Lys
180 185 190

Ile His Glu Asp Asn Ile Lys Gly Ile Leu Ser Asp Gly Glu Asn Pro
195 200 205

Leu Pro His Asp Lys Leu Asp Pro Tyr Leu Pro Val Thr Phe Tyr Lys
210 215 220

His Thr Gln Gly Lys Lys Arg Leu Asn Glu Tyr Leu Asn Thr Asn Pro
225 230 235 240

Gln Gly Val Gly Thr Val Val Asn Lys Lys Asn Glu Thr Ile Val Asn
245 250 255

Arg Phe Asp Asn Asn Lys Ser Ile Val Asp Gly Lys Glu Leu Ser Val
260 265 270

Ser Val His Lys Lys Arg Ile Ala Glu Tyr Lys Thr Leu Leu Lys Val
275 280 285

<210> SEQ ID NO 13
<211> LENGTH: 981
<212> TYPE: DNA
<213> ORGANISM: Escherichia coli

<400> SEQUENCE: 13
atgctttcac cgataaggac aactttccat aactcagtaa atatagtgca gagttcaccc 60
tgtcaaacgg tttcttttgc aggaaaggaa tatgagttaa aggtcattga tgaaaaaacg 120
cctattcttt ttcagtggtt tgaacctaat cctgaacgat ataagaaaga tgaggttcca 180
atagttaata ctaagcagca tccctattta gataatgtca caaatgcggc aaggatagag 240
agtgatcgta tgataggtat ttttgttgat ggcgattttt cagtcaacca aaagactgct 300
ttttcaaaat tggaacgaga ttttgaaaat gtaatgataa tctatcggga agatgttgac 360
ttcagtatgt atgacagaaa actatcagat atttatcatg atattatatg tgaacaaagg 420
ttacgaactg aagacaaaag agatgaatac ttgttgaatc tgttagagaa agagctgagg 480
gaaatttcaa aggcgcagga ttctttgatt tctatgtatg caaagaaaag aaatcatgca 540
tggtttgatt tcttcagaaa tttagcctta ttaaaagcag gagagatatt caggtgcaca 600
tataatacaa agaatcacgg tatttcattc ggggaggggt gtatctatct tgatatggat 660
atgatactta caggtaagct tggtacaata tatgctcctg atggaatttc aatgcatgtg 720
gatcgtcgta atgatagtgt aaatattgaa aatagtgcaa taattgttaa ccgtagtaat 780
catcctgctc tacttgaggg actttctttt atgcatagta aagtagatgc tcatccatat 840
tatgatggtt tggggaaagg agttaagaaa tattttaatt ttacaccatt acataattat 900
aatcattttt gtgactttat tgagtttaac caccctaata taatcatgaa cacaagtcag 960
tatacatgca gttcatggta a 981

<210> SEQ ID NO 14
<211> LENGTH: 326
<212> TYPE: PRT
<213> ORGANISM: Escherichia coli

<400> SEQUENCE: 14

Met Leu Ser Pro Ile Arg Thr Thr Phe His Asn Ser Val Asn Ile Val

```
1               5                   10                  15

Gln Ser Ser Pro Cys Gln Thr Val Ser Phe Ala Gly Lys Glu Tyr Glu
            20                  25                  30

Leu Lys Val Ile Asp Glu Lys Thr Pro Ile Leu Phe Gln Trp Phe Glu
        35                  40                  45

Pro Asn Pro Glu Arg Tyr Lys Lys Asp Glu Val Pro Ile Val Asn Thr
    50                  55                  60

Lys Gln His Pro Tyr Leu Asp Asn Val Thr Asn Ala Ala Arg Ile Glu
65                  70                  75                  80

Ser Asp Arg Met Ile Gly Ile Phe Val Asp Gly Asp Phe Ser Val Asn
                85                  90                  95

Gln Lys Thr Ala Phe Ser Lys Leu Glu Arg Asp Phe Glu Asn Val Met
            100                 105                 110

Ile Ile Tyr Arg Glu Asp Val Asp Phe Ser Met Tyr Asp Arg Lys Leu
        115                 120                 125

Ser Asp Ile Tyr His Asp Ile Ile Cys Glu Gln Arg Leu Arg Thr Glu
    130                 135                 140

Asp Lys Arg Asp Glu Tyr Leu Leu Asn Leu Leu Glu Lys Glu Leu Arg
145                 150                 155                 160

Glu Ile Ser Lys Ala Gln Asp Ser Leu Ile Ser Met Tyr Ala Lys Lys
                165                 170                 175

Arg Asn His Ala Trp Phe Asp Phe Phe Arg Asn Leu Ala Leu Leu Lys
            180                 185                 190

Ala Gly Glu Ile Phe Arg Cys Thr Tyr Asn Thr Lys Asn His Gly Ile
        195                 200                 205

Ser Phe Gly Glu Gly Cys Ile Tyr Leu Asp Met Asp Met Ile Leu Thr
    210                 215                 220

Gly Lys Leu Gly Thr Ile Tyr Ala Pro Asp Gly Ile Ser Met His Val
225                 230                 235                 240

Asp Arg Arg Asn Asp Ser Val Asn Ile Glu Asn Ser Ala Ile Ile Val
                245                 250                 255

Asn Arg Ser Asn His Pro Ala Leu Leu Glu Gly Leu Ser Phe Met His
            260                 265                 270

Ser Lys Val Asp Ala His Pro Tyr Tyr Asp Gly Leu Gly Lys Gly Val
        275                 280                 285

Lys Lys Tyr Phe Asn Phe Thr Pro Leu His Asn Tyr Asn His Phe Cys
    290                 295                 300

Asp Phe Ile Glu Phe Asn His Pro Asn Ile Ile Met Asn Thr Ser Gln
305                 310                 315                 320

Tyr Thr Cys Ser Ser Trp
                325


<210> SEQ ID NO 15
<211> LENGTH: 993
<212> TYPE: DNA
<213> ORGANISM: Escherichia coli

<400> SEQUENCE: 15

atgaaaattc cctcattaca gtccaacttc aacttttccg ccccggcagg atactctgct      60

cccattgctc ctaatcgtgc tgaaaatgcc tatgcggatt acgttttgga tataggtaag     120

cgaataccac tttccgcagc agatttaagc aacgtatacg aaagtgtaat acgcgccgtc     180

catgacagcc gtagcaggct tatcgatcag catacagtcg atatgatcgg caacactgta     240

cttgatgctt tgagccgatc acagacattt cgtgatgccg taagctatgg cattcataat     300
```

```
gagaaggtac acattggttg cattaaatac agaaacgaat acgagcttaa cgaagaatct    360

tctgtcaaaa ttgatgatat tcaatcacta acctgtaacg aattatatga atatgatgtc    420

gggcaagagc caattttccc catttgcgaa gcaggagaaa acgataacga agagccttat    480

gtcagtttta gtgttgcgcc agatactgac tcttatgaga tgccatcgtg gcaggaagga    540

ctgattcacg agattattca tcatgttact ggatctagcg atccatctgg agatagtaat    600

atagagttag gacccaccga gattctcgca cgtcgtgtcg ctcaagaact gggatggagt    660

gttcccgact tcaaaggata tgcagagcca gaacgtgaag ctcatcttag gctacgtaac    720

ctgaatgccc ttcgacaggc tgccatgagg catgaagaga atgagagggc tttcttcgaa    780

aggctgggta cgatcagtga ccgatatgag gcgagtcctg atttcacaga gtattccgct    840

gtgtctaaca taggatacgg atttatccag caacatgatt ttcctggatt ggctatcaac    900

gataatttac aggatgcaaa tcagatccaa ctgtatcatg gcgcccctta tatttttaca    960

tttggggatg tggacaaaca caatcagcaa tga                                 993
```

```
<210> SEQ ID NO 16
<211> LENGTH: 330
<212> TYPE: PRT
<213> ORGANISM: Escherichia coli

<400> SEQUENCE: 16

Met Lys Ile Pro Ser Leu Gln Ser Asn Phe Asn Phe Ser Ala Pro Ala
1               5                   10                  15

Gly Tyr Ser Ala Pro Ile Ala Pro Asn Arg Ala Glu Asn Ala Tyr Ala
            20                  25                  30

Asp Tyr Val Leu Asp Ile Gly Lys Arg Ile Pro Leu Ser Ala Ala Asp
        35                  40                  45

Leu Ser Asn Val Tyr Glu Ser Val Ile Arg Ala Val His Asp Ser Arg
    50                  55                  60

Ser Arg Leu Ile Asp Gln His Thr Val Asp Met Ile Gly Asn Thr Val
65                  70                  75                  80

Leu Asp Ala Leu Ser Arg Ser Gln Thr Phe Arg Asp Ala Val Ser Tyr
                85                  90                  95

Gly Ile His Asn Glu Lys Val His Ile Gly Cys Ile Lys Tyr Arg Asn
            100                 105                 110

Glu Tyr Glu Leu Asn Glu Glu Ser Ser Val Lys Ile Asp Asp Ile Gln
        115                 120                 125

Ser Leu Thr Cys Asn Glu Leu Tyr Glu Tyr Asp Val Gly Gln Glu Pro
    130                 135                 140

Ile Phe Pro Ile Cys Glu Ala Gly Glu Asn Asp Asn Glu Glu Pro Tyr
145                 150                 155                 160

Val Ser Phe Ser Val Ala Pro Asp Thr Asp Ser Tyr Glu Met Pro Ser
                165                 170                 175

Trp Gln Glu Gly Leu Ile His Glu Ile Ile His His Val Thr Gly Ser
            180                 185                 190

Ser Asp Pro Ser Gly Asp Ser Asn Ile Glu Leu Gly Pro Thr Glu Ile
        195                 200                 205

Leu Ala Arg Arg Val Ala Gln Glu Leu Gly Trp Ser Val Pro Asp Phe
    210                 215                 220

Lys Gly Tyr Ala Glu Pro Glu Arg Glu Ala His Leu Arg Leu Arg Asn
225                 230                 235                 240

Leu Asn Ala Leu Arg Gln Ala Ala Met Arg His Glu Glu Asn Glu Arg
```

-continued

```
                245                 250                 255

Ala Phe Phe Glu Arg Leu Gly Thr Ile Ser Asp Arg Tyr Glu Ala Ser
            260                 265                 270

Pro Asp Phe Thr Glu Tyr Ser Ala Val Ser Asn Ile Gly Tyr Gly Phe
        275                 280                 285

Ile Gln Gln His Asp Phe Pro Gly Leu Ala Ile Asn Asp Asn Leu Gln
    290                 295                 300

Asp Ala Asn Gln Ile Gln Leu Tyr His Gly Ala Pro Tyr Ile Phe Thr
305                 310                 315                 320

Phe Gly Asp Val Asp Lys His Asn Gln Gln
                325                 330


<210> SEQ ID NO 17
<211> LENGTH: 675
<212> TYPE: DNA
<213> ORGANISM: Escherichia coli

<400> SEQUENCE: 17

atgattaatc ctgttactaa tactcagggc gtgtccccta taaatactaa atatgctgaa      60

catgtggtga aaaatattta cccggaaatt aaacatgatt actttaatga atcacccaat     120

atatatgata agaagtatat atccggtata accagaggag tagctgaact aaaacaggaa     180

gaatttgtta acgagaaagc cagacggttt tcttatatga agactatgta ttctgtatgt     240

ccagaagcgt ttgaacctat ttccagaaat gaagccagta caccggaagg aagctggcta     300

acagttatat ccggaaaacg cccaatgggg cagttttctg tagatagttt atacaatcct     360

gatttacatg cattatgtga gcttccggac atttgttgta agatcttccc taaagaaaat     420

aatgattttt tatacatagt tgttgtgtac agaaatgaca gccctctagg agaacaacgg     480

gcaaatagat ttatagaatt atataatata aaaagagata tcatgcagga attaaattat     540

gagttaccag agttaaaggc agtaaaatct gaaatgatta tcgcacgtga aatgggagaa     600

atctttagct acatgcctgg ggaaatagac agttatatga aatacataaa taataaactt     660

tctaaaattg agtag                                                      675


<210> SEQ ID NO 18
<211> LENGTH: 224
<212> TYPE: PRT
<213> ORGANISM: Escherichia coli

<400> SEQUENCE: 18

Met Ile Asn Pro Val Thr Asn Thr Gln Gly Val Ser Pro Ile Asn Thr
1               5                   10                  15

Lys Tyr Ala Glu His Val Val Lys Asn Ile Tyr Pro Glu Ile Lys His
            20                  25                  30

Asp Tyr Phe Asn Glu Ser Pro Asn Ile Tyr Asp Lys Lys Tyr Ile Ser
        35                  40                  45

Gly Ile Thr Arg Gly Val Ala Glu Leu Lys Gln Glu Glu Phe Val Asn
    50                  55                  60

Glu Lys Ala Arg Arg Phe Ser Tyr Met Lys Thr Met Tyr Ser Val Cys
65                  70                  75                  80

Pro Glu Ala Phe Glu Pro Ile Ser Arg Asn Glu Ala Ser Thr Pro Glu
                85                  90                  95

Gly Ser Trp Leu Thr Val Ile Ser Gly Lys Arg Pro Met Gly Gln Phe
            100                 105                 110

Ser Val Asp Ser Leu Tyr Asn Pro Asp Leu His Ala Leu Cys Glu Leu
```

```
        115                 120                 125

Pro Asp Ile Cys Cys Lys Ile Phe Pro Lys Glu Asn Asn Asp Phe Leu
    130                 135                 140

Tyr Ile Val Val Val Tyr Arg Asn Asp Ser Pro Leu Gly Glu Gln Arg
145                 150                 155                 160

Ala Asn Arg Phe Ile Glu Leu Tyr Asn Ile Lys Arg Asp Ile Met Gln
                165                 170                 175

Glu Leu Asn Tyr Glu Leu Pro Glu Leu Lys Ala Val Lys Ser Glu Met
            180                 185                 190

Ile Ile Ala Arg Glu Met Gly Glu Ile Phe Ser Tyr Met Pro Gly Glu
        195                 200                 205

Ile Asp Ser Tyr Met Lys Tyr Ile Asn Asn Lys Leu Ser Lys Ile Glu
    210                 215                 220


<210> SEQ ID NO 19
<211> LENGTH: 252
<212> TYPE: DNA
<213> ORGANISM: Shigella flexneri

<400> SEQUENCE: 19

atgagtgtta cagtaccgaa tgatgattgg acattgagtt cattatctga aacttttgat      60

gatggaactc aaacattaca aggtgaacta acattggcac tagataaatt agctaaaaat     120

ccttcgaatc cacagttgct ggctgaatac caaagtaaat tatctgaata tacattatat     180

aggaacgcgc aatccaatac agtgaaagtg attaaggatg ttgatgctgc aattattcaa     240

aacttcagat aa                                                         252


<210> SEQ ID NO 20
<211> LENGTH: 83
<212> TYPE: PRT
<213> ORGANISM: Shigella flexneri

<400> SEQUENCE: 20

Met Ser Val Thr Val Pro Asn Asp Asp Trp Thr Leu Ser Ser Leu Ser
1               5                   10                  15

Glu Thr Phe Asp Asp Gly Thr Gln Thr Leu Gln Gly Glu Leu Thr Leu
            20                  25                  30

Ala Leu Asp Lys Leu Ala Lys Asn Pro Ser Asn Pro Gln Leu Leu Ala
        35                  40                  45

Glu Tyr Gln Ser Lys Leu Ser Glu Tyr Thr Leu Tyr Arg Asn Ala Gln
    50                  55                  60

Ser Asn Thr Val Lys Val Ile Lys Asp Val Asp Ala Ala Ile Ile Gln
65                  70                  75                  80

Asn Phe Arg


<210> SEQ ID NO 21
<211> LENGTH: 243
<212> TYPE: DNA
<213> ORGANISM: Salmonella enterica

<400> SEQUENCE: 21

atggcaacac cttggtcagg ctatctggat gacgtctcag caaaatttga tacgggcgtt      60

gataatctac aaacgcaggt aacagaggcg ctggataaat tagcagcaaa accctccgat     120

ccggcgctac tggcggcgta tcagagtaag ctctcggaat ataacttgta ccgtaacgcg     180

caatcgaaca cggtaaaagt ctttaaggat attgatgctg ccattattca gaacttccgt     240
```

taa 243

<210> SEQ ID NO 22
<211> LENGTH: 80
<212> TYPE: PRT
<213> ORGANISM: Salmonella enterica

<400> SEQUENCE: 22

Met Ala Thr Pro Trp Ser Gly Tyr Leu Asp Asp Val Ser Ala Lys Phe
1 5 10 15

Asp Thr Gly Val Asp Asn Leu Gln Thr Gln Val Thr Glu Ala Leu Asp
20 25 30

Lys Leu Ala Ala Lys Pro Ser Asp Pro Ala Leu Leu Ala Ala Tyr Gln
35 40 45

Ser Lys Leu Ser Glu Tyr Asn Leu Tyr Arg Asn Ala Gln Ser Asn Thr
50 55 60

Val Lys Val Phe Lys Asp Ile Asp Ala Ala Ile Ile Gln Asn Phe Arg
65 70 75 80

<210> SEQ ID NO 23
<211> LENGTH: 264
<212> TYPE: DNA
<213> ORGANISM: Yersinia pestis

<400> SEQUENCE: 23
atgagtaact tctctggatt tacgaaagga accgatatcg cagacttaga tgcggtggct 60
caaacgctca agaagccagc agacgatgca aacaaagcgg ttaatgactc gatagcagca 120
ttgaaagata agcctgacaa cccggcgcta cttgctgact tacaacattc aattaataaa 180
tggtcggtaa tttacaatat aaactcaacc atagttcgta gcatgaaaga cttaatgcaa 240
ggcatcctac agaagttccc ataa 264

<210> SEQ ID NO 24
<211> LENGTH: 87
<212> TYPE: PRT
<213> ORGANISM: Yersinia pestis

<400> SEQUENCE: 24

Met Ser Asn Phe Ser Gly Phe Thr Lys Gly Thr Asp Ile Ala Asp Leu
1 5 10 15

Asp Ala Val Ala Gln Thr Leu Lys Lys Pro Ala Asp Asp Ala Asn Lys
20 25 30

Ala Val Asn Asp Ser Ile Ala Ala Leu Lys Asp Lys Pro Asp Asn Pro
35 40 45

Ala Leu Leu Ala Asp Leu Gln His Ser Ile Asn Lys Trp Ser Val Ile
50 55 60

Tyr Asn Ile Asn Ser Thr Ile Val Arg Ser Met Lys Asp Leu Met Gln
65 70 75 80

Gly Ile Leu Gln Lys Phe Pro
85

<210> SEQ ID NO 25
<211> LENGTH: 222
<212> TYPE: DNA
<213> ORGANISM: Escherichia coli

<400> SEQUENCE: 25
atgaatttat ctgaaattac tcaacaaatg ggtgaagtag gtaaaacgct gagcgattct 60
gtgccagagt tacttaatag caccgatttg gttaatgacc ctgaaaaaat gttagagttg 120
cagtttgcgg ttcagcaata ttctgcttat gttaacgtag aaagtggaat gttgaaaacg 180
ataaaagatc tggtctcaac catttctaac cgtagttttt aa 222

<210> SEQ ID NO 26
<211> LENGTH: 73
<212> TYPE: PRT
<213> ORGANISM: Escherichia coli

<400> SEQUENCE: 26

Met Asn Leu Ser Glu Ile Thr Gln Gln Met Gly Glu Val Gly Lys Thr
1 5 10 15

Leu Ser Asp Ser Val Pro Glu Leu Leu Asn Ser Thr Asp Leu Val Asn
20 25 30

Asp Pro Glu Lys Met Leu Glu Leu Gln Phe Ala Val Gln Gln Tyr Ser
35 40 45

Ala Tyr Val Asn Val Glu Ser Gly Met Leu Lys Thr Ile Lys Asp Leu
50 55 60

Val Ser Thr Ile Ser Asn Arg Ser Phe
65 70

<210> SEQ ID NO 27
<211> LENGTH: 294
<212> TYPE: DNA
<213> ORGANISM: Shigella flexneri

<400> SEQUENCE: 27
atgaattaca tttatccagt caatcaggtt gatattatca aagccagtga ttttcaatct 60
caagagatat caagtctgga agacgtcgtg tcggctaaat atagtgatat taagatggat 120
acagatattc aagtatcaca aataatggag atggtaagca atccagaatc attaaaccca 180
gaatctttgg ccaagttaca gacgacgctc tcaaattatt caataggagt atcattagct 240
ggcacgttag caagaaaaac agtttcggct gttgaaactt tattaaagtc ttaa 294

<210> SEQ ID NO 28
<211> LENGTH: 97
<212> TYPE: PRT
<213> ORGANISM: Shigella flexneri

<400> SEQUENCE: 28

Met Asn Tyr Ile Tyr Pro Val Asn Gln Val Asp Ile Ile Lys Ala Ser
1 5 10 15

Asp Phe Gln Ser Gln Glu Ile Ser Ser Leu Glu Asp Val Val Ser Ala
20 25 30

Lys Tyr Ser Asp Ile Lys Met Asp Thr Asp Ile Gln Val Ser Gln Ile
35 40 45

Met Glu Met Val Ser Asn Pro Glu Ser Leu Asn Pro Glu Ser Leu Ala
50 55 60

Lys Leu Gln Thr Thr Leu Ser Asn Tyr Ser Ile Gly Val Ser Leu Ala
65 70 75 80

Gly Thr Leu Ala Arg Lys Thr Val Ser Ala Val Glu Thr Leu Leu Lys
85 90 95

Ser

<210> SEQ ID NO 29
<211> LENGTH: 306
<212> TYPE: DNA

<213> ORGANISM: Salmonella enterica

<400> SEQUENCE: 29
atgtcgattg caactattgt ccctgagaat gccgttatag ggcaggcggt caatatcagg 60
tctatggaaa cggacattgt ctcgctggat gaccggctac tccaggcttt ttctggttcg 120
gcgattgcca cggctgtgga taaacagacg attaccaaca ggattgagga ccctaatctg 180
gtgacggatc ctaaagagct ggctatttcg caagagatga tttcagatta taacctgtat 240
gtttctatgg tcagtaccct tactcgtaaa ggagtcgggg ctgttgaaac gctattacgc 300
tcatga 306

<210> SEQ ID NO 30
<211> LENGTH: 101
<212> TYPE: PRT
<213> ORGANISM: Salmonella enterica

<400> SEQUENCE: 30

Met Ser Ile Ala Thr Ile Val Pro Glu Asn Ala Val Ile Gly Gln Ala
1 5 10 15

Val Asn Ile Arg Ser Met Glu Thr Asp Ile Val Ser Leu Asp Asp Arg
20 25 30

Leu Leu Gln Ala Phe Ser Gly Ser Ala Ile Ala Thr Ala Val Asp Lys
35 40 45

Gln Thr Ile Thr Asn Arg Ile Glu Asp Pro Asn Leu Val Thr Asp Pro
50 55 60

Lys Glu Leu Ala Ile Ser Gln Glu Met Ile Ser Asp Tyr Asn Leu Tyr
65 70 75 80

Val Ser Met Val Ser Thr Leu Thr Arg Lys Gly Val Gly Ala Val Glu
85 90 95

Thr Leu Leu Arg Ser
100

<210> SEQ ID NO 31
<211> LENGTH: 348
<212> TYPE: DNA
<213> ORGANISM: Yersinia pestis

<400> SEQUENCE: 31
atgccgaaca tagaaatagc tcaggccgat gaggtgatca taaccacgct ggaggaatta 60
gggccggcag agccaacaac tgaccaaata atgcgctttg atgcggcaat gtcagaagat 120
acgcagggac tgggccattc actcctcaag gaggttagtg atattcagaa gtcttttaag 180
acggttaaaa gtgacttaca cactaagctg gctgtttcag ttgataatcc caacgacctg 240
atgctaatgc aatggtcact tatccgtata acaatccaag aagaacttat cgccaagact 300
gccgggcgaa tgagccaaaa tgttgaaacc ttgtcgaagg gggggtga 348

<210> SEQ ID NO 32
<211> LENGTH: 115
<212> TYPE: PRT
<213> ORGANISM: Yersinia pestis

<400> SEQUENCE: 32

Met Pro Asn Ile Glu Ile Ala Gln Ala Asp Glu Val Ile Ile Thr Thr
1 5 10 15

Leu Glu Glu Leu Gly Pro Ala Glu Pro Thr Thr Asp Gln Ile Met Arg
20 25 30

-continued

```
Phe Asp Ala Ala Met Ser Glu Asp Thr Gln Gly Leu Gly His Ser Leu
        35                  40                  45

Leu Lys Glu Val Ser Asp Ile Gln Lys Ser Phe Lys Thr Val Lys Ser
    50                  55                  60

Asp Leu His Thr Lys Leu Ala Val Ser Val Asp Asn Pro Asn Asp Leu
65                  70                  75                  80

Met Leu Met Gln Trp Ser Leu Ile Arg Ile Thr Ile Gln Glu Glu Leu
                85                  90                  95

Ile Ala Lys Thr Ala Gly Arg Met Ser Gln Asn Val Glu Thr Leu Ser
            100                 105                 110

Lys Gly Gly
        115


<210> SEQ ID NO 33
<211> LENGTH: 429
<212> TYPE: DNA
<213> ORGANISM: Escherichia coli

<400> SEQUENCE: 33

atggatgtat tatgcccttg cctctttcat aaaaagaggc taacagtaaa tatgaacaac     60

attaatcaat cggaaaacat taatattcaa ttaaataaag cgccccaaac aaatttcgtt    120

gatgagcata cctcgttagc ctcagccccc tctgcggcag gtgcggctca gtttcttgat    180

caattactcc ctaaaacagc gggagtgtct tctccagaac aagtgttgat tgaagaaatt    240

aaaaagagac atcttgcaac aatgaacagc gatctcagtt tcgatgctct atctgcaggt    300

gggctctcgc cagaagacgt gctcacctta caaaagaatg tgctcaacgc aaacgtcaac    360

gttgatgtcg tatctaagtt agcaagcctc ctttcaacat cggttacaaa attagtttcg    420

atgcaataa                                                            429


<210> SEQ ID NO 34
<211> LENGTH: 142
<212> TYPE: PRT
<213> ORGANISM: Escherichia coli

<400> SEQUENCE: 34

Met Asp Val Leu Cys Pro Cys Leu Phe His Lys Lys Arg Leu Thr Val
1               5                   10                  15

Asn Met Asn Asn Ile Asn Gln Ser Glu Asn Ile Asn Ile Gln Leu Asn
            20                  25                  30

Lys Ala Pro Gln Thr Asn Phe Val Asp Glu His Thr Ser Leu Ala Ser
        35                  40                  45

Ala Pro Ser Ala Ala Gly Ala Ala Gln Phe Leu Asp Gln Leu Leu Pro
    50                  55                  60

Lys Thr Ala Gly Val Ser Ser Pro Glu Gln Val Leu Ile Glu Glu Ile
65                  70                  75                  80

Lys Lys Arg His Leu Ala Thr Met Asn Ser Asp Leu Ser Phe Asp Ala
                85                  90                  95

Leu Ser Ala Gly Gly Leu Ser Pro Glu Asp Val Leu Thr Leu Gln Lys
            100                 105                 110

Asn Val Leu Asn Ala Asn Val Asn Val Asp Val Val Ser Lys Leu Ala
        115                 120                 125

Ser Leu Leu Ser Thr Ser Val Thr Lys Leu Val Ser Met Gln
    130                 135                 140


<210> SEQ ID NO 35
```

<211> LENGTH: 1149
<212> TYPE: DNA
<213> ORGANISM: Shigella flexneri

<400> SEQUENCE: 35
atgttgcaaa agcaattttg caacaaacta ctgcttgata caaataagga gaatgttatg 60
gaaattcaaa acacaaaacc aacccagact ttatatacag atatatccac aaaacaaact 120
caaagttctt ccgaaacaca aaaatcacaa aattatcagc agattgcagc gcatattcca 180
cttaatgtcg gtaaaaatcc cgtattaaca accacattaa atgatgatca acttttaaag 240
ttatcagagc aggttcagca tgattcagaa atcattgctc gccttactga caaaaagatg 300
aaagatcttt cagagatgag tcacaccctt actccagaga acactctgga tatttccagt 360
ctttcttcta atgctgtttc tttaattatt agtgtagccg ttctactttc tgctctccgc 420
actgcagaaa ctaaattggg ctctcaattg tcattgattg cgttcgatgc tacaaaatca 480
gctgcagaga acattgttcg gcaaggcctg gcagccctat catcaagcat tactggagca 540
gtcacacaag taggtataac gggtatcggt gccaaaaaaa cgcattcagg gattagcgac 600
caaaaaggag ccttaagaaa gaaccttgcc actgctcaat ctcttgaaaa agagcttgca 660
ggttctaaat tagggttaaa taaacaaata gatacaaata tcacctcacc acaaactaac 720
tctagcacaa aatttttagg taaaaataaa ctggcgccag ataatatatc cctgtcaact 780
gaacataaaa cttctcttag ttctcccgat atttctttgc aggataaaat tgacacccag 840
agaagaactt acgagctcaa taccctttct gcgcagcaaa aacaaaacat tggccgtgca 900
acaatggaaa catcagccgt tgctggtaat atatccacat caggagggcg ttatgcatct 960
gctcttgaag aagaagaaca actaatcagt caggccagca gtaaacaagc agaggaagca 1020
tcccaagtat ctaaagaagc atcccaagcg acaaatcaat taatacaaaa attattgaat 1080
ataattgaca gcatcaacca atcaaagaat tcggcagcca gtcagattgc tggtaacatt 1140
cgagcttaa 1149

<210> SEQ ID NO 36
<211> LENGTH: 382
<212> TYPE: PRT
<213> ORGANISM: Shigella flexneri

<400> SEQUENCE: 36

Met Leu Gln Lys Gln Phe Cys Asn Lys Leu Leu Leu Asp Thr Asn Lys
1 5 10 15

Glu Asn Val Met Glu Ile Gln Asn Thr Lys Pro Thr Gln Thr Leu Tyr
20 25 30

Thr Asp Ile Ser Thr Lys Gln Thr Gln Ser Ser Ser Glu Thr Gln Lys
35 40 45

Ser Gln Asn Tyr Gln Gln Ile Ala Ala His Ile Pro Leu Asn Val Gly
50 55 60

Lys Asn Pro Val Leu Thr Thr Thr Leu Asn Asp Asp Gln Leu Leu Lys
65 70 75 80

Leu Ser Glu Gln Val Gln His Asp Ser Glu Ile Ile Ala Arg Leu Thr
85 90 95

Asp Lys Lys Met Lys Asp Leu Ser Glu Met Ser His Thr Leu Thr Pro
100 105 110

Glu Asn Thr Leu Asp Ile Ser Ser Leu Ser Ser Asn Ala Val Ser Leu
115 120 125

Ile Ile Ser Val Ala Val Leu Leu Ser Ala Leu Arg Thr Ala Glu Thr

```
    130                 135                 140

Lys Leu Gly Ser Gln Leu Ser Leu Ile Ala Phe Asp Ala Thr Lys Ser
145                 150                 155                 160

Ala Ala Glu Asn Ile Val Arg Gln Gly Leu Ala Ala Leu Ser Ser Ser
                165                 170                 175

Ile Thr Gly Ala Val Thr Gln Val Gly Ile Thr Gly Ile Gly Ala Lys
            180                 185                 190

Lys Thr His Ser Gly Ile Ser Asp Gln Lys Gly Ala Leu Arg Lys Asn
        195                 200                 205

Leu Ala Thr Ala Gln Ser Leu Glu Lys Glu Leu Ala Gly Ser Lys Leu
    210                 215                 220

Gly Leu Asn Lys Gln Ile Asp Thr Asn Ile Thr Ser Pro Gln Thr Asn
225                 230                 235                 240

Ser Ser Thr Lys Phe Leu Gly Lys Asn Lys Leu Ala Pro Asp Asn Ile
                245                 250                 255

Ser Leu Ser Thr Glu His Lys Thr Ser Leu Ser Ser Pro Asp Ile Ser
            260                 265                 270

Leu Gln Asp Lys Ile Asp Thr Gln Arg Arg Thr Tyr Glu Leu Asn Thr
        275                 280                 285

Leu Ser Ala Gln Gln Lys Gln Asn Ile Gly Arg Ala Thr Met Glu Thr
    290                 295                 300

Ser Ala Val Ala Gly Asn Ile Ser Thr Ser Gly Gly Arg Tyr Ala Ser
305                 310                 315                 320

Ala Leu Glu Glu Glu Glu Gln Leu Ile Ser Gln Ala Ser Ser Lys Gln
                325                 330                 335

Ala Glu Glu Ala Ser Gln Val Ser Lys Glu Ala Ser Gln Ala Thr Asn
            340                 345                 350

Gln Leu Ile Gln Lys Leu Leu Asn Ile Ile Asp Ser Ile Asn Gln Ser
        355                 360                 365

Lys Asn Ser Ala Ala Ser Gln Ile Ala Gly Asn Ile Arg Ala
    370                 375                 380
```

<210> SEQ ID NO 37
<211> LENGTH: 1782
<212> TYPE: DNA
<213> ORGANISM: Salmonella enterica

<400> SEQUENCE: 37

```
atggtaaatg acgcaagtag cattagccgt agcggatata cccaaaatcc gcgcctcgct     60

gaggcggctt ttgaaggcgt tcgtaagaac acggactttt taaaagcggc ggataaagct    120

tttaaagatg tggtggcaac gaaagcgggc gaccttaaag ccggaacaaa gtccggcgag    180

agcgctatta atacggtggg tctaaagccg cctacggacg ccgcccggga aaaactctcc    240

agcgaagggc aattgacatt actgcttggc aagttaatga ccctactggg cgatgtttcg    300

ctgtctcaac tggagtctcg tctggcggta tggcaggcga tgattgagtc acaaaaagag    360

atggggattc aggtatcgaa agaattccag acggctctgg gagaggctca ggaggcgacg    420

gatctctatg aagccagtat caaaaagacg gataccgcca agagtgttta tgacgctgcg    480

accaaaaaac tgacgcaggc gcaaaataaa ttgcaatcgc tggacccggc tgaccccggc    540

tatgcacaag ctgaagccgc ggtagaacag gccggaaaag aagcgacaga ggcgaaagag    600

gccttagata aggccacgga tgcgacggtt aaagcaggca cagacgccaa agcgaaagcc    660

gagaaagcgg ataacattct gaccaaattc cagggaacgg ctaatgccgc ctctcagaat    720
```

-continued

```
caggtttccc agggtgagca ggataatctg tcaaatgtcg cccgcctcac tatgctcatg    780

gccatgttta ttgagattgt gggcaaaaat acggaagaaa gcctgcaaaa cgatcttgcg    840

cttttcaacg ccttgcagga agggcgtcag gcggagatgg aaaagaaatc ggctgaattc    900

caggaagaga cgcgcaaagc cgaggaaacg aaccgcatta tgggatgtat cgggaaagtc    960

ctcggcgcgc tgctaaccat tgtcagcgtt gtggccgctg tttttaccgg tggggcgagt   1020

ctggcgctgg ctgcggtggg acttgcggta atggtggccg atgaaattgt gaaggcggcg   1080

acgggagtgt cgtttattca gcaggcgcta aacccgatta tggagcatgt gctgaagccg   1140

ttaatggagc tgattggcaa ggcgattacc aaagcgctgg aaggattagg cgtcgataag   1200

aaaacggcag agatggccgg cagcattgtt ggtgcgattg tcgccgctat tgccatggtg   1260

gcggtcattg tggtggtcgc agttgtcggg aaaggcgcgg cggcgaaact gggtaacgcg   1320

ctgagcaaaa tgatgggcga aacgattaag aagttggtgc ctaacgtgct gaaacagttg   1380

gcgcaaaacg gcagcaaact ctttacccag gggatgcaac gtattactag cggtctgggt   1440

aatgtgggta gcaagatggg cctgcaaacg aatgccttaa gtaaagagct ggtaggtaat   1500

accctaaata aagtggcgtt gggcatggaa gtcacgaata ccgcagccca gtcagccggt   1560

ggtgttgccg agggcgtatt tattaaaaat gccagcgagg cgcttgctga ttttatgctc   1620

gcccgttttg ccatggatca gattcagcag tggcttaaac aatccgtaga aatatttggt   1680

gaaaaccaga aggtaacggc ggaactgcaa aaagccatgt cttctgcggt acagcaaaat   1740

gcggatgctt cgcgttttat tctgcgccag agtcgcgcat aa                      1782
```

```
<210> SEQ ID NO 38
<211> LENGTH: 593
<212> TYPE: PRT
<213> ORGANISM: Salmonella enterica

<400> SEQUENCE: 38

Met Val Asn Asp Ala Ser Ser Ile Ser Arg Ser Gly Tyr Thr Gln Asn
1               5                   10                  15

Pro Arg Leu Ala Glu Ala Ala Phe Glu Gly Val Arg Lys Asn Thr Asp
            20                  25                  30

Phe Leu Lys Ala Ala Asp Lys Ala Phe Lys Asp Val Val Ala Thr Lys
        35                  40                  45

Ala Gly Asp Leu Lys Ala Gly Thr Lys Ser Gly Glu Ser Ala Ile Asn
    50                  55                  60

Thr Val Gly Leu Lys Pro Pro Thr Asp Ala Ala Arg Glu Lys Leu Ser
65                  70                  75                  80

Ser Glu Gly Gln Leu Thr Leu Leu Leu Gly Lys Leu Met Thr Leu Leu
                85                  90                  95

Gly Asp Val Ser Leu Ser Gln Leu Glu Ser Arg Leu Ala Val Trp Gln
            100                 105                 110

Ala Met Ile Glu Ser Gln Lys Glu Met Gly Ile Gln Val Ser Lys Glu
        115                 120                 125

Phe Gln Thr Ala Leu Gly Glu Ala Gln Glu Ala Thr Asp Leu Tyr Glu
    130                 135                 140

Ala Ser Ile Lys Lys Thr Asp Thr Ala Lys Ser Val Tyr Asp Ala Ala
145                 150                 155                 160

Thr Lys Lys Leu Thr Gln Ala Gln Asn Lys Leu Gln Ser Leu Asp Pro
                165                 170                 175

Ala Asp Pro Gly Tyr Ala Gln Ala Glu Ala Ala Val Glu Gln Ala Gly
            180                 185                 190
```

-continued

```
Lys Glu Ala Thr Glu Ala Lys Glu Ala Leu Asp Lys Ala Thr Asp Ala
        195                 200                 205

Thr Val Lys Ala Gly Thr Asp Ala Lys Ala Lys Ala Glu Lys Ala Asp
    210                 215                 220

Asn Ile Leu Thr Lys Phe Gln Gly Thr Ala Asn Ala Ala Ser Gln Asn
225                 230                 235                 240

Gln Val Ser Gln Gly Glu Gln Asp Asn Leu Ser Asn Val Ala Arg Leu
                245                 250                 255

Thr Met Leu Met Ala Met Phe Ile Glu Ile Val Gly Lys Asn Thr Glu
            260                 265                 270

Glu Ser Leu Gln Asn Asp Leu Ala Leu Phe Asn Ala Leu Gln Glu Gly
        275                 280                 285

Arg Gln Ala Glu Met Glu Lys Lys Ser Ala Glu Phe Gln Glu Glu Thr
    290                 295                 300

Arg Lys Ala Glu Glu Thr Asn Arg Ile Met Gly Cys Ile Gly Lys Val
305                 310                 315                 320

Leu Gly Ala Leu Leu Thr Ile Val Ser Val Val Ala Ala Val Phe Thr
                325                 330                 335

Gly Gly Ala Ser Leu Ala Leu Ala Ala Val Gly Leu Ala Val Met Val
            340                 345                 350

Ala Asp Glu Ile Val Lys Ala Ala Thr Gly Val Ser Phe Ile Gln Gln
        355                 360                 365

Ala Leu Asn Pro Ile Met Glu His Val Leu Lys Pro Leu Met Glu Leu
    370                 375                 380

Ile Gly Lys Ala Ile Thr Lys Ala Leu Glu Gly Leu Gly Val Asp Lys
385                 390                 395                 400

Lys Thr Ala Glu Met Ala Gly Ser Ile Val Gly Ala Ile Val Ala Ala
                405                 410                 415

Ile Ala Met Val Ala Val Ile Val Val Val Ala Val Val Gly Lys Gly
            420                 425                 430

Ala Ala Ala Lys Leu Gly Asn Ala Leu Ser Lys Met Met Gly Glu Thr
        435                 440                 445

Ile Lys Lys Leu Val Pro Asn Val Leu Lys Gln Leu Ala Gln Asn Gly
    450                 455                 460

Ser Lys Leu Phe Thr Gln Gly Met Gln Arg Ile Thr Ser Gly Leu Gly
465                 470                 475                 480

Asn Val Gly Ser Lys Met Gly Leu Gln Thr Asn Ala Leu Ser Lys Glu
                485                 490                 495

Leu Val Gly Asn Thr Leu Asn Lys Val Ala Leu Gly Met Glu Val Thr
            500                 505                 510

Asn Thr Ala Ala Gln Ser Ala Gly Gly Val Ala Glu Gly Val Phe Ile
        515                 520                 525

Lys Asn Ala Ser Glu Ala Leu Ala Asp Phe Met Leu Ala Arg Phe Ala
    530                 535                 540

Met Asp Gln Ile Gln Gln Trp Leu Lys Gln Ser Val Glu Ile Phe Gly
545                 550                 555                 560

Glu Asn Gln Lys Val Thr Ala Glu Leu Gln Lys Ala Met Ser Ser Ala
                565                 570                 575

Val Gln Gln Asn Ala Asp Ala Ser Arg Phe Ile Leu Arg Gln Ser Arg
            580                 585                 590

Ala
```

<210> SEQ ID NO 39
<211> LENGTH: 1230
<212> TYPE: DNA
<213> ORGANISM: Salmonella enterica

<400> SEQUENCE: 39
atgttaatta gtaatgtggg aataaatccc gccgcttatt taaataatca ttctgttgag 60
aatagttcac agacagcttc gcaatccgtt agcgctaaag atattctgaa tagtattggt 120
attagcagca gtaaagtcag tgacctgggg ttgagtccta cactgagcgc gcctgcgcca 180
ggggtattaa cgcaaacccc cggaacgatc acgtcctttt taaaagccag tattcaaaat 240
accgacatga atcaggattt gaatgctctg gcaaataatg tcacgactaa agcgaatgag 300
gttgtgcaaa cccagttacg cgagcagcag gcagaagtcg gaaagttttt tgatattagc 360
ggaatgtctt ccagtgccgt tgcgctgttg gctgccgcga atacgttaat gctgacgttg 420
aaccaggctg atagcaaact gtctggtaag ttgtcattag tcagttttga tgcagctaaa 480
acgacggcaa gctccatgat gcgcgaaggg atgaatgcgt tgtccggtag tatttcccag 540
agcgcgcttc agttggggat cactggcgtg ggcgccaaac tggaatataa ggggctgcag 600
aatgaaagag gcgcgcttaa acataatgcc gcgaagatcg ataaactgac cactgaaagc 660
cacagtatta aaaacgtgct gaacgggcag aatagcgtca aactcggtgc tgaaggcgtc 720
gattctctga aatcgttaaa tatgaagaaa accggtaccg atgcgacgaa aaatcttaat 780
gatgcgacgc ttaaatctaa tgccggaacc agcgccacgg aaagtctggg tattaaagac 840
agtaataaac aaatctcccc tgaacatcag gctattctgt cgaaacgtct tgagtctgtc 900
gaatccgata ttcgtcttga gcagaatacc atggatatga cccgaatcga tgcgcgcaag 960
atgcagatga cgggcgatct gattatgaag aactcggtca cggtcggtgg tattgcaggg 1020
gcgtccgggc agtacgccgc tactcaggaa cgttccgagc agcaaattag ccaggtgaat 1080
aaccgggttg ccagcaccgc atcggacgaa gcccgtgaaa gttcacgtaa atcgaccagc 1140
ctgattcagg aaatgctgaa aacaatggag agcattaacc agtcgaaagc atccgcactc 1200
gctgctatcg caggcaatat tcgcgcttaa 1230

<210> SEQ ID NO 40
<211> LENGTH: 409
<212> TYPE: PRT
<213> ORGANISM: Salmonella enterica

<400> SEQUENCE: 40

Met Leu Ile Ser Asn Val Gly Ile Asn Pro Ala Ala Tyr Leu Asn Asn
1 5 10 15

His Ser Val Glu Asn Ser Ser Gln Thr Ala Ser Gln Ser Val Ser Ala
20 25 30

Lys Asp Ile Leu Asn Ser Ile Gly Ile Ser Ser Ser Lys Val Ser Asp
35 40 45

Leu Gly Leu Ser Pro Thr Leu Ser Ala Pro Ala Pro Gly Val Leu Thr
50 55 60

Gln Thr Pro Gly Thr Ile Thr Ser Phe Leu Lys Ala Ser Ile Gln Asn
65 70 75 80

Thr Asp Met Asn Gln Asp Leu Asn Ala Leu Ala Asn Asn Val Thr Thr
85 90 95

Lys Ala Asn Glu Val Val Gln Thr Gln Leu Arg Glu Gln Gln Ala Glu
100 105 110

Val Gly Lys Phe Phe Asp Ile Ser Gly Met Ser Ser Ser Ala Val Ala

```
        115                 120                 125

Leu Leu Ala Ala Ala Asn Thr Leu Met Leu Thr Leu Asn Gln Ala Asp
    130                 135                 140

Ser Lys Leu Ser Gly Lys Leu Ser Leu Val Ser Phe Asp Ala Ala Lys
145                 150                 155                 160

Thr Thr Ala Ser Ser Met Met Arg Glu Gly Met Asn Ala Leu Ser Gly
                165                 170                 175

Ser Ile Ser Gln Ser Ala Leu Gln Leu Gly Ile Thr Gly Val Gly Ala
            180                 185                 190

Lys Leu Glu Tyr Lys Gly Leu Gln Asn Glu Arg Gly Ala Leu Lys His
        195                 200                 205

Asn Ala Ala Lys Ile Asp Lys Leu Thr Thr Glu Ser His Ser Ile Lys
    210                 215                 220

Asn Val Leu Asn Gly Gln Asn Ser Val Lys Leu Gly Ala Glu Gly Val
225                 230                 235                 240

Asp Ser Leu Lys Ser Leu Asn Met Lys Lys Thr Gly Thr Asp Ala Thr
                245                 250                 255

Lys Asn Leu Asn Asp Ala Thr Leu Lys Ser Asn Ala Gly Thr Ser Ala
            260                 265                 270

Thr Glu Ser Leu Gly Ile Lys Asp Ser Asn Lys Gln Ile Ser Pro Glu
        275                 280                 285

His Gln Ala Ile Leu Ser Lys Arg Leu Glu Ser Val Glu Ser Asp Ile
    290                 295                 300

Arg Leu Glu Gln Asn Thr Met Asp Met Thr Arg Ile Asp Ala Arg Lys
305                 310                 315                 320

Met Gln Met Thr Gly Asp Leu Ile Met Lys Asn Ser Val Thr Val Gly
                325                 330                 335

Gly Ile Ala Gly Ala Ser Gly Gln Tyr Ala Ala Thr Gln Glu Arg Ser
            340                 345                 350

Glu Gln Gln Ile Ser Gln Val Asn Asn Arg Val Ala Ser Thr Ala Ser
        355                 360                 365

Asp Glu Ala Arg Glu Ser Ser Arg Lys Ser Thr Ser Leu Ile Gln Glu
    370                 375                 380

Met Leu Lys Thr Met Glu Ser Ile Asn Gln Ser Lys Ala Ser Ala Leu
385                 390                 395                 400

Ala Ala Ile Ala Gly Asn Ile Arg Ala
                405
```

<210> SEQ ID NO 41
<211> LENGTH: 1206
<212> TYPE: DNA
<213> ORGANISM: Yersinia enterocolitica

<400> SEQUENCE: 41

```
atgagtgcgt tgataaccca tgatcgctca acgccagtaa ctggaagtct acttccctac      60

gtcgagacac cagcgcccgc ccccccttcag actcaacaag tcgcgggaga actgaaggat     120

aaaaatggtg gggtgagttc tcagggcgta cagctccctg caccactagc agtggttgcc     180

agccaagtca ctgaaggaca acagcaagaa atcactaaat tattggagtc ggtcacccgc     240

ggcacggcag gatctcaact gatatcaaat tatgtttcag tgctaacgaa ttttacgctc     300

gcttcacctg atacatttga gattgagtta ggtaagctag tttctaattt agaagaagta     360

cgcaaagaca taaaaatcgc tgatattcag cgtcttcatg aacaaaacat gaagaaaatt     420

gaagagaatc aagagaaaat caaagaaaca gaagagaatg ccaagcaagt caagaaatcc     480
```

```
ggcatggcat caaagatttt tggctggctc agcgccatag cctcagtggt tatcggtgcc    540

atcatggtgg cctcaggggt aggagccgtt gccggtgcaa tgatgattgc ctcaggcgta    600

attgggatgg cgaatatggc tgtgaaacaa gcggcggaag atggcctgat atcccaagag    660

gcaatgcaag tattagggcc gatactcact gcgattgaag tcgcattgac tgtagtttca    720

accgtaatga cctttggcgg ttcggcacta aaatgcctgg ctgatattgg cgcaaaactc    780

ggtgctaaca ccgcaagtct tgctgctaaa ggagccgagt tttcggccaa agttgcccaa    840

atttcgacag gcatatcaaa cactgtcggg aatgcagtga ctaaattagg gggcagtttt    900

ggtagtttaa caatgagcca tgtaatccgt acaggatcac aggcaacaca agtcgccgtt    960

ggtgtgggca gcggaataac tcagaccatc aataataaaa aacaagctga tttacaacat   1020

aataacgctg atttggcctt gaacaaggca gacatggcag cgttacaaag tattattgac   1080

cgactcaaag aagagttatc ccatttgtca gagtcacatc aacaagtgat ggaactgatt   1140

ttccagatga ttaatgcaaa aggtgacatg ctgcataatt tggccggcag accccatact   1200

gtttaa                                                               1206


<210> SEQ ID NO 42
<211> LENGTH: 401
<212> TYPE: PRT
<213> ORGANISM: Yersinia enterocolitica

<400> SEQUENCE: 42

Met Ser Ala Leu Ile Thr His Asp Arg Ser Thr Pro Val Thr Gly Ser
1               5                   10                  15

Leu Leu Pro Tyr Val Glu Thr Pro Ala Pro Ala Pro Leu Gln Thr Gln
            20                  25                  30

Gln Val Ala Gly Glu Leu Lys Asp Lys Asn Gly Gly Val Ser Ser Gln
        35                  40                  45

Gly Val Gln Leu Pro Ala Pro Leu Ala Val Val Ala Ser Gln Val Thr
    50                  55                  60

Glu Gly Gln Gln Gln Glu Ile Thr Lys Leu Leu Glu Ser Val Thr Arg
65                  70                  75                  80

Gly Thr Ala Gly Ser Gln Leu Ile Ser Asn Tyr Val Ser Val Leu Thr
                85                  90                  95

Asn Phe Thr Leu Ala Ser Pro Asp Thr Phe Glu Ile Glu Leu Gly Lys
            100                 105                 110

Leu Val Ser Asn Leu Glu Glu Val Arg Lys Asp Ile Lys Ile Ala Asp
        115                 120                 125

Ile Gln Arg Leu His Glu Gln Asn Met Lys Lys Ile Glu Glu Asn Gln
    130                 135                 140

Glu Lys Ile Lys Glu Thr Glu Glu Asn Ala Lys Gln Val Lys Lys Ser
145                 150                 155                 160

Gly Met Ala Ser Lys Ile Phe Gly Trp Leu Ser Ala Ile Ala Ser Val
                165                 170                 175

Val Ile Gly Ala Ile Met Val Ala Ser Gly Val Gly Ala Val Ala Gly
            180                 185                 190

Ala Met Met Ile Ala Ser Gly Val Ile Gly Met Ala Asn Met Ala Val
        195                 200                 205

Lys Gln Ala Ala Glu Asp Gly Leu Ile Ser Gln Glu Ala Met Gln Val
    210                 215                 220

Leu Gly Pro Ile Leu Thr Ala Ile Glu Val Ala Leu Thr Val Val Ser
225                 230                 235                 240
```

-continued

Thr Val Met Thr Phe Gly Gly Ser Ala Leu Lys Cys Leu Ala Asp Ile
245 250 255

Gly Ala Lys Leu Gly Ala Asn Thr Ala Ser Leu Ala Ala Lys Gly Ala
260 265 270

Glu Phe Ser Ala Lys Val Ala Gln Ile Ser Thr Gly Ile Ser Asn Thr
275 280 285

Val Gly Asn Ala Val Thr Lys Leu Gly Gly Ser Phe Gly Ser Leu Thr
290 295 300

Met Ser His Val Ile Arg Thr Gly Ser Gln Ala Thr Gln Val Ala Val
305 310 315 320

Gly Val Gly Ser Gly Ile Thr Gln Thr Ile Asn Asn Lys Lys Gln Ala
325 330 335

Asp Leu Gln His Asn Asn Ala Asp Leu Ala Leu Asn Lys Ala Asp Met
340 345 350

Ala Ala Leu Gln Ser Ile Ile Asp Arg Leu Lys Glu Glu Leu Ser His
355 360 365

Leu Ser Glu Ser His Gln Gln Val Met Glu Leu Ile Phe Gln Met Ile
370 375 380

Asn Ala Lys Gly Asp Met Leu His Asn Leu Ala Gly Arg Pro His Thr
385 390 395 400

Val

<210> SEQ ID NO 43
<211> LENGTH: 921
<212> TYPE: DNA
<213> ORGANISM: Yersinia enterocolitica

<400> SEQUENCE: 43
atgacaataa atatcaagac agacagccca attatcacga ccggttcaca gattgatgcc 60
atcactacag agacagtcgg gcaaagcggt gaggttaaaa aaacagaaga cacccgtcat 120
gaagcacaag caataaagag tagcgaggca agcttatctc ggtcacaagt gcctgaattg 180
atcaaaccga gtcagggaat caatgttgca ttactgagta aaagccaggg agatcttaat 240
ggtactttaa gtatcttgtt gttgctgttg gaactggcac gtaaagcgcg agaaatgggt 300
ttgcaacaaa gggatataga aaataaagct gctattactg cccaaaagga gcaggtagcg 360
gagatggtca gcggtgcaaa actgatgatc gccatggcgg tggtgtctgg catcatggct 420
gctacttcta cggttgctag tgctttttct atagcgaaag aggtgaaaat agttaaacag 480
gaacaaattc taaacagtaa tattgctggc cgcgatcaac ttattgatac aaaaatgcaa 540
caaatgagta acaccagtga taaagcggta agcagagagg atatcgggag aatatggaaa 600
ccagagcagg tagcggatca aaataagctg gcattattgg ataaagaatt cagaatgacc 660
gactcaaaag ccaatgcgtt taatgccgca acgcagccgt taggacaaat ggcaaacagt 720
gcgattcaag ttcatcaagg gtattctcaa gccgaggtca aagagaaaga agtcaatgca 780
agtattgctg ccaacgagaa gcaaaaagcc gaagaggcga tgaactataa tgataacttt 840
atgaaagatg tcctgcgctt gattgaacaa tatgttagca gtcatactca cgccatgaaa 900
gccgcttttg gtgttgtctg a 921

<210> SEQ ID NO 44
<211> LENGTH: 306
<212> TYPE: PRT
<213> ORGANISM: Yersinia enterocolitica

<400> SEQUENCE: 44

```
Met Thr Ile Asn Ile Lys Thr Asp Ser Pro Ile Ile Thr Thr Gly Ser
1               5                   10                  15

Gln Ile Asp Ala Ile Thr Thr Glu Thr Val Gly Gln Ser Gly Glu Val
            20                  25                  30

Lys Lys Thr Glu Asp Thr Arg His Glu Ala Gln Ala Ile Lys Ser Ser
        35                  40                  45

Glu Ala Ser Leu Ser Arg Ser Gln Val Pro Glu Leu Ile Lys Pro Ser
    50                  55                  60

Gln Gly Ile Asn Val Ala Leu Leu Ser Lys Ser Gln Gly Asp Leu Asn
65                  70                  75                  80

Gly Thr Leu Ser Ile Leu Leu Leu Leu Leu Glu Leu Ala Arg Lys Ala
                85                  90                  95

Arg Glu Met Gly Leu Gln Gln Arg Asp Ile Glu Asn Lys Ala Ala Ile
            100                 105                 110

Thr Ala Gln Lys Glu Gln Val Ala Glu Met Val Ser Gly Ala Lys Leu
        115                 120                 125

Met Ile Ala Met Ala Val Val Ser Gly Ile Met Ala Ala Thr Ser Thr
    130                 135                 140

Val Ala Ser Ala Phe Ser Ile Ala Lys Glu Val Lys Ile Val Lys Gln
145                 150                 155                 160

Glu Gln Ile Leu Asn Ser Asn Ile Ala Gly Arg Asp Gln Leu Ile Asp
                165                 170                 175

Thr Lys Met Gln Gln Met Ser Asn Thr Ser Asp Lys Ala Val Ser Arg
            180                 185                 190

Glu Asp Ile Gly Arg Ile Trp Lys Pro Glu Gln Val Ala Asp Gln Asn
        195                 200                 205

Lys Leu Ala Leu Leu Asp Lys Glu Phe Arg Met Thr Asp Ser Lys Ala
    210                 215                 220

Asn Ala Phe Asn Ala Ala Thr Gln Pro Leu Gly Gln Met Ala Asn Ser
225                 230                 235                 240

Ala Ile Gln Val His Gln Gly Tyr Ser Gln Ala Glu Val Lys Glu Lys
                245                 250                 255

Glu Val Asn Ala Ser Ile Ala Ala Asn Glu Lys Gln Lys Ala Glu Glu
            260                 265                 270

Ala Met Asn Tyr Asn Asp Asn Phe Met Lys Asp Val Leu Arg Leu Ile
        275                 280                 285

Glu Gln Tyr Val Ser Ser His Thr His Ala Met Lys Ala Ala Phe Gly
    290                 295                 300

Val Val
305
```

<210> SEQ ID NO 45
<211> LENGTH: 555
<212> TYPE: DNA
<213> ORGANISM: Mycobacterium tuberculosis

<400> SEQUENCE: 45

```
gtggacttgc ccggaaatga ctttgacagc aacgatttcg acgccgtgga tctctggggt     60

gccgacggcg cggagggctg gactgcggat ccgattattg gcgtcgggtc ggcggcgacc    120

ccggacaccg gacccgacct ggacaatgcc cacggtcagg cggagacgga caccgaacaa    180

gagatcgcgc tttttaccgt gacgaatccc ccacgcacgg tgtcggtatc gacgctgatg    240

gacggccgga ttgaccatgt cgagctgtcg gccagggtgg cctggatgag tgagtcgcag    300
```

ctcgcttctg agatcctggt gattgccgac ctggcgcggc agaaggcgca gtcggcccag 360
tacgccttca tccttgacag gatgagtcaa caggtcgatg cagatgaaca ccgcgtcgca 420
ctgctacgta agaccgtggg cgaaacctgg gggttaccat cgccggaaga agccgcggca 480
gcagaagctg aggtgttcgc gacgcgctac agcgacgatt gtccagcacc agacgacgag 540
agcgatccat ggtga 555

<210> SEQ ID NO 46
<211> LENGTH: 184
<212> TYPE: PRT
<213> ORGANISM: Mycobacterium tuberculosis

<400> SEQUENCE: 46

Met Asp Leu Pro Gly Asn Asp Phe Asp Ser Asn Asp Phe Asp Ala Val
1 5 10 15

Asp Leu Trp Gly Ala Asp Gly Ala Glu Gly Trp Thr Ala Asp Pro Ile
20 25 30

Ile Gly Val Gly Ser Ala Ala Thr Pro Asp Thr Gly Pro Asp Leu Asp
35 40 45

Asn Ala His Gly Gln Ala Glu Thr Asp Thr Glu Gln Glu Ile Ala Leu
50 55 60

Phe Thr Val Thr Asn Pro Pro Arg Thr Val Ser Val Ser Thr Leu Met
65 70 75 80

Asp Gly Arg Ile Asp His Val Glu Leu Ser Ala Arg Val Ala Trp Met
85 90 95

Ser Glu Ser Gln Leu Ala Ser Glu Ile Leu Val Ile Ala Asp Leu Ala
100 105 110

Arg Gln Lys Ala Gln Ser Ala Gln Tyr Ala Phe Ile Leu Asp Arg Met
115 120 125

Ser Gln Gln Val Asp Ala Asp Glu His Arg Val Ala Leu Leu Arg Lys
130 135 140

Thr Val Gly Glu Thr Trp Gly Leu Pro Ser Pro Glu Glu Ala Ala Ala
145 150 155 160

Ala Glu Ala Glu Val Phe Ala Thr Arg Tyr Ser Asp Asp Cys Pro Ala
165 170 175

Pro Asp Asp Glu Ser Asp Pro Trp
180

<210> SEQ ID NO 47
<211> LENGTH: 945
<212> TYPE: DNA
<213> ORGANISM: Escherichia coli

<400> SEQUENCE: 47
atgaatacta ttgattatac taatcaagta atgacggtta attctgtttc ggagaatact 60
accggctcta atgcaattac cgcatctgct attaattcat ctttgcttac cgatggtaag 120
gtcgatgttt ctaaactgat gctggaaatt caaaaactcc tgggcaagat ggtgcgtata 180
ttgcaggatt accaacagca acagttgtcg cagagctatc agatccaact ggccgttttt 240
gagagccaga ataaagccat tgatgaaaaa aaggccgctg caacagccgc tctggttggt 300
ggggctattt catcagtatt ggggatctta ggctcttttg cagcaattaa cagtgctacg 360
aaaggcgcga gtgatattgc tcaacaaacc gcctctacat cttctaaggc tattgatgcg 420
gcttctgata ctgcgactaa aacgttgact aaggcaacgg aaagcgttgc tgatgctgtt 480

-continued

```
gaagatgcat ccagcgtgat gcagcaagcg atgactacag caacgagagc ggccagccgt    540

acatctgacg ttgcagatga cattgccgat tctgctcaga gagcttctca gctggctgaa    600

aacgctgcag atgccgctca gaaggcaagt cgggcaagcc gctttatggc tgcagtagat    660

aagattactg gctctacacc atttattgcc gttaccagtc ttgccgaagg cacgaagaca    720

ttgccaacaa cggtatctga atcagtcaaa tctaaccatg agattagcga acagcgttat    780

aagtctgtgg agaacttcca gcagggtaat ttggatctgt ataagcaaga agttcgcaga    840

gcgcaggatg atatcgctag ccgtctgcgt gatatgacaa cagccgctcg cgatctcact    900

gatcttcaga atcgtatggg tcaatcggtt cgcttagctg ggtaa                    945
```

```
<210> SEQ ID NO 48
<211> LENGTH: 314
<212> TYPE: PRT
<213> ORGANISM: Escherichia coli

<400> SEQUENCE: 48

Met Asn Thr Ile Asp Tyr Thr Asn Gln Val Met Thr Val Asn Ser Val
1               5                   10                  15

Ser Glu Asn Thr Thr Gly Ser Asn Ala Ile Thr Ala Ser Ala Ile Asn
            20                  25                  30

Ser Ser Leu Leu Thr Asp Gly Lys Val Asp Val Ser Lys Leu Met Leu
        35                  40                  45

Glu Ile Gln Lys Leu Leu Gly Lys Met Val Arg Ile Leu Gln Asp Tyr
    50                  55                  60

Gln Gln Gln Gln Leu Ser Gln Ser Tyr Gln Ile Gln Leu Ala Val Phe
65                  70                  75                  80

Glu Ser Gln Asn Lys Ala Ile Asp Glu Lys Lys Ala Ala Ala Thr Ala
                85                  90                  95

Ala Leu Val Gly Gly Ala Ile Ser Ser Val Leu Gly Ile Leu Gly Ser
            100                 105                 110

Phe Ala Ala Ile Asn Ser Ala Thr Lys Gly Ala Ser Asp Ile Ala Gln
        115                 120                 125

Gln Thr Ala Ser Thr Ser Ser Lys Ala Ile Asp Ala Ala Ser Asp Thr
    130                 135                 140

Ala Thr Lys Thr Leu Thr Lys Ala Thr Glu Ser Val Ala Asp Ala Val
145                 150                 155                 160

Glu Asp Ala Ser Ser Val Met Gln Gln Ala Met Thr Thr Ala Thr Arg
                165                 170                 175

Ala Ala Ser Arg Thr Ser Asp Val Ala Asp Asp Ile Ala Asp Ser Ala
            180                 185                 190

Gln Arg Ala Ser Gln Leu Ala Glu Asn Ala Ala Asp Ala Ala Gln Lys
        195                 200                 205

Ala Ser Arg Ala Ser Arg Phe Met Ala Ala Val Asp Lys Ile Thr Gly
    210                 215                 220

Ser Thr Pro Phe Ile Ala Val Thr Ser Leu Ala Glu Gly Thr Lys Thr
225                 230                 235                 240

Leu Pro Thr Thr Val Ser Glu Ser Val Lys Ser Asn His Glu Ile Ser
                245                 250                 255

Glu Gln Arg Tyr Lys Ser Val Glu Asn Phe Gln Gln Gly Asn Leu Asp
            260                 265                 270

Leu Tyr Lys Gln Glu Val Arg Arg Ala Gln Asp Asp Ile Ala Ser Arg
        275                 280                 285

Leu Arg Asp Met Thr Thr Ala Ala Arg Asp Leu Thr Asp Leu Gln Asn
```

290 295 300

Arg Met Gly Gln Ser Val Arg Leu Ala Gly
305 310

<210> SEQ ID NO 49
<211> LENGTH: 999
<212> TYPE: DNA
<213> ORGANISM: Shigella flexneri

<400> SEQUENCE: 49
atgaatataa caactctgac taatagtatt tccacctcat cattcagtcc aaacaatacc 60
aacggttcat caaccgaaac agttaattct gatataaaaa caacgaccag ttctcatcct 120
gtaagttccc ttactatgct caacgacacc cttcataata tcagaacaac aaatcaggca 180
ttaaagaaag agctttcaca aaaaacgttg actaaaacat cgctagaaga aatagcatta 240
cattcatctc agattagcat ggatgtaaat aaatccgctc aactattgga tattctttcc 300
aggaacgaat atccaattaa taaagacgca agagaattat tacattcagc cccgaaagaa 360
gccgagcttg atggagatca aatgatatct catagagaac tgtgggctaa aattgcaaac 420
tccatcaatg atattaatga acagtatctg aaagtatatg aacatgccgt tagttcatat 480
actcaaatgt atcaagattt tagcgctgtt ctttccagtc ttgccggctg gatctctccc 540
ggaggtaacg acggaaactc cgtgaaatta caagtcaact cgcttaaaaa ggcattggaa 600
gaactcaagg aaaaatataa agataaaccg ctatatccag caaataatac tgttagtcag 660
gaacaagcaa ataaatggct tacagaatta ggtggaacaa tcggcaaggt atctcaaaaa 720
aacgggggat atgttgtcag tataaacatg accccaatag acaatatgtt aaaaagctta 780
gataatctag gtggaaatgg cgaggttgtg ctagataatg caaaatatca ggcatggaat 840
gccggattct ctgccgaaga tgaaacaatg aaaaataatc ttcaaacttt agttcaaaaa 900
tacagtaatg ccaatagtat ttttgataat ttagtaaagg ttttgagtag tacaataagc 960
tcatgtacag atacagataa actttttctc catttctga 999

<210> SEQ ID NO 50
<211> LENGTH: 332
<212> TYPE: PRT
<213> ORGANISM: Shigella flexneri

<400> SEQUENCE: 50

Met Asn Ile Thr Thr Leu Thr Asn Ser Ile Ser Thr Ser Ser Phe Ser
1 5 10 15

Pro Asn Asn Thr Asn Gly Ser Ser Thr Glu Thr Val Asn Ser Asp Ile
20 25 30

Lys Thr Thr Thr Ser Ser His Pro Val Ser Ser Leu Thr Met Leu Asn
35 40 45

Asp Thr Leu His Asn Ile Arg Thr Thr Asn Gln Ala Leu Lys Lys Glu
50 55 60

Leu Ser Gln Lys Thr Leu Thr Lys Thr Ser Leu Glu Glu Ile Ala Leu
65 70 75 80

His Ser Ser Gln Ile Ser Met Asp Val Asn Lys Ser Ala Gln Leu Leu
85 90 95

Asp Ile Leu Ser Arg Asn Glu Tyr Pro Ile Asn Lys Asp Ala Arg Glu
100 105 110

Leu Leu His Ser Ala Pro Lys Glu Ala Glu Leu Asp Gly Asp Gln Met
115 120 125

-continued

Ile Ser His Arg Glu Leu Trp Ala Lys Ile Ala Asn Ser Ile Asn Asp
    130                 135                 140

Ile Asn Glu Gln Tyr Leu Lys Val Tyr Glu His Ala Val Ser Ser Tyr
145                 150                 155                 160

Thr Gln Met Tyr Gln Asp Phe Ser Ala Val Leu Ser Ser Leu Ala Gly
                165                 170                 175

Trp Ile Ser Pro Gly Gly Asn Asp Gly Asn Ser Val Lys Leu Gln Val
            180                 185                 190

Asn Ser Leu Lys Lys Ala Leu Glu Glu Leu Lys Glu Lys Tyr Lys Asp
        195                 200                 205

Lys Pro Leu Tyr Pro Ala Asn Asn Thr Val Ser Gln Glu Gln Ala Asn
    210                 215                 220

Lys Trp Leu Thr Glu Leu Gly Gly Thr Ile Gly Lys Val Ser Gln Lys
225                 230                 235                 240

Asn Gly Gly Tyr Val Val Ser Ile Asn Met Thr Pro Ile Asp Asn Met
                245                 250                 255

Leu Lys Ser Leu Asp Asn Leu Gly Gly Asn Gly Glu Val Val Leu Asp
            260                 265                 270

Asn Ala Lys Tyr Gln Ala Trp Asn Ala Gly Phe Ser Ala Glu Asp Glu
        275                 280                 285

Thr Met Lys Asn Asn Leu Gln Thr Leu Val Gln Lys Tyr Ser Asn Ala
    290                 295                 300

Asn Ser Ile Phe Asp Asn Leu Val Lys Val Leu Ser Ser Thr Ile Ser
305                 310                 315                 320

Ser Cys Thr Asp Thr Asp Lys Leu Phe Leu His Phe
                325                 330

<210> SEQ ID NO 51
<211> LENGTH: 1032
<212> TYPE: DNA
<213> ORGANISM: Salmonella enterica

<400> SEQUENCE: 51
atgcttaata ttcaaaatta ttccgcttct cctcatccgg ggatcgttgc cgaacggccg 60
cagactccct cggcgagcga gcacgtcgag actgccgtgg taccgtctac cacagaacat 120
cgcggtacag atatcatttc attatcgcag gcggctacta aaatccacca ggcacagcag 180
acgctgcagt caacgccacc gatctctgaa gagaataatg acgagcgcac gctggcgcgc 240
cagcagttga ccagcagcct gaatgcgctg gcgaagtccg gcgtgtcatt atccgcagaa 300
caaaatgaga acctgcggag cgcgttttct gcgccgacgt cggccttatt tagcgcttcg 360
cctatggcgc agccgagaac aaccatttct gatgctgaga tttgggatat ggtttcccaa 420
aatatatcgg cgataggtga cagctatctg ggcgtttatg aaaacgttgt cgcagtctat 480
accgattttt atcaggcctt cagtgatatt ctttccaaaa tgggaggctg gttattacca 540
ggtaaggacg gtaataccgt taagctagat gttacctcac tcaaaaatga tttaaacagt 600
ttagtcaata aatataatca aataaacagt aataccgttt tatttccagc gcagtcaggc 660
agcggcgtta aagtagccac tgaagcggaa gcgagacagt ggctcagtga attgaattta 720
ccgaatagct gcctgaaatc ttatggatcc ggttatgtcg tcaccgttga tctgacgcca 780
ttacaaaaaa tggttcagga tattgatggt ttaggcgcgc cgggaaaaga ctcaaaactc 840
gaaatggata acgccaaata tcaagcctgg cagtcgggtt ttaaagcgca ggaagaaaat 900
atgaaaacca cattacagac gctgacgcaa aaatatagca atgccaattc attgtacgac 960
aacctggtaa aagtgctgag cagtacgata agtagcagcc tggaaaccgc caaaagcttc 1020
ctgcaaggat aa 1032

<210> SEQ ID NO 52
<211> LENGTH: 343
<212> TYPE: PRT
<213> ORGANISM: Salmonella enterica

<400> SEQUENCE: 52

Met Leu Asn Ile Gln Asn Tyr Ser Ala Ser Pro His Pro Gly Ile Val
1 5 10 15

Ala Glu Arg Pro Gln Thr Pro Ser Ala Ser Glu His Val Glu Thr Ala
20 25 30

Val Val Pro Ser Thr Thr Glu His Arg Gly Thr Asp Ile Ile Ser Leu
35 40 45

Ser Gln Ala Ala Thr Lys Ile His Gln Ala Gln Gln Thr Leu Gln Ser
50 55 60

Thr Pro Pro Ile Ser Glu Glu Asn Asn Asp Glu Arg Thr Leu Ala Arg
65 70 75 80

Gln Gln Leu Thr Ser Ser Leu Asn Ala Leu Ala Lys Ser Gly Val Ser
85 90 95

Leu Ser Ala Glu Gln Asn Glu Asn Leu Arg Ser Ala Phe Ser Ala Pro
100 105 110

Thr Ser Ala Leu Phe Ser Ala Ser Pro Met Ala Gln Pro Arg Thr Thr
115 120 125

Ile Ser Asp Ala Glu Ile Trp Asp Met Val Ser Gln Asn Ile Ser Ala
130 135 140

Ile Gly Asp Ser Tyr Leu Gly Val Tyr Glu Asn Val Val Ala Val Tyr
145 150 155 160

Thr Asp Phe Tyr Gln Ala Phe Ser Asp Ile Leu Ser Lys Met Gly Gly
165 170 175

Trp Leu Leu Pro Gly Lys Asp Gly Asn Thr Val Lys Leu Asp Val Thr
180 185 190

Ser Leu Lys Asn Asp Leu Asn Ser Leu Val Asn Lys Tyr Asn Gln Ile
195 200 205

Asn Ser Asn Thr Val Leu Phe Pro Ala Gln Ser Gly Ser Gly Val Lys
210 215 220

Val Ala Thr Glu Ala Glu Ala Arg Gln Trp Leu Ser Glu Leu Asn Leu
225 230 235 240

Pro Asn Ser Cys Leu Lys Ser Tyr Gly Ser Gly Tyr Val Val Thr Val
245 250 255

Asp Leu Thr Pro Leu Gln Lys Met Val Gln Asp Ile Asp Gly Leu Gly
260 265 270

Ala Pro Gly Lys Asp Ser Lys Leu Glu Met Asp Asn Ala Lys Tyr Gln
275 280 285

Ala Trp Gln Ser Gly Phe Lys Ala Gln Glu Glu Asn Met Lys Thr Thr
290 295 300

Leu Gln Thr Leu Thr Gln Lys Tyr Ser Asn Ala Asn Ser Leu Tyr Asp
305 310 315 320

Asn Leu Val Lys Val Leu Ser Ser Thr Ile Ser Ser Ser Leu Glu Thr
325 330 335

Ala Lys Ser Phe Leu Gln Gly
340

<210> SEQ ID NO 53
<211> LENGTH: 981
<212> TYPE: DNA
<213> ORGANISM: Yersinia pestis

<400> SEQUENCE: 53
atgattagag cctacgaaca aaacccacaa cattttattg aggatctaga aaaagttagg 60
gtggaacaac ttactggtca tggttcttca gttttagaag aattggttca gttagtcaaa 120
gataaaaata tagatatttc cattaaatat gatcccagaa aagattcgga ggtttttgcc 180
aatagagtaa ttactgatga tatcgaattg ctcaagaaaa tcctagctta ttttctaccc 240
gaggatgcca ttcttaaagg cggtcattat gacaaccaac tgcaaaatgg catcaagcga 300
gtaaaagagt tccttgaatc atcgccgaat acacaatggg aattgcgggc gttcatggca 360
gtaatgcatt tctctttaac cgccgatcgt atcgatgatg atattttgaa agtgattgtt 420
gattcaatga atcatcatgg tgatgcccgt agcaagttgc gtgaagaatt agctgagctt 480
accgccgaat taaagattta ttcagttatt caagccgaaa ttaataagca tctgtctagt 540
agtggcacca taaatatcca tgataaatcc attaatctca tggataaaaa tttatatggt 600
tatacagatg aagagatttt taaagccagc gcagagtaca aaattctcga gaaaatgcct 660
caaaccacca ttcaggtgga tgggagcgag aaaaaaatag tctcgataaa ggactttctt 720
ggaagtgaga ataaaagaac cggggcgttg ggtaatctga aaaactcata ctcttataat 780
aaagataata atgaattatc tcactttgcc accacctgct cggataagtc caggccgctc 840
aacgacttgg ttagccaaaa aacaactcag ctgtctgata ttacatcacg ttttaattca 900
gctattgaag cactgaaccg tttcattcag aaatatgatt cagtgatgca acgtctgcta 960
gatgacacgt ctggtaaatg a 981

<210> SEQ ID NO 54
<211> LENGTH: 326
<212> TYPE: PRT
<213> ORGANISM: Yersinia pestis

<400> SEQUENCE: 54

Met Ile Arg Ala Tyr Glu Gln Asn Pro Gln His Phe Ile Glu Asp Leu
1 5 10 15

Glu Lys Val Arg Val Glu Gln Leu Thr Gly His Gly Ser Ser Val Leu
20 25 30

Glu Glu Leu Val Gln Leu Val Lys Asp Lys Asn Ile Asp Ile Ser Ile
35 40 45

Lys Tyr Asp Pro Arg Lys Asp Ser Glu Val Phe Ala Asn Arg Val Ile
50 55 60

Thr Asp Asp Ile Glu Leu Leu Lys Lys Ile Leu Ala Tyr Phe Leu Pro
65 70 75 80

Glu Asp Ala Ile Leu Lys Gly Gly His Tyr Asp Asn Gln Leu Gln Asn
85 90 95

Gly Ile Lys Arg Val Lys Glu Phe Leu Glu Ser Ser Pro Asn Thr Gln
100 105 110

Trp Glu Leu Arg Ala Phe Met Ala Val Met His Phe Ser Leu Thr Ala
115 120 125

Asp Arg Ile Asp Asp Asp Ile Leu Lys Val Ile Val Asp Ser Met Asn
130 135 140

His His Gly Asp Ala Arg Ser Lys Leu Arg Glu Glu Leu Ala Glu Leu
145 150 155 160

```
Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325


<210> SEQ ID NO 55
<211> LENGTH: 579
<212> TYPE: DNA
<213> ORGANISM: Escherichia coli

<400> SEQUENCE: 55

atggatacat caaatgcaac atccgttgtt aatgtgagtg cgagttcttc gacatcgacg      60

atctatgact taggtaatat gtcgaaggat gaggtggtta agctatttga ggaactcggt     120

gtttttcagg ctgcgattct catgttttct tatatgtatc aggcacaaag taatctgtcg     180

attgcaaagt ttgctgatat gaatgaggca tctaaagcgt caaccacggc acaaaagatg     240

gctaatcttg tggatgccaa aattgctgat gttcagagta gcactgataa gaatgcgaaa     300

gccaaacttc ctcaagacgt gattgactat ataaacgatc cacgtaatga cataagtgta     360

actggtattc gtgatcttag tggtgattta agcgctggtg atctgcaaac agtgaaggcg     420

gctatttcag ctaaagcgaa taacctgaca acggtagtga ataatagcca gctcgaaatt     480

cagcaaatgt cgaatacatt aaatctctta acgagtgcac gttctgatgt gcaatctcta     540

caatatagaa ctatttcagc aatatccctt ggtaaataa                            579


<210> SEQ ID NO 56
<211> LENGTH: 192
<212> TYPE: PRT
<213> ORGANISM: Escherichia coli

<400> SEQUENCE: 56

Met Asp Thr Ser Asn Ala Thr Ser Val Val Asn Val Ser Ala Ser Ser
1               5                   10                  15

Ser Thr Ser Thr Ile Tyr Asp Leu Gly Asn Met Ser Lys Asp Glu Val
            20                  25                  30

Val Lys Leu Phe Glu Glu Leu Gly Val Phe Gln Ala Ala Ile Leu Met
        35                  40                  45

Phe Ser Tyr Met Tyr Gln Ala Gln Ser Asn Leu Ser Ile Ala Lys Phe
```

50 55 60

Ala Asp Met Asn Glu Ala Ser Lys Ala Ser Thr Thr Ala Gln Lys Met
65 70 75 80

Ala Asn Leu Val Asp Ala Lys Ile Ala Asp Val Gln Ser Ser Thr Asp
85 90 95

Lys Asn Ala Lys Ala Lys Leu Pro Gln Asp Val Ile Asp Tyr Ile Asn
100 105 110

Asp Pro Arg Asn Asp Ile Ser Val Thr Gly Ile Arg Asp Leu Ser Gly
115 120 125

Asp Leu Ser Ala Gly Asp Leu Gln Thr Val Lys Ala Ala Ile Ser Ala
130 135 140

Lys Ala Asn Asn Leu Thr Thr Val Val Asn Asn Ser Gln Leu Glu Ile
145 150 155 160

Gln Gln Met Ser Asn Thr Leu Asn Leu Leu Thr Ser Ala Arg Ser Asp
165 170 175

Val Gln Ser Leu Gln Tyr Arg Thr Ile Ser Ala Ile Ser Leu Gly Lys
180 185 190

<210> SEQ ID NO 57
<211> LENGTH: 879
<212> TYPE: DNA
<213> ORGANISM: Shigella flexneri

<400> SEQUENCE: 57
atggcattag ataatataaa cctaaatttt agtagtgaca aacagataga aaaatgtgag 60
aaactatctt caatagataa tattgatagt ctcgttttga agaagaagag gaaggttgaa 120
attcctgagt actctttaat tgcatctaac tattttacta ttgataagca ctttgaacat 180
aagcatgata aaggagaaat ttatagtggc attaaaaatg cgttcgaact tagaaacgaa 240
cgagcgacat attctgatat tccagaatca atggccatta aagaaaatat tttgatacca 300
gatcaagata tcaaagcaag ggaaaaaata aatatcggcg atatgagggg gatcttttca 360
tataataaga gtggaaatgc agacaagaac ttcgaaagaa gtcatacttc ttctgtaaac 420
cctgataatc tgctagaatc tgataataga aatggtcaaa ttggtttaaa aaatcatagc 480
ttgtctattg ataagaatat tgctgacatc atttctttac taaatggaag tgttgctaaa 540
tcatttgagc tgcctgtaat gaataaaaat actgcagaca taacccccatc catgtcattg 600 caagaaaaat caatagttga aaatgataaa aatgtttttc aaaaaaatag tgaaatgact 660
taccacttta aacagtgggg ggctggacat tctgttagta tttcagtgga gtctggttct 720
tttgttctaa aaccgtcaga tcaatttgta ggaaataaac ttgacttaat tttgaaacaa 780
gatgctgagg gtaattacag atttgatagc agtcaacata ataaggggaa taaaaataat 840
agtacaggat ataatgaaca gagtgaagaa gaatgctaa 879

<210> SEQ ID NO 58
<211> LENGTH: 292
<212> TYPE: PRT
<213> ORGANISM: Shigella flexneri

<400> SEQUENCE: 58

Met Ala Leu Asp Asn Ile Asn Leu Asn Phe Ser Ser Asp Lys Gln Ile
1 5 10 15

Glu Lys Cys Glu Lys Leu Ser Ser Ile Asp Asn Ile Asp Ser Leu Val
20 25 30

Leu Lys Lys Lys Arg Lys Val Glu Ile Pro Glu Tyr Ser Leu Ile Ala

```
        35                  40                  45

Ser Asn Tyr Phe Thr Ile Asp Lys His Phe Glu His Lys His Asp Lys
    50                  55                  60

Gly Glu Ile Tyr Ser Gly Ile Lys Asn Ala Phe Glu Leu Arg Asn Glu
65                  70                  75                  80

Arg Ala Thr Tyr Ser Asp Ile Pro Glu Ser Met Ala Ile Lys Glu Asn
                85                  90                  95

Ile Leu Ile Pro Asp Gln Asp Ile Lys Ala Arg Glu Lys Ile Asn Ile
            100                 105                 110

Gly Asp Met Arg Gly Ile Phe Ser Tyr Asn Lys Ser Gly Asn Ala Asp
        115                 120                 125

Lys Asn Phe Glu Arg Ser His Thr Ser Ser Val Asn Pro Asp Asn Leu
    130                 135                 140

Leu Glu Ser Asp Asn Arg Asn Gly Gln Ile Gly Leu Lys Asn His Ser
145                 150                 155                 160

Leu Ser Ile Asp Lys Asn Ile Ala Asp Ile Ile Ser Leu Leu Asn Gly
                165                 170                 175

Ser Val Ala Lys Ser Phe Glu Leu Pro Val Met Asn Lys Asn Thr Ala
            180                 185                 190

Asp Ile Thr Pro Ser Met Ser Leu Gln Glu Lys Ser Ile Val Glu Asn
        195                 200                 205

Asp Lys Asn Val Phe Gln Lys Asn Ser Glu Met Thr Tyr His Phe Lys
    210                 215                 220

Gln Trp Gly Ala Gly His Ser Val Ser Ile Ser Val Glu Ser Gly Ser
225                 230                 235                 240

Phe Val Leu Lys Pro Ser Asp Gln Phe Val Gly Asn Lys Leu Asp Leu
                245                 250                 255

Ile Leu Lys Gln Asp Ala Glu Gly Asn Tyr Arg Phe Asp Ser Ser Gln
            260                 265                 270

His Asn Lys Gly Asn Lys Asn Asn Ser Thr Gly Tyr Asn Glu Gln Ser
        275                 280                 285

Glu Glu Glu Cys
    290


<210> SEQ ID NO 59
<211> LENGTH: 1011
<212> TYPE: DNA
<213> ORGANISM: Salmonella enterica

<400> SEQUENCE: 59

atgggcgatg tgtcagctgt cagttcatcc gggaacattt tactgccgca gcaggatgag      60

gttggcggtt tatcagaagc attaaaaaaa gcggtggaaa aacataagac agaatattcc     120

ggtgataaaa aagatcgcga ctatggcgat gctttcgtaa tgcataaaga aacggcttta     180

ccgttattac tggcggcatg gcgacatggc gcgccagcga aatcagaaca tcacaatggc     240

aacgtttctg gtctgcatca taacggaaaa agcgaactca ggattgctga aaaactgttg     300

aaagtcactg ctgaaaaatc tgtcggtttg atctctgcgg aggccaaagt agataaatcc     360

gcagcgttgc tatcgtctaa aaataggccg ttagaaagcg taagcggtaa aaaattatct     420

gctgatttaa aagctgtgga atccgttagt gaagtaaccg ataacgccac gggaatctct     480

gacgataata tcaaggcatt gcctggggat aataaagcca tcgcgggcga aggcgttcgt     540

aaagagggcg cgccgctggc gcgggatgtc gcacctgccc gaatggccgc agccaatacc     600

ggtaagcctg aagataaaga tcataaaaag gttaaagatg tttctcagct tccgctgcaa     660
```

```
ccaaccacta tcgccgatct tagccaatta accggcggcg atgaaaaaat gcctttagcg    720

gcgcaatcaa agccgatgat gactattttt cccactgccg atggcgtgaa aggagaggat    780

agctcgctga cttaccgttt tcagcgctgg ggaaatgact attccgtcaa tattcaggcg    840

cggcaagcag gggagttttc gttaataccg tcaaatacgc aggttgaaca tcgtttgcat    900

gatcaatggc aaaacggtaa tccccagcgc tggcacctga cgcgagacga tcaacaaaat    960

ccgcagcagc aacagcacag acagcaatct ggcgaggagg atgacgcctg a            1011
```

<210> SEQ ID NO 60
<211> LENGTH: 336
<212> TYPE: PRT
<213> ORGANISM: Salmonella enterica

<400> SEQUENCE: 60

```
Met Gly Asp Val Ser Ala Val Ser Ser Ser Gly Asn Ile Leu Leu Pro
1               5                   10                  15

Gln Gln Asp Glu Val Gly Gly Leu Ser Glu Ala Leu Lys Lys Ala Val
            20                  25                  30

Glu Lys His Lys Thr Glu Tyr Ser Gly Asp Lys Lys Asp Arg Asp Tyr
        35                  40                  45

Gly Asp Ala Phe Val Met His Lys Glu Thr Ala Leu Pro Leu Leu Leu
    50                  55                  60

Ala Ala Trp Arg His Gly Ala Pro Ala Lys Ser Glu His His Asn Gly
65                  70                  75                  80

Asn Val Ser Gly Leu His His Asn Gly Lys Ser Glu Leu Arg Ile Ala
                85                  90                  95

Glu Lys Leu Leu Lys Val Thr Ala Glu Lys Ser Val Gly Leu Ile Ser
            100                 105                 110

Ala Glu Ala Lys Val Asp Lys Ser Ala Ala Leu Leu Ser Ser Lys Asn
        115                 120                 125

Arg Pro Leu Glu Ser Val Ser Gly Lys Lys Leu Ser Ala Asp Leu Lys
    130                 135                 140

Ala Val Glu Ser Val Ser Glu Val Thr Asp Asn Ala Thr Gly Ile Ser
145                 150                 155                 160

Asp Asp Asn Ile Lys Ala Leu Pro Gly Asp Asn Lys Ala Ile Ala Gly
                165                 170                 175

Glu Gly Val Arg Lys Glu Gly Ala Pro Leu Ala Arg Asp Val Ala Pro
            180                 185                 190

Ala Arg Met Ala Ala Ala Asn Thr Gly Lys Pro Glu Asp Lys Asp His
        195                 200                 205

Lys Lys Val Lys Asp Val Ser Gln Leu Pro Leu Gln Pro Thr Thr Ile
    210                 215                 220

Ala Asp Leu Ser Gln Leu Thr Gly Gly Asp Glu Lys Met Pro Leu Ala
225                 230                 235                 240

Ala Gln Ser Lys Pro Met Met Thr Ile Phe Pro Thr Ala Asp Gly Val
                245                 250                 255

Lys Gly Glu Asp Ser Ser Leu Thr Tyr Arg Phe Gln Arg Trp Gly Asn
            260                 265                 270

Asp Tyr Ser Val Asn Ile Gln Ala Arg Gln Ala Gly Glu Phe Ser Leu
        275                 280                 285

Ile Pro Ser Asn Thr Gln Val Glu His Arg Leu His Asp Gln Trp Gln
    290                 295                 300

Asn Gly Asn Pro Gln Arg Trp His Leu Thr Arg Asp Asp Gln Gln Asn
```

305 310 315 320

Pro Gln Gln Gln Gln His Arg Gln Gln Ser Gly Glu Glu Asp Asp Ala
325 330 335

<210> SEQ ID NO 61
<211> LENGTH: 1368
<212> TYPE: DNA
<213> ORGANISM: Yersinia pestis

<400> SEQUENCE: 61
atgaataaaa tcaccactcg ttccccatta gaacctgagt atcaacctct ggggaagccg 60
catcatgctt tgcaagcatg tgtcgatttt gagcaagcgc tgttgcataa taataagggg 120
aattgtcatc ccaaagaaga gtcgcttaaa cctgtacgtc cgcatgacct tggcaaaaaa 180
gaaggtcaga aaggagatgg cttgcgtgcg catgcgccat tagcggcgac gtctcaaccc 240
ggaaggaaag aggtaggatt aaaacctcaa cacaaccatc agaataatca tgatttcaac 300
ttatctccgc ttgccgaagg tgctaccaat agagcgcact tataccagca ggatagccgt 360
tttgatgacc gcgtagagag tattattaat gctctcatgc cattggcgcc ctttttagag 420
ggggtgactt gtgaaacggg gacatcaagt gaatccccct gcgagccgtc tggacatgat 480
gagttatttg ttcagcaatc gcctatcgat tccgctcaac cagttcaatt gaatagcaag 540
ccgactgttc agccattgaa tccggctgct gacggcgcag aggttattgt atggtctgtc 600
ggtagggaaa ctccggccag tatagcaaaa aaccagcgcg atagcaggca aaaacgcctt 660
gcagaagaac cgttagctct tcatcaaaaa gcattgccag agatatgtcc cccggcagtt 720
agtgccacac cggatgatca tttggtagca agatggtgtg ctactcctgt gactgaggta 780
gcagaaaaat ctgctcgttt tccgtacaaa gcgacagtgc agtcagagca actggacatg 840
accgagctgg cggatcggtc ccaacatctt actgatggcg ttgatagcag caaagatacc 900
atcgaaccac cgcgaccaga aaaactgtta cttccgcgcg aagaaacctt gccggagatg 960
tattccttgt cttttacagc accggttgtc acgccgggtg atcacctatt agcaacaatg 1020
cgcgcgacca ggctggcatc agtctcagag caacttatac agttagcaca gcgactagcg 1080
gtagaactag aactgcgcgg cggctcatcc caagtaaccc aattacacct taacttacct 1140
gaattggggg ctattatggt tcgtattgct gagattccgg gaaaactgca tgtagaactg 1200
atcgccagtc gggaagcttt aagaatttta gcgcagggaa gttatgatct tcttgagcga 1260
ttacaacgca ttgagccaac acaacttgat tttcaagcta gcgatgacag tgaacaggag 1320
tcacgtcaga aacgccacgt ctatgaggag tgggaggctg aagaatga 1368

<210> SEQ ID NO 62
<211> LENGTH: 455
<212> TYPE: PRT
<213> ORGANISM: Yersinia pestis

<400> SEQUENCE: 62

Met Asn Lys Ile Thr Thr Arg Ser Pro Leu Glu Pro Glu Tyr Gln Pro
1 5 10 15

Leu Gly Lys Pro His His Ala Leu Gln Ala Cys Val Asp Phe Glu Gln
20 25 30

Ala Leu Leu His Asn Asn Lys Gly Asn Cys His Pro Lys Glu Glu Ser
35 40 45

Leu Lys Pro Val Arg Pro His Asp Leu Gly Lys Lys Glu Gly Gln Lys
50 55 60

```
Gly Asp Gly Leu Arg Ala His Ala Pro Leu Ala Ala Thr Ser Gln Pro
65                  70                  75                  80

Gly Arg Lys Glu Val Gly Leu Lys Pro Gln His Asn His Gln Asn Asn
                85                  90                  95

His Asp Phe Asn Leu Ser Pro Leu Ala Glu Gly Ala Thr Asn Arg Ala
            100                 105                 110

His Leu Tyr Gln Gln Asp Ser Arg Phe Asp Asp Arg Val Glu Ser Ile
        115                 120                 125

Ile Asn Ala Leu Met Pro Leu Ala Pro Phe Leu Glu Gly Val Thr Cys
    130                 135                 140

Glu Thr Gly Thr Ser Ser Glu Ser Pro Cys Glu Pro Ser Gly His Asp
145                 150                 155                 160

Glu Leu Phe Val Gln Gln Ser Pro Ile Asp Ser Ala Gln Pro Val Gln
                165                 170                 175

Leu Asn Ser Lys Pro Thr Val Gln Pro Leu Asn Pro Ala Ala Asp Gly
            180                 185                 190

Ala Glu Val Ile Val Trp Ser Val Gly Arg Glu Thr Pro Ala Ser Ile
        195                 200                 205

Ala Lys Asn Gln Arg Asp Ser Arg Gln Lys Arg Leu Ala Glu Glu Pro
    210                 215                 220

Leu Ala Leu His Gln Lys Ala Leu Pro Glu Ile Cys Pro Pro Ala Val
225                 230                 235                 240

Ser Ala Thr Pro Asp Asp His Leu Val Ala Arg Trp Cys Ala Thr Pro
                245                 250                 255

Val Thr Glu Val Ala Glu Lys Ser Ala Arg Phe Pro Tyr Lys Ala Thr
            260                 265                 270

Val Gln Ser Glu Gln Leu Asp Met Thr Glu Leu Ala Asp Arg Ser Gln
        275                 280                 285

His Leu Thr Asp Gly Val Asp Ser Ser Lys Asp Thr Ile Glu Pro Pro
    290                 295                 300

Arg Pro Glu Lys Leu Leu Leu Pro Arg Glu Glu Thr Leu Pro Glu Met
305                 310                 315                 320

Tyr Ser Leu Ser Phe Thr Ala Pro Val Val Thr Pro Gly Asp His Leu
                325                 330                 335

Leu Ala Thr Met Arg Ala Thr Arg Leu Ala Ser Val Ser Glu Gln Leu
            340                 345                 350

Ile Gln Leu Ala Gln Arg Leu Ala Val Glu Leu Glu Leu Arg Gly Gly
        355                 360                 365

Ser Ser Gln Val Thr Gln Leu His Leu Asn Leu Pro Glu Leu Gly Ala
    370                 375                 380

Ile Met Val Arg Ile Ala Glu Ile Pro Gly Lys Leu His Val Glu Leu
385                 390                 395                 400

Ile Ala Ser Arg Glu Ala Leu Arg Ile Leu Ala Gln Gly Ser Tyr Asp
                405                 410                 415

Leu Leu Glu Arg Leu Gln Arg Ile Glu Pro Thr Gln Leu Asp Phe Gln
            420                 425                 430

Ala Ser Asp Asp Ser Glu Gln Glu Ser Arg Gln Lys Arg His Val Tyr
        435                 440                 445

Glu Glu Trp Glu Ala Glu Glu
    450                 455
```

<210> SEQ ID NO 63
<211> LENGTH: 417
<212> TYPE: DNA

<213> ORGANISM: Escherichia coli

<400> SEQUENCE: 63

```
ttgactagag tttctctaaa aagaaatttg atagagcctg tttcttttcg gccatcagat     60
gattggccgc aaggagaaga aagttttaat gatattttt atcatataaa aaaaagatcg    120
cctgatacgt tgttcatacg aatggcttct ttatggaaga gattgtttta ctcctcgggc    180
cgaagacgac gctactttga agaaggggag cactcgttta gtattctttg tggaagatta    240
cgaggaattg ttttaacaat taaatgtagt aacggaatca tttatctgtc tattaaagta    300
agcccaaata atagaaatca tgttttttta tatcataaaa aagactatgt tttcgataag    360
ttaaaagaaa tctttcctga tgaagccatt gagttcacaa ttgaatatga aaattaa       417
```

<210> SEQ ID NO 64
<211> LENGTH: 138
<212> TYPE: PRT
<213> ORGANISM: Escherichia coli

<400> SEQUENCE: 64

```
Met Thr Arg Val Ser Leu Lys Arg Asn Leu Ile Glu Pro Val Ser Phe
1               5                   10                  15

Arg Pro Ser Asp Asp Trp Pro Gln Gly Glu Glu Ser Phe Asn Asp Ile
            20                  25                  30

Phe Tyr His Ile Lys Lys Arg Ser Pro Asp Thr Leu Phe Ile Arg Met
        35                  40                  45

Ala Ser Leu Trp Lys Arg Leu Phe Tyr Ser Ser Gly Arg Arg Arg Arg
    50                  55                  60

Tyr Phe Glu Glu Gly Glu His Ser Phe Ser Ile Leu Cys Gly Arg Leu
65                  70                  75                  80

Arg Gly Ile Val Leu Thr Ile Lys Cys Ser Asn Gly Ile Ile Tyr Leu
                85                  90                  95

Ser Ile Lys Val Ser Pro Asn Asn Arg Asn His Val Phe Leu Tyr His
            100                 105                 110

Lys Lys Asp Tyr Val Phe Asp Lys Leu Lys Glu Ile Phe Pro Asp Glu
        115                 120                 125

Ala Ile Glu Phe Thr Ile Glu Tyr Glu Asn
    130                 135
```

<210> SEQ ID NO 65
<211> LENGTH: 1293
<212> TYPE: DNA
<213> ORGANISM: Shigella flexneri

<400> SEQUENCE: 65

```
atgagctata caaaattgct cactcaatta tcttttccta atagaatctc ggggccaatc     60
ttggaaacaa gtcttagcga tgtttcgatt ggtgagattt gtaacattca ggctggaatt    120
gaaagtaatg aaattgttgc aagagctcag gttgtaggat ttcatgatga aaaaacaata    180
ttaagcttga ttggaaattc tcgtggactt tcacggcaaa cattgattaa gcccactgcc    240
cagtttcttc atacgcaagt cggccgtgga ttattgggag cagtagtcaa tcctttaggg    300
gaggttactg ataagtttgc tgttacggat aacagtgaaa ttctttatcg acctgtagat    360
aatgctcctc cgctatatag tgaaagggct gcaattgaga agccttttt aacaggtatt     420
aaggttattg attctttact cacgtgtggt gaaggacagc gaatggggat ttttgcgtca    480
gctggttgtg gcaaaacttt tctcatgaat atgctcattg aacatagtgg tgctgatata    540
```

-continued

```
tatgttattg ggttaattgg tgagcgaggt cgagaggtta ctgaaacggt tgattatttg    600

aaaaactctg agaaaaaaag caggtgtgtt ttagtatatg caacttcgga ttactcttcg    660

gttgatcgtt gtaatgctgc atatatagcc actgctatag ccgaattttt taggactgaa    720

ggacataaag tagcgctttt tattgattca ttaacaaggt atgccagagc attacgtgat    780

gtggccttag ccgctggaga atcacctgcc agaagaggct atccggtttc ggtttttgat    840

agcttaccca gacttcttga aaggccagga aagttaaagg caggtggctc tattactgca    900

ttttacactg ttcttttgga ggatgatgat tttgctgatc cattagctga agaggtaaga    960

tccattttag atggacatat atatttgagc agaaatctag cccaaaaagg acaatttcct   1020

gcaattgatt ccttaaaaag tataagcagg gtatttacac aggttgttga tgaaaaacat   1080

cgtattatgg ccgctgcatt tcgggagcta ctttctgaaa tagaagagct aaggacaatt   1140

attgactttg gtgaatacaa accgggggag aatgcctctc aggataaaat ctacaacaaa   1200

atatctgttg ttgagagttt tctgaagcaa gattatcgac tcggttttac ttatgagcag   1260

acaatggagc ttattggtga aacaattaga taa                               1293


<210> SEQ ID NO 66
<211> LENGTH: 430
<212> TYPE: PRT
<213> ORGANISM: Shigella flexneri

<400> SEQUENCE: 66

Met Ser Tyr Thr Lys Leu Leu Thr Gln Leu Ser Phe Pro Asn Arg Ile
1               5                   10                  15

Ser Gly Pro Ile Leu Glu Thr Ser Leu Ser Asp Val Ser Ile Gly Glu
            20                  25                  30

Ile Cys Asn Ile Gln Ala Gly Ile Glu Ser Asn Glu Ile Val Ala Arg
        35                  40                  45

Ala Gln Val Val Gly Phe His Asp Glu Lys Thr Ile Leu Ser Leu Ile
    50                  55                  60

Gly Asn Ser Arg Gly Leu Ser Arg Gln Thr Leu Ile Lys Pro Thr Ala
65                  70                  75                  80

Gln Phe Leu His Thr Gln Val Gly Arg Gly Leu Leu Gly Ala Val Val
                85                  90                  95

Asn Pro Leu Gly Glu Val Thr Asp Lys Phe Ala Val Thr Asp Asn Ser
            100                 105                 110

Glu Ile Leu Tyr Arg Pro Val Asp Asn Ala Pro Pro Leu Tyr Ser Glu
        115                 120                 125

Arg Ala Ala Ile Glu Lys Pro Phe Leu Thr Gly Ile Lys Val Ile Asp
    130                 135                 140

Ser Leu Leu Thr Cys Gly Glu Gly Gln Arg Met Gly Ile Phe Ala Ser
145                 150                 155                 160

Ala Gly Cys Gly Lys Thr Phe Leu Met Asn Met Leu Ile Glu His Ser
                165                 170                 175

Gly Ala Asp Ile Tyr Val Ile Gly Leu Ile Gly Glu Arg Gly Arg Glu
            180                 185                 190

Val Thr Glu Thr Val Asp Tyr Leu Lys Asn Ser Glu Lys Lys Ser Arg
        195                 200                 205

Cys Val Leu Val Tyr Ala Thr Ser Asp Tyr Ser Ser Val Asp Arg Cys
    210                 215                 220

Asn Ala Ala Tyr Ile Ala Thr Ala Ile Ala Glu Phe Phe Arg Thr Glu
225                 230                 235                 240
```

```
Gly His Lys Val Ala Leu Phe Ile Asp Ser Leu Thr Arg Tyr Ala Arg
                245                 250                 255

Ala Leu Arg Asp Val Ala Leu Ala Ala Gly Glu Ser Pro Ala Arg Arg
            260                 265                 270

Gly Tyr Pro Val Ser Val Phe Asp Ser Leu Pro Arg Leu Leu Glu Arg
        275                 280                 285

Pro Gly Lys Leu Lys Ala Gly Gly Ser Ile Thr Ala Phe Tyr Thr Val
    290                 295                 300

Leu Leu Glu Asp Asp Asp Phe Ala Asp Pro Leu Ala Glu Glu Val Arg
305                 310                 315                 320

Ser Ile Leu Asp Gly His Ile Tyr Leu Ser Arg Asn Leu Ala Gln Lys
                325                 330                 335

Gly Gln Phe Pro Ala Ile Asp Ser Leu Lys Ser Ile Ser Arg Val Phe
            340                 345                 350

Thr Gln Val Val Asp Glu Lys His Arg Ile Met Ala Ala Ala Phe Arg
        355                 360                 365

Glu Leu Leu Ser Glu Ile Glu Glu Leu Arg Thr Ile Ile Asp Phe Gly
    370                 375                 380

Glu Tyr Lys Pro Gly Glu Asn Ala Ser Gln Asp Lys Ile Tyr Asn Lys
385                 390                 395                 400

Ile Ser Val Val Glu Ser Phe Leu Lys Gln Asp Tyr Arg Leu Gly Phe
                405                 410                 415

Thr Tyr Glu Gln Thr Met Glu Leu Ile Gly Glu Thr Ile Arg
            420                 425                 430
```

<210> SEQ ID NO 67
<211> LENGTH: 1296
<212> TYPE: DNA
<213> ORGANISM: Salmonella enterica

<400> SEQUENCE: 67

```
atgaaaacac ctcgtttact gcaatatctg gcctacccac aaaaaataac cggcccaatt     60

attgaggcgg aattgcgcga tgtggccatt ggcgaactgt gtgaaatacg ccgtggctgg    120

caccaaaaac aggttgttgc acgtgcgcag gtggttggct tacagcggga acgcaccgtg    180

ctgagcctta tcggcaatgc ccaggggctg agccgcgatg tcgtgcttta tcccactgga    240

cgtgcgttat cggcgtgggt gggatactcg gtattaggcg cggtgttgga tccgacaggg    300

aaaatcgttg agcgttttac ccctgaagtg gcgccgatta gcgaagaacg cgttattgat    360

gtcgcaccgc cgtcttacgc ttcacgcgtt ggcgtccgtg aaccgctgat taccggtgtg    420

cgcgcgattg acgggttatt gacctgtggc gtaggccagc gaatgggcat ttttgcctcc    480

gcaggatgcg gtaagaccat gctgatgcat atgctgatcg agcaaacgga ggcggatgtc    540

tttgttatcg gtcttatcgg tgaacgaggc cgtgaggtca ctgaattcgt ggatatgttg    600

cgcgcttcgc ataagaaaga aaaatgcgtg ctggtttttg ccacttccga tttcccctcg    660

gtcgatcgct gcaatgcggc gcaactggcg acaaccgtag cggaatattt tcgcgaccag    720

ggaaaacggg tcgtgctttt tatcgattcc atgacccgtt atgcgcgtgc tttgcgagac    780

gtggcactgg cgtcgggaga gcgtccggct cgtcgaggtt atcccgcctc cgtattcgat    840

aatttgcccc gcttgctgga acgcccaggg gcgaccagcg agggaagcat tactgccttt    900

tatacggtac tgctggaaag cgaggaagag gcggacccga tggcggatga aattcgctct    960

atccttgacg gtcacctgta tctgagcaga aagctggccg ggcagggaca ttacccggca   1020

atcgatgtac tgaaaagcgt aagccgcgtt tttggacaag tcacgacgcc gacacatgct   1080
```

```
gaacaggcat ctgccgtgcg taaattaatg acgcgtttgg aagagctcca gcttttcatt   1140

gacttgggag aatatcgtcc tggcgaaaat atcgataacg atcgggcgat gcagatgcgg   1200

gatagcctga aagcctggtt atgccagccg gtagcgcagt attcatcctt tgatgacacg   1260

ttgagcggta tgaatgcatt cgctgaccag aattaa                              1296
```

<210> SEQ ID NO 68
<211> LENGTH: 431
<212> TYPE: PRT
<213> ORGANISM: Salmonella enterica

<400> SEQUENCE: 68

```
Met Lys Thr Pro Arg Leu Leu Gln Tyr Leu Ala Tyr Pro Gln Lys Ile
1               5                   10                  15

Thr Gly Pro Ile Ile Glu Ala Glu Leu Arg Asp Val Ala Ile Gly Glu
            20                  25                  30

Leu Cys Glu Ile Arg Arg Gly Trp His Gln Lys Gln Val Val Ala Arg
        35                  40                  45

Ala Gln Val Val Gly Leu Gln Arg Glu Arg Thr Val Leu Ser Leu Ile
    50                  55                  60

Gly Asn Ala Gln Gly Leu Ser Arg Asp Val Val Leu Tyr Pro Thr Gly
65                  70                  75                  80

Arg Ala Leu Ser Ala Trp Val Gly Tyr Ser Val Leu Gly Ala Val Leu
                85                  90                  95

Asp Pro Thr Gly Lys Ile Val Glu Arg Phe Thr Pro Glu Val Ala Pro
            100                 105                 110

Ile Ser Glu Glu Arg Val Ile Asp Val Ala Pro Pro Ser Tyr Ala Ser
        115                 120                 125

Arg Val Gly Val Arg Glu Pro Leu Ile Thr Gly Val Arg Ala Ile Asp
    130                 135                 140

Gly Leu Leu Thr Cys Gly Val Gly Gln Arg Met Gly Ile Phe Ala Ser
145                 150                 155                 160

Ala Gly Cys Gly Lys Thr Met Leu Met His Met Leu Ile Glu Gln Thr
                165                 170                 175

Glu Ala Asp Val Phe Val Ile Gly Leu Ile Gly Glu Arg Gly Arg Glu
            180                 185                 190

Val Thr Glu Phe Val Asp Met Leu Arg Ala Ser His Lys Lys Glu Lys
        195                 200                 205

Cys Val Leu Val Phe Ala Thr Ser Asp Phe Pro Ser Val Asp Arg Cys
    210                 215                 220

Asn Ala Ala Gln Leu Ala Thr Thr Val Ala Glu Tyr Phe Arg Asp Gln
225                 230                 235                 240

Gly Lys Arg Val Val Leu Phe Ile Asp Ser Met Thr Arg Tyr Ala Arg
                245                 250                 255

Ala Leu Arg Asp Val Ala Leu Ala Ser Gly Glu Arg Pro Ala Arg Arg
            260                 265                 270

Gly Tyr Pro Ala Ser Val Phe Asp Asn Leu Pro Arg Leu Leu Glu Arg
        275                 280                 285

Pro Gly Ala Thr Ser Glu Gly Ser Ile Thr Ala Phe Tyr Thr Val Leu
    290                 295                 300

Leu Glu Ser Glu Glu Glu Ala Asp Pro Met Ala Asp Glu Ile Arg Ser
305                 310                 315                 320

Ile Leu Asp Gly His Leu Tyr Leu Ser Arg Lys Leu Ala Gly Gln Gly
                325                 330                 335
```

His Tyr Pro Ala Ile Asp Val Leu Lys Ser Val Ser Arg Val Phe Gly
340 345 350

Gln Val Thr Thr Pro Thr His Ala Glu Gln Ala Ser Ala Val Arg Lys
355 360 365

Leu Met Thr Arg Leu Glu Glu Leu Gln Leu Phe Ile Asp Leu Gly Glu
370 375 380

Tyr Arg Pro Gly Glu Asn Ile Asp Asn Asp Arg Ala Met Gln Met Arg
385 390 395 400

Asp Ser Leu Lys Ala Trp Leu Cys Gln Pro Val Ala Gln Tyr Ser Ser
405 410 415

Phe Asp Asp Thr Leu Ser Gly Met Asn Ala Phe Ala Asp Gln Asn
420 425 430

<210> SEQ ID NO 69
<211> LENGTH: 1233
<212> TYPE: DNA
<213> ORGANISM: Yersinia pestis

<400> SEQUENCE: 69
gtgacaggaa cgttattaaa agcggtagtg ccaggtgtgc gcatcggtga gttatgttac 60
ttacgtaacc ctgacaacag cctgtcttta caggctgaag tcataggttt tgcccaacat 120
caagcattac ttattccact tggtgaaatg tacgggatat cttctaatac tgaagttagc 180
ccgacaggga caatgcatca ggttggggtg ggtgaacatc tgctgggaca ggtgttggat 240
ggtttagggc agcctttcga tgggggcat ctccctgaac cggcggcttg gtacccagtt 300
tatcaggatg ccccagcgcc gatgagccga aaacttatta ccacaccact ttctttgggg 360
atccgggtta ttgacggttt gcttacctgt ggcgaggggc aaagaatggg catcttcgcg 420
gccgccgggg gggggaaaag tacactgctt gcttcgctta ttcgtagtgc tgaagtagac 480
gtaaccgtgc tggcgcttat tggtgagcgt ggacgcgaag tgcgtgagtt tattgagtct 540
gatttaggcg aagaggggtt acgcaaagcg gttctcgtgg tggccacctc ggatcggccc 600
tcaatggaaa gagccaaagc tggattcgtg gcgacatcta ttgctgaata ttttcgcgat 660
caagggaaac gcgtattgtt acttatggac tctgtaacac ggtttgctcg tgctcagcgt 720
gaaataggct tagctgcggg agaaccaccg actcgccgcg gttatcctcc gtcagtattt 780
gccgctttac cccgtttgat ggaaagggct ggtcagtcca gcaaagggtc aattacggct 840
ctctataccg tactggtcga aggggacgat atgaccgaac ccgtggccga cgaaacacgt 900
tcgatacttg atggtcatat tattctgtca cggaaattag cggcagctaa tcattatcct 960
gccattgacg tattacgttc agcgagcagg gtgatgaatc aaattgtcag caaggagcac 1020
aaaacctggg cgggggactt acgccgttta ttggccaaat atgaagaagt ggaattgctg 1080
ttgcaaatcg gggagtacca gaaagggcaa gacaaagagg ccgatcaagc gattgaacgc 1140
atgggggcga ttcgaggatg gctctgccag gggacgcacg agttaagcca tttcaatgag 1200
acgctgaact tattggagac gctgacccaa tga 1233

<210> SEQ ID NO 70
<211> LENGTH: 410
<212> TYPE: PRT
<213> ORGANISM: Yersinia pestis

<400> SEQUENCE: 70

Met Thr Gly Thr Leu Leu Lys Ala Val Val Pro Gly Val Arg Ile Gly
1 5 10 15

```
Glu Leu Cys Tyr Leu Arg Asn Pro Asp Asn Ser Leu Ser Leu Gln Ala
            20                  25                  30

Glu Val Ile Gly Phe Ala Gln His Gln Ala Leu Leu Ile Pro Leu Gly
        35                  40                  45

Glu Met Tyr Gly Ile Ser Ser Asn Thr Glu Val Ser Pro Thr Gly Thr
    50                  55                  60

Met His Gln Val Gly Val Gly Glu His Leu Leu Gly Gln Val Leu Asp
65                  70                  75                  80

Gly Leu Gly Gln Pro Phe Asp Gly Gly His Leu Pro Glu Pro Ala Ala
                85                  90                  95

Trp Tyr Pro Val Tyr Gln Asp Ala Pro Ala Pro Met Ser Arg Lys Leu
            100                 105                 110

Ile Thr Thr Pro Leu Ser Leu Gly Ile Arg Val Ile Asp Gly Leu Leu
        115                 120                 125

Thr Cys Gly Glu Gly Gln Arg Met Gly Ile Phe Ala Ala Ala Gly Gly
    130                 135                 140

Gly Lys Ser Thr Leu Leu Ala Ser Leu Ile Arg Ser Ala Glu Val Asp
145                 150                 155                 160

Val Thr Val Leu Ala Leu Ile Gly Glu Arg Gly Arg Glu Val Arg Glu
                165                 170                 175

Phe Ile Glu Ser Asp Leu Gly Glu Glu Gly Leu Arg Lys Ala Val Leu
            180                 185                 190

Val Val Ala Thr Ser Asp Arg Pro Ser Met Glu Arg Ala Lys Ala Gly
        195                 200                 205

Phe Val Ala Thr Ser Ile Ala Glu Tyr Phe Arg Asp Gln Gly Lys Arg
    210                 215                 220

Val Leu Leu Leu Met Asp Ser Val Thr Arg Phe Ala Arg Ala Gln Arg
225                 230                 235                 240

Glu Ile Gly Leu Ala Ala Gly Glu Pro Pro Thr Arg Arg Gly Tyr Pro
                245                 250                 255

Pro Ser Val Phe Ala Ala Leu Pro Arg Leu Met Glu Arg Ala Gly Gln
            260                 265                 270

Ser Ser Lys Gly Ser Ile Thr Ala Leu Tyr Thr Val Leu Val Glu Gly
        275                 280                 285

Asp Asp Met Thr Glu Pro Val Ala Asp Glu Thr Arg Ser Ile Leu Asp
    290                 295                 300

Gly His Ile Ile Leu Ser Arg Lys Leu Ala Ala Ala Asn His Tyr Pro
305                 310                 315                 320

Ala Ile Asp Val Leu Arg Ser Ala Ser Arg Val Met Asn Gln Ile Val
                325                 330                 335

Ser Lys Glu His Lys Thr Trp Ala Gly Asp Leu Arg Arg Leu Leu Ala
            340                 345                 350

Lys Tyr Glu Glu Val Glu Leu Leu Leu Gln Ile Gly Glu Tyr Gln Lys
        355                 360                 365

Gly Gln Asp Lys Glu Ala Asp Gln Ala Ile Glu Arg Met Gly Ala Ile
    370                 375                 380

Arg Gly Trp Leu Cys Gln Gly Thr His Glu Leu Ser His Phe Asn Glu
385                 390                 395                 400

Thr Leu Asn Leu Leu Glu Thr Leu Thr Gln
                405                 410
```

<210> SEQ ID NO 71
<211> LENGTH: 1341

<212> TYPE: DNA
<213> ORGANISM: Escherichia coli

<400> SEQUENCE: 71

```
atgatttcag agcatgattc tgtattggaa aaatacccac gtattcagaa agtgctcaat     60
agcactgtgc cggcattatc attaaattcg tctaccagat atgaaggcaa gattatcaat    120
atcggcggga cgattattaa ggcgcgttta ccaaaagcgc gtattggcgc cttttataag    180
atagaaccca gtcaacgttt agccgaggtg atcgctattg atgaagatga ggttttcttg    240
ttgccttttg agcatgtttc cggcatgtac tgtggtcagt ggttaagtta tcagggagat    300
gagttcaaga ttcgtgttgg agacgcacta cttgggcggc ttgttgatgg cataggcaga    360
ccaatggaga gtaatattgc tgccccctat cttccgtttg aacgcagctt gtatgctgaa    420
ccaccagatc ctttattaag gcaggttatt gatcagccat ttatacttgg cgtcagggca    480
attgatgggc tactaacttg cggtattggg cagcgtatcg gtatttttgc tggttcaggc    540
gttggtaaaa gtacgctttt ggggatgatt tgtaatggcg catccgcaga tattattgtc    600
cttgctctta tcggcgaacg tggtcgcgaa gtaaatgaat tcctcgcgct cttacctcaa    660
tccacgcttt ctaaatgtgt actggtcgtc acaacgtcag accgccccgc gctggaaagg    720
atgaaagccg catttacggc gacgactatt gcagagtact tccgcgatca aggtaaaaat    780
gtattattaa tgatggattc tgtaactcgt tatgcccgag ccgcacgtga tgttgggctt    840
gcatcgggag aacctgatgt aaggggggga ttccctccga gtgttttttc ttcgttaccc    900
aaattattag agcgagcggg gcctgcgcca aaaggttcaa taaccgcgat ttatacggtg    960
ttgttagaaa gcgataatgt taatgatcct attggcgatg aagtccgctc tattcttgat   1020
gggcacatcg tacttacccg agaacttgca gaggaaaacc atttccctgc aattgatatt   1080
ggtttaagtg ccagtcgtgt tatgcataac gttgttacat cggagcattt gcgtgcggcg   1140
gcagaatgca aaaagcttat tgcaacttat aaaaatgttg agctgcttat tcgtattggt   1200
gagtacacga tggggcaaga tcctgaagca gataaggcaa taaaaaatag gaaattaatt   1260
cagaacttta tacaacaaag caccaaagat atcagtagtt acgaaaaaac gattgaaagc   1320
ctattcaaag tggttgcctg a                                             1341
```

<210> SEQ ID NO 72
<211> LENGTH: 446
<212> TYPE: PRT
<213> ORGANISM: Escherichia coli

<400> SEQUENCE: 72

```
Met Ile Ser Glu His Asp Ser Val Leu Glu Lys Tyr Pro Arg Ile Gln
1               5                   10                  15

Lys Val Leu Asn Ser Thr Val Pro Ala Leu Ser Leu Asn Ser Ser Thr
            20                  25                  30

Arg Tyr Glu Gly Lys Ile Ile Asn Ile Gly Gly Thr Ile Ile Lys Ala
        35                  40                  45

Arg Leu Pro Lys Ala Arg Ile Gly Ala Phe Tyr Lys Ile Glu Pro Ser
    50                  55                  60

Gln Arg Leu Ala Glu Val Ile Ala Ile Asp Glu Asp Glu Val Phe Leu
65                  70                  75                  80

Leu Pro Phe Glu His Val Ser Gly Met Tyr Cys Gly Gln Trp Leu Ser
                85                  90                  95

Tyr Gln Gly Asp Glu Phe Lys Ile Arg Val Gly Asp Ala Leu Leu Gly
            100                 105                 110
```

-continued

```
Arg Leu Val Asp Gly Ile Gly Arg Pro Met Glu Ser Asn Ile Ala Ala
        115                 120                 125

Pro Tyr Leu Pro Phe Glu Arg Ser Leu Tyr Ala Glu Pro Pro Asp Pro
    130                 135                 140

Leu Leu Arg Gln Val Ile Asp Gln Pro Phe Ile Leu Gly Val Arg Ala
145                 150                 155                 160

Ile Asp Gly Leu Leu Thr Cys Gly Ile Gly Gln Arg Ile Gly Ile Phe
                165                 170                 175

Ala Gly Ser Gly Val Gly Lys Ser Thr Leu Leu Gly Met Ile Cys Asn
            180                 185                 190

Gly Ala Ser Ala Asp Ile Ile Val Leu Ala Leu Ile Gly Glu Arg Gly
        195                 200                 205

Arg Glu Val Asn Glu Phe Leu Ala Leu Leu Pro Gln Ser Thr Leu Ser
    210                 215                 220

Lys Cys Val Leu Val Val Thr Thr Ser Asp Arg Pro Ala Leu Glu Arg
225                 230                 235                 240

Met Lys Ala Ala Phe Thr Ala Thr Thr Ile Ala Glu Tyr Phe Arg Asp
                245                 250                 255

Gln Gly Lys Asn Val Leu Leu Met Met Asp Ser Val Thr Arg Tyr Ala
            260                 265                 270

Arg Ala Ala Arg Asp Val Gly Leu Ala Ser Gly Glu Pro Asp Val Arg
        275                 280                 285

Gly Gly Phe Pro Pro Ser Val Phe Ser Ser Leu Pro Lys Leu Leu Glu
    290                 295                 300

Arg Ala Gly Pro Ala Pro Lys Gly Ser Ile Thr Ala Ile Tyr Thr Val
305                 310                 315                 320

Leu Leu Glu Ser Asp Asn Val Asn Asp Pro Ile Gly Asp Glu Val Arg
                325                 330                 335

Ser Ile Leu Asp Gly His Ile Val Leu Thr Arg Glu Leu Ala Glu Glu
            340                 345                 350

Asn His Phe Pro Ala Ile Asp Ile Gly Leu Ser Ala Ser Arg Val Met
        355                 360                 365

His Asn Val Val Thr Ser Glu His Leu Arg Ala Ala Ala Glu Cys Lys
    370                 375                 380

Lys Leu Ile Ala Thr Tyr Lys Asn Val Glu Leu Leu Ile Arg Ile Gly
385                 390                 395                 400

Glu Tyr Thr Met Gly Gln Asp Pro Glu Ala Asp Lys Ala Ile Lys Asn
                405                 410                 415

Arg Lys Leu Ile Gln Asn Phe Ile Gln Gln Ser Thr Lys Asp Ile Ser
            420                 425                 430

Ser Tyr Glu Lys Thr Ile Glu Ser Leu Phe Lys Val Val Ala
        435                 440                 445
```

<210> SEQ ID NO 73
<211> LENGTH: 468
<212> TYPE: DNA
<213> ORGANISM: Shigella flexneri

<400> SEQUENCE: 73

```
atgtctttaa atatcaccga aaatgaaagc atctctactg cagtaattga tgcaattaac      60

tctggcgcta cactgaaaga tattaatgca attcctgatg atatgatgga tgacatttat     120

tcatatgctt atgactttta caacaaagga agaatagagg aagctgaagt tttcttcagg     180

tttttatgta tatacgactt ttacaatgta gactacatta tgggactcgc agctatttat     240
```

cagataaaag aacagttcca acaagcagca gacctttatg ctgtcgcttt tgcattagga 300
aaaaatgact atacaccagt attccatact ggacaatgcc agcttcggtt gaaagccccc 360
ttaaaagcta aagagtgctt cgaactcgta attcaacaca gcaatgatga aaaattaaaa 420
ataaaagcac aatcatactt ggacgcaatt caggatatca aggagtaa 468

<210> SEQ ID NO 74
<211> LENGTH: 155
<212> TYPE: PRT
<213> ORGANISM: Shigella flexneri

<400> SEQUENCE: 74

Met Ser Leu Asn Ile Thr Glu Asn Glu Ser Ile Ser Thr Ala Val Ile
1 5 10 15

Asp Ala Ile Asn Ser Gly Ala Thr Leu Lys Asp Ile Asn Ala Ile Pro
20 25 30

Asp Asp Met Met Asp Asp Ile Tyr Ser Tyr Ala Tyr Asp Phe Tyr Asn
35 40 45

Lys Gly Arg Ile Glu Glu Ala Glu Val Phe Phe Arg Phe Leu Cys Ile
50 55 60

Tyr Asp Phe Tyr Asn Val Asp Tyr Ile Met Gly Leu Ala Ala Ile Tyr
65 70 75 80

Gln Ile Lys Glu Gln Phe Gln Gln Ala Ala Asp Leu Tyr Ala Val Ala
85 90 95

Phe Ala Leu Gly Lys Asn Asp Tyr Thr Pro Val Phe His Thr Gly Gln
100 105 110

Cys Gln Leu Arg Leu Lys Ala Pro Leu Lys Ala Lys Glu Cys Phe Glu
115 120 125

Leu Val Ile Gln His Ser Asn Asp Glu Lys Leu Lys Ile Lys Ala Gln
130 135 140

Ser Tyr Leu Asp Ala Ile Gln Asp Ile Lys Glu
145 150 155

<210> SEQ ID NO 75
<211> LENGTH: 498
<212> TYPE: DNA
<213> ORGANISM: Salmonella enterica

<400> SEQUENCE: 75
atggattatc aaaataatgt cagcgaagaa cgtgttgcgg aaatgatttg ggatgccgtt 60
agtgaaggcg ccacgctaaa agacgttcat gggatccctc aagatatgat ggacggttta 120
tatgctcatg cttatgagtt ttataaccag ggacgactgg atgaagctga gacgttcttt 180
cgtttcttat gcatttatga tttttacaat cccgattaca ccatgggact ggcggcagta 240
tgccaactga aaaaacaatt tcagaaagca tgtgaccttt atgcagtagc gtttacgtta 300
cttaaaaatg attatcgccc cgtttttttt accgggcagt gtcaattatt aatgcgtaag 360
gcagcaaaag ccagacagtg ttttgaactt gtcaatgaac gtactgaaga tgagtctctg 420
cgggcaaaag cgttggtcta tctggaggcg ctaaaaacgg cggagacaga gcagcacagt 480
gaacaagaaa aggaataa 498

<210> SEQ ID NO 76
<211> LENGTH: 165
<212> TYPE: PRT
<213> ORGANISM: Salmonella enterica

<400> SEQUENCE: 76

Met Asp Tyr Gln Asn Asn Val Ser Glu Glu Arg Val Ala Glu Met Ile
1 5 10 15

Trp Asp Ala Val Ser Glu Gly Ala Thr Leu Lys Asp Val His Gly Ile
20 25 30

Pro Gln Asp Met Met Asp Gly Leu Tyr Ala His Ala Tyr Glu Phe Tyr
35 40 45

Asn Gln Gly Arg Leu Asp Glu Ala Glu Thr Phe Phe Arg Phe Leu Cys
50 55 60

Ile Tyr Asp Phe Tyr Asn Pro Asp Tyr Thr Met Gly Leu Ala Ala Val
65 70 75 80

Cys Gln Leu Lys Lys Gln Phe Gln Lys Ala Cys Asp Leu Tyr Ala Val
85 90 95

Ala Phe Thr Leu Leu Lys Asn Asp Tyr Arg Pro Val Phe Phe Thr Gly
100 105 110

Gln Cys Gln Leu Leu Met Arg Lys Ala Ala Lys Ala Arg Gln Cys Phe
115 120 125

Glu Leu Val Asn Glu Arg Thr Glu Asp Glu Ser Leu Arg Ala Lys Ala
130 135 140

Leu Val Tyr Leu Glu Ala Leu Lys Thr Ala Glu Thr Glu Gln His Ser
145 150 155 160

Glu Gln Glu Lys Glu
165

<210> SEQ ID NO 77
<211> LENGTH: 507
<212> TYPE: DNA
<213> ORGANISM: Yersinia pestis

<400> SEQUENCE: 77
atgcaacaag agacgacaga cactcaagaa taccagctgg caatggaatc cttcctaaaa 60
ggagggggaa ctatcgccat gctcaacgaa atttcaagtg acactttaga gcaactctac 120
tctcttgcat ttaaccaata ccagtcagga aaatacgagg atgctcacaa ggtctttcaa 180
gctctctgtg tgctagacca ctatgattca cgtttctttt tagggctagg cgcttgtcgt 240
caagccatgg ggcaatacga cttagcgatt catagctaca gctatggcgc cataatggat 300
ataaaagaac ctcgttttcc gtttcatgcg gccgaatgtt tactgcaaaa gggagagctt 360
gctgaagcag aaagtggctt gttcttggct caagagctta tcgcagacaa aactgagttt 420
aaggagcttt ccacccgagt tagctcaatg ttagaagcaa ttaaattgaa aaaggagatg 480
gaacatgagt gcgttgataa cccatga 507

<210> SEQ ID NO 78
<211> LENGTH: 168
<212> TYPE: PRT
<213> ORGANISM: Yersinia pestis

<400> SEQUENCE: 78

Met Gln Gln Glu Thr Thr Asp Thr Gln Glu Tyr Gln Leu Ala Met Glu
1 5 10 15

Ser Phe Leu Lys Gly Gly Gly Thr Ile Ala Met Leu Asn Glu Ile Ser
20 25 30

Ser Asp Thr Leu Glu Gln Leu Tyr Ser Leu Ala Phe Asn Gln Tyr Gln
35 40 45

Ser Gly Lys Tyr Glu Asp Ala His Lys Val Phe Gln Ala Leu Cys Val

```
    50                  55                  60

Leu Asp His Tyr Asp Ser Arg Phe Phe Leu Gly Leu Gly Ala Cys Arg
65                  70                  75                  80

Gln Ala Met Gly Gln Tyr Asp Leu Ala Ile His Ser Tyr Ser Tyr Gly
                85                  90                  95

Ala Ile Met Asp Ile Lys Glu Pro Arg Phe Pro Phe His Ala Ala Glu
            100                 105                 110

Cys Leu Leu Gln Lys Gly Glu Leu Ala Glu Ala Glu Ser Gly Leu Phe
        115                 120                 125

Leu Ala Gln Glu Leu Ile Ala Asp Lys Thr Glu Phe Lys Glu Leu Ser
    130                 135                 140

Thr Arg Val Ser Ser Met Leu Glu Ala Ile Lys Leu Lys Lys Glu Met
145                 150                 155                 160

Glu His Glu Cys Val Asp Asn Pro
                165
```

<210> SEQ ID NO 79
<211> LENGTH: 456
<212> TYPE: DNA
<213> ORGANISM: Escherichia coli

<400> SEQUENCE: 79

```
atgagcagga aatttagctc tctagaggat atttatgatt tctaccagga tggtggcaca      60

ttagcgtcat taacaaatct gacacaacaa gatctcaatg accttcattc ttatgcctat     120

acagcatatc aatctggtga tgtaataacc gcaagaaatc tattccattt gctcacatat     180

ctggaacact ggaattatga ctacacctta tctctgggct tatgccatca gcgtttatca     240

aatcatgaag atgcacaact gtgtttcgca cgctgtgcaa ctttagttat gcaagatccc     300

agggcatctt attattctgg aattagctac ttactcgtcg gaaataagaa aatggccaag     360

aaagccttta aggcttgttt aatgtggtgt aatgaaaaag aaaaatacac tacatataaa     420

gaaaatatta aaaaattgtt aggtaataca gagtaa                               456
```

<210> SEQ ID NO 80
<211> LENGTH: 151
<212> TYPE: PRT
<213> ORGANISM: Escherichia coli

<400> SEQUENCE: 80

```
Met Ser Arg Lys Phe Ser Ser Leu Glu Asp Ile Tyr Asp Phe Tyr Gln
1               5                   10                  15

Asp Gly Gly Thr Leu Ala Ser Leu Thr Asn Leu Thr Gln Gln Asp Leu
            20                  25                  30

Asn Asp Leu His Ser Tyr Ala Tyr Thr Ala Tyr Gln Ser Gly Asp Val
        35                  40                  45

Ile Thr Ala Arg Asn Leu Phe His Leu Leu Thr Tyr Leu Glu His Trp
    50                  55                  60

Asn Tyr Asp Tyr Thr Leu Ser Leu Gly Leu Cys His Gln Arg Leu Ser
65                  70                  75                  80

Asn His Glu Asp Ala Gln Leu Cys Phe Ala Arg Cys Ala Thr Leu Val
                85                  90                  95

Met Gln Asp Pro Arg Ala Ser Tyr Tyr Ser Gly Ile Ser Tyr Leu Leu
            100                 105                 110

Val Gly Asn Lys Lys Met Ala Lys Lys Ala Phe Lys Ala Cys Leu Met
        115                 120                 125
```

-continued

```
Trp Cys Asn Glu Lys Glu Lys Tyr Thr Thr Tyr Lys Glu Asn Ile Lys
    130                 135                 140

Lys Leu Leu Gly Asn Thr Glu
145                 150


<210> SEQ ID NO 81
<211> LENGTH: 1029
<212> TYPE: DNA
<213> ORGANISM: Shigella flexneri

<400> SEQUENCE: 81

atggcaaata aaacagaaaa gccgacacct aaaaaactaa aggatgccgc aaaaaaagga     60

cagtcattta aatttaagga tttaacgact gttgttatta ttctggtagg gacatttact    120

ataatatcat tcttttcctt aagtgatgta atgctcttat acagatatgt aataattaat    180

gacttcgaaa ttaatgaggg taaatacttt tttgcagtgg ttattgtctt ttttaagata    240

attggcttcc cacttttttt ctgtgttctt tcggctgtgt tgccaacatt ggttcaaaca    300

aagtttgttc ttgcgactaa agctatcaag attgattttt cagtattaaa ccctgttaaa    360

gggttaaaaa aaatatttag tataaagaca ataaaagaat ttttcaaaag cattctgctt    420

cttattattc tagcattaac aacctatttc ttttggatta atgaccgaaa aataattttt    480

tctcaggtgt tttctagtgt tgatggctta tatcttattt gggggaggct gtttaaggat    540

ataatattat ttttcttggc attttctatt cttgttatta ttcttgactt tgtgattgag    600

ttcattttat acatgaaaga tatgatgatg gataaacagg agataaaaag agaatatata    660

gagcaagagg gacactttga gacaaagtcg agaaggcgtg agttgcatat cgagattctt    720

tcagagcaga ctaaatctga tatacgtaat tcaaaattag tggtaatgaa cccgactcat    780

attgcaattg gtatttattt taatccagaa atagcgcctg caccttttat ttctctcatt    840

gaaactaacc agtgtgcctt ggctgtcaga aaatatgcaa atgaagttgg tataccgact    900

gtgcgtgatg tgaaattagc tagaaaacta tataaaacac atacaaaata tagttttgtt    960

gattttgaac acttggatga agtcctacgt cttattgttt ggcttgagca ggttgaaaac   1020

actcattaa                                                           1029


<210> SEQ ID NO 82
<211> LENGTH: 342
<212> TYPE: PRT
<213> ORGANISM: Shigella flexneri

<400> SEQUENCE: 82

Met Ala Asn Lys Thr Glu Lys Pro Thr Pro Lys Lys Leu Lys Asp Ala
1               5                   10                  15

Ala Lys Lys Gly Gln Ser Phe Lys Phe Lys Asp Leu Thr Thr Val Val
            20                  25                  30

Ile Ile Leu Val Gly Thr Phe Thr Ile Ile Ser Phe Phe Ser Leu Ser
        35                  40                  45

Asp Val Met Leu Leu Tyr Arg Tyr Val Ile Ile Asn Asp Phe Glu Ile
    50                  55                  60

Asn Glu Gly Lys Tyr Phe Phe Ala Val Val Ile Val Phe Phe Lys Ile
65                  70                  75                  80

Ile Gly Phe Pro Leu Phe Phe Cys Val Leu Ser Ala Val Leu Pro Thr
                85                  90                  95

Leu Val Gln Thr Lys Phe Val Leu Ala Thr Lys Ala Ile Lys Ile Asp
            100                 105                 110
```

-continued

```
Phe Ser Val Leu Asn Pro Val Lys Gly Leu Lys Lys Ile Phe Ser Ile
        115                 120                 125

Lys Thr Ile Lys Glu Phe Phe Lys Ser Ile Leu Leu Leu Ile Ile Leu
    130                 135                 140

Ala Leu Thr Thr Tyr Phe Phe Trp Ile Asn Asp Arg Lys Ile Ile Phe
145                 150                 155                 160

Ser Gln Val Phe Ser Ser Val Asp Gly Leu Tyr Leu Ile Trp Gly Arg
                165                 170                 175

Leu Phe Lys Asp Ile Ile Leu Phe Phe Leu Ala Phe Ser Ile Leu Val
            180                 185                 190

Ile Ile Leu Asp Phe Val Ile Glu Phe Ile Leu Tyr Met Lys Asp Met
        195                 200                 205

Met Met Asp Lys Gln Glu Ile Lys Arg Glu Tyr Ile Glu Gln Glu Gly
    210                 215                 220

His Phe Glu Thr Lys Ser Arg Arg Arg Glu Leu His Ile Glu Ile Leu
225                 230                 235                 240

Ser Glu Gln Thr Lys Ser Asp Ile Arg Asn Ser Lys Leu Val Val Met
                245                 250                 255

Asn Pro Thr His Ile Ala Ile Gly Ile Tyr Phe Asn Pro Glu Ile Ala
            260                 265                 270

Pro Ala Pro Phe Ile Ser Leu Ile Glu Thr Asn Gln Cys Ala Leu Ala
        275                 280                 285

Val Arg Lys Tyr Ala Asn Glu Val Gly Ile Pro Thr Val Arg Asp Val
    290                 295                 300

Lys Leu Ala Arg Lys Leu Tyr Lys Thr His Thr Lys Tyr Ser Phe Val
305                 310                 315                 320

Asp Phe Glu His Leu Asp Glu Val Leu Arg Leu Ile Val Trp Leu Glu
                325                 330                 335

Gln Val Glu Asn Thr His
            340
```

<210> SEQ ID NO 83
<211> LENGTH: 1071
<212> TYPE: DNA
<213> ORGANISM: Salmonella enterica

<400> SEQUENCE: 83

```
atgtcctcga ataaaacaga aaaaccgact aaaaaacggc tggaagactc cgctaaaaaa     60

ggccagtcat ttaaaagtaa agatctcatt atcgcctgcc tgacgctggg aggaattgcc    120

tatctggtgt cgtatggctc atttaatgag tttatgggga taattaagat cattattgcg    180

gataattttg atcagagcat ggctgactac agtttggccg tttttgggat agggttaaaa    240

tatctgattc catttatgct gctctgctta gtgtgttccg cattaccggc gttattacag    300

gccggttttg tgctggcgac agaagcatta aagcctaatt tatcggcgtt aaacccggta    360

gaaggggcaa aaaaactttt tagtatgcgc acggttaaag atacggtcaa aaccctactg    420

tatctctcat cctttgtggt ggccgccatc atttgctgga agaaatataa ggttgaaatc    480

ttttctcagc taaatggcaa tattgtaggt attgccgtca tttggcgtga acttctcctc    540

gcattggtat taacttgcct tgcttgcgca ttgattgtct tattattgga tgctattgcg    600

gaatatttcc tgaccatgaa agatatgaaa atggataagg aagaagtgaa gcgtgaaatg    660

aaggagcagg aagggaaccc agaggttaaa tctaaaagac gtgaagttca tatggaaatt    720

ctgtctgaac aggtgaaatc tgatattgaa aactcacgcc tgattgttgc caaccccacg    780
```

-continued

```
catattacga tcgggattta ttttaaaccc gaattgatgc cgattccgat gatctcggtg    840

tatgaaacga atcagcgcgc actggccgtc cgcgcctatg cggagaaggt tggcgtacct    900

gtgatcgtcg atatcaaact ggcgcgcagt cttttcaaaa cccatcgccg ttatgatctg    960

gtgagtctgg aagaaattga tgaagtttta cgtcttctgg tttggctgga agaggtagaa   1020

aacgcgggca aagacgttat tcagccacaa gaaaacgagg tacggcattg a            1071


<210> SEQ ID NO 84
<211> LENGTH: 356
<212> TYPE: PRT
<213> ORGANISM: Salmonella enterica

<400> SEQUENCE: 84

Met Ser Ser Asn Lys Thr Glu Lys Pro Thr Lys Lys Arg Leu Glu Asp
1               5                   10                  15

Ser Ala Lys Lys Gly Gln Ser Phe Lys Ser Lys Asp Leu Ile Ile Ala
            20                  25                  30

Cys Leu Thr Leu Gly Gly Ile Ala Tyr Leu Val Ser Tyr Gly Ser Phe
        35                  40                  45

Asn Glu Phe Met Gly Ile Ile Lys Ile Ile Ile Ala Asp Asn Phe Asp
    50                  55                  60

Gln Ser Met Ala Asp Tyr Ser Leu Ala Val Phe Gly Ile Gly Leu Lys
65                  70                  75                  80

Tyr Leu Ile Pro Phe Met Leu Leu Cys Leu Val Cys Ser Ala Leu Pro
                85                  90                  95

Ala Leu Leu Gln Ala Gly Phe Val Leu Ala Thr Glu Ala Leu Lys Pro
            100                 105                 110

Asn Leu Ser Ala Leu Asn Pro Val Glu Gly Ala Lys Lys Leu Phe Ser
        115                 120                 125

Met Arg Thr Val Lys Asp Thr Val Lys Thr Leu Leu Tyr Leu Ser Ser
    130                 135                 140

Phe Val Val Ala Ala Ile Ile Cys Trp Lys Lys Tyr Lys Val Glu Ile
145                 150                 155                 160

Phe Ser Gln Leu Asn Gly Asn Ile Val Gly Ile Ala Val Ile Trp Arg
                165                 170                 175

Glu Leu Leu Leu Ala Leu Val Leu Thr Cys Leu Ala Cys Ala Leu Ile
            180                 185                 190

Val Leu Leu Leu Asp Ala Ile Ala Glu Tyr Phe Leu Thr Met Lys Asp
        195                 200                 205

Met Lys Met Asp Lys Glu Glu Val Lys Arg Glu Met Lys Glu Gln Glu
    210                 215                 220

Gly Asn Pro Glu Val Lys Ser Lys Arg Arg Glu Val His Met Glu Ile
225                 230                 235                 240

Leu Ser Glu Gln Val Lys Ser Asp Ile Glu Asn Ser Arg Leu Ile Val
                245                 250                 255

Ala Asn Pro Thr His Ile Thr Ile Gly Ile Tyr Phe Lys Pro Glu Leu
            260                 265                 270

Met Pro Ile Pro Met Ile Ser Val Tyr Glu Thr Asn Gln Arg Ala Leu
        275                 280                 285

Ala Val Arg Ala Tyr Ala Glu Lys Val Gly Val Pro Val Ile Val Asp
    290                 295                 300

Ile Lys Leu Ala Arg Ser Leu Phe Lys Thr His Arg Arg Tyr Asp Leu
305                 310                 315                 320

Val Ser Leu Glu Glu Ile Asp Glu Val Leu Arg Leu Leu Val Trp Leu
```

-continued

```
                325                 330                 335

Glu Glu Val Glu Asn Ala Gly Lys Asp Val Ile Gln Pro Gln Glu Asn
            340                 345                 350

Glu Val Arg His
        355


<210> SEQ ID NO 85
<211> LENGTH: 1065
<212> TYPE: DNA
<213> ORGANISM: Yersinia pestis

<400> SEQUENCE: 85

atgagcggag aaaagacaga gcaacccacc ccgaagaaaa tccgtgatgc gcgcaaaaag      60

ggacaggtag cgaaaagtaa ggaagtggtc tctactgcgc ttatcgtcgc gctgagtgcg     120

atgttaatgg ggctttctga ctactatttc gagcatttta gtaagctgat gctaatcccc     180

gcagagcaga gctatcttcc tttctcgcag gcgcttagct atgtggttga caatgtgttg     240

ctcgagtttt tttatctctg ttttcctttg ttaacagtgg cggcattaat ggcgatcgca     300

tctcatgttg tgcagtatgg ttttcttata agtggtgaag caattaaacc ggatattaaa     360

aaaatcaatc caatagaggg tgccaagcgt atcttttcca tcaaaagttt agtggagttt     420

ctcaaatcca ttctcaaggt tgttttgctc agtatactca tctggataat cattaaggga     480

aatctagtca cactcttgca gttgccaacc tgtggaattg aatgtattac ccctttattg     540

gggcaaatac tccggcagtt gatggttatc tgtactgttg gctttgtggt catctccata     600

gccgactatg cctttgaata ctatcaatat attaaggaac ttaaaatgag caaggatgag     660

atcaaacgcg agtacaaaga aatggagggt agcccagaaa tcaaaagcaa gcgtcgtcag     720

tttcatcaag agatccaatc gaggaacatg cgggaaaatg ttaaacgctc atcagtggtg     780

gtagctaatc cgacccatat tgctattggt attctttaca agcgaggggga aacaccacta    840

ccgttggtaa cattcaaata taccgatgcc caagttcaga ctgtgcgcaa aatagcagaa     900

gaagaagggg tgcctatttt acaacgtatc ccattagccc gtgctcttta ttggatgcg      960

ctcgtcgatc actatattcc ggctgagcaa atagaggcca cagctgaagt gctacgatgg    1020

ctagaaaggc aaaatatcga gaaacaacat tccgaaatgt tataa                    1065


<210> SEQ ID NO 86
<211> LENGTH: 354
<212> TYPE: PRT
<213> ORGANISM: Yersinia pestis

<400> SEQUENCE: 86

Met Ser Gly Glu Lys Thr Glu Gln Pro Thr Pro Lys Lys Ile Arg Asp
1               5                   10                  15

Ala Arg Lys Lys Gly Gln Val Ala Lys Ser Lys Glu Val Val Ser Thr
            20                  25                  30

Ala Leu Ile Val Ala Leu Ser Ala Met Leu Met Gly Leu Ser Asp Tyr
        35                  40                  45

Tyr Phe Glu His Phe Ser Lys Leu Met Leu Ile Pro Ala Glu Gln Ser
    50                  55                  60

Tyr Leu Pro Phe Ser Gln Ala Leu Ser Tyr Val Val Asp Asn Val Leu
65                  70                  75                  80

Leu Glu Phe Phe Tyr Leu Cys Phe Pro Leu Leu Thr Val Ala Ala Leu
                85                  90                  95

Met Ala Ile Ala Ser His Val Val Gln Tyr Gly Phe Leu Ile Ser Gly
```

100 105 110

Glu Ala Ile Lys Pro Asp Ile Lys Lys Ile Asn Pro Ile Glu Gly Ala
115 120 125

Lys Arg Ile Phe Ser Ile Lys Ser Leu Val Glu Phe Leu Lys Ser Ile
130 135 140

Leu Lys Val Val Leu Leu Ser Ile Leu Ile Trp Ile Ile Ile Lys Gly
145 150 155 160

Asn Leu Val Thr Leu Leu Gln Leu Pro Thr Cys Gly Ile Glu Cys Ile
165 170 175

Thr Pro Leu Leu Gly Gln Ile Leu Arg Gln Leu Met Val Ile Cys Thr
180 185 190

Val Gly Phe Val Val Ile Ser Ile Ala Asp Tyr Ala Phe Glu Tyr Tyr
195 200 205

Gln Tyr Ile Lys Glu Leu Lys Met Ser Lys Asp Glu Ile Lys Arg Glu
210 215 220

Tyr Lys Glu Met Glu Gly Ser Pro Glu Ile Lys Ser Lys Arg Arg Gln
225 230 235 240

Phe His Gln Glu Ile Gln Ser Arg Asn Met Arg Glu Asn Val Lys Arg
245 250 255

Ser Ser Val Val Val Ala Asn Pro Thr His Ile Ala Ile Gly Ile Leu
260 265 270

Tyr Lys Arg Gly Glu Thr Pro Leu Pro Leu Val Thr Phe Lys Tyr Thr
275 280 285

Asp Ala Gln Val Gln Thr Val Arg Lys Ile Ala Glu Glu Glu Gly Val
290 295 300

Pro Ile Leu Gln Arg Ile Pro Leu Ala Arg Ala Leu Tyr Trp Asp Ala
305 310 315 320

Leu Val Asp His Tyr Ile Pro Ala Glu Gln Ile Glu Ala Thr Ala Glu
325 330 335

Val Leu Arg Trp Leu Glu Arg Gln Asn Ile Glu Lys Gln His Ser Glu
340 345 350

Met Leu

<210> SEQ ID NO 87
<211> LENGTH: 1038
<212> TYPE: DNA
<213> ORGANISM: Escherichia coli

<400> SEQUENCE: 87
atgagtgaaa aaacagaaaa gcccacaccc aaaaaactga gggatctaaa aaagaagggc 60
gatgtaacaa aaagtgaaga ggtaatggct gcagtgcagt cattaatctt attttcattt 120
ttttctttat atggcatgag tttttttgtt gatatagttg ggttagttaa tacgacaata 180
gactcgctaa atagaccgtt tttgtatgcc attcgagaaa tattaggtgc ggtgttaaat 240
atatttttat tatatatttt gccaatttct ttgattgtct ttgttggaac tgttacgact 300
ggtgtatcac aaataggatt catctttgcg gttgaaaaaa taaaaccatc ggctcagaag 360
attagtgtaa aaaataacct gaaaaatatt ttttctgtaa agagcatttt tgagctactt 420
aaatcagtat ttaagttagt gataattgtt ctcatttttt attttatggg gcattcatat 480
gcaaatgagt ttgctaattt cacaggactg aacgcatatc aagctcttgt cgttgttgcc 540
ttttttgttt ttcttttatg gaaaggcgtg ctattcggat atctactctt ttcagtattt 600
gatttctggt tccagaagca tgagggactg aagaaaatga aaatgagtaa agatgaggtg 660

-continued

```
aaacgagaag ccaaggatac tgatggtaac cctgaaatta aaggggagcg ccgtcgcctt    720

cattccgaga tacaaagtgg aagtttggcg aataacatca aaaaatcaac cgttattgtt    780

aaaaacccga ctcacattgc gatttgccta tactataaac ttggggagac tccattacct    840

ttagttattg aaacaggaaa agatgccaaa gctctacaga tcattaaact ggctgaactc    900

tatgatattc cagtgattga agatattcct ttagcaagaa gtctctataa gaatatacat    960

aaaggacaat atataacaga agactttttt gaacctgtgg cacaattgat tcgtattgcg   1020

atagaccttg attattaa                                                 1038
```

<210> SEQ ID NO 88
<211> LENGTH: 345
<212> TYPE: PRT
<213> ORGANISM: Escherichia coli

<400> SEQUENCE: 88

```
Met Ser Glu Lys Thr Glu Lys Pro Thr Pro Lys Lys Leu Arg Asp Leu
1               5                   10                  15

Lys Lys Lys Gly Asp Val Thr Lys Ser Glu Glu Val Met Ala Ala Val
            20                  25                  30

Gln Ser Leu Ile Leu Phe Ser Phe Phe Ser Leu Tyr Gly Met Ser Phe
        35                  40                  45

Phe Val Asp Ile Val Gly Leu Val Asn Thr Thr Ile Asp Ser Leu Asn
    50                  55                  60

Arg Pro Phe Leu Tyr Ala Ile Arg Glu Ile Leu Gly Ala Val Leu Asn
65                  70                  75                  80

Ile Phe Leu Leu Tyr Ile Leu Pro Ile Ser Leu Ile Val Phe Val Gly
                85                  90                  95

Thr Val Thr Thr Gly Val Ser Gln Ile Gly Phe Ile Phe Ala Val Glu
            100                 105                 110

Lys Ile Lys Pro Ser Ala Gln Lys Ile Ser Val Lys Asn Asn Leu Lys
        115                 120                 125

Asn Ile Phe Ser Val Lys Ser Ile Phe Glu Leu Leu Lys Ser Val Phe
    130                 135                 140

Lys Leu Val Ile Ile Val Leu Ile Phe Tyr Phe Met Gly His Ser Tyr
145                 150                 155                 160

Ala Asn Glu Phe Ala Asn Phe Thr Gly Leu Asn Ala Tyr Gln Ala Leu
                165                 170                 175

Val Val Val Ala Phe Phe Val Phe Leu Leu Trp Lys Gly Val Leu Phe
            180                 185                 190

Gly Tyr Leu Leu Phe Ser Val Phe Asp Phe Trp Phe Gln Lys His Glu
        195                 200                 205

Gly Leu Lys Lys Met Lys Met Ser Lys Asp Glu Val Lys Arg Glu Ala
    210                 215                 220

Lys Asp Thr Asp Gly Asn Pro Glu Ile Lys Gly Glu Arg Arg Arg Leu
225                 230                 235                 240

His Ser Glu Ile Gln Ser Gly Ser Leu Ala Asn Asn Ile Lys Lys Ser
                245                 250                 255

Thr Val Ile Val Lys Asn Pro Thr His Ile Ala Ile Cys Leu Tyr Tyr
            260                 265                 270

Lys Leu Gly Glu Thr Pro Leu Pro Leu Val Ile Glu Thr Gly Lys Asp
        275                 280                 285

Ala Lys Ala Leu Gln Ile Ile Lys Leu Ala Glu Leu Tyr Asp Ile Pro
    290                 295                 300
```

Val Ile Glu Asp Ile Pro Leu Ala Arg Ser Leu Tyr Lys Asn Ile His
305 310 315 320

Lys Gly Gln Tyr Ile Thr Glu Asp Phe Phe Glu Pro Val Ala Gln Leu
325 330 335

Ile Arg Ile Ala Ile Asp Leu Asp Tyr
340 345

<210> SEQ ID NO 89
<211> LENGTH: 1068
<212> TYPE: DNA
<213> ORGANISM: Shigella flexneri

<400> SEQUENCE: 89
atgcttgatg ttaaaaatac aggagttttt agctctgcat tcattgatag gttgaatgca 60
atgacaaatt cagatgatgg agatgagact gctgatgcag agcttgattc tggcttggct 120
aatagcaagt atattgactc atctgatgag atggcttccg ctctttcgtc atttataaac 180
agaagagacc ttgagaaact gaaaggaaca aatagtgata gtcaggaacg tattttagat 240
ggggaagaag atgaaattaa tcacaagatt tttgatttaa agagaacgtt aaaagataac 300
cttcctctag atcgggattt tatagacaga ctaaagagat attttaaaga tccaagtgat 360
caagtcttag cattaaggga acttttgaat gaaaaagatc ttactgctga acaagtcgaa 420
ttattaacta aaattattaa tgagataata tcaggtagtg aaaaaagtgt taatgctgga 480
ataaattcag ctatacaggc taaattattt ggcaacaaaa tgaaacttga accacagctt 540
ttgcgtgcat gttatcgtgg ttttatcatg gggaacatat caacaacaga tcagtatata 600
gaatggcttg gtaattttgg ttttaatcac agacatacaa ttgtgaattt tgtagagcag 660
tcactgattg tagacatgga ttctgagaaa ccgagctgta atgcttatga gtttggtttt 720
gtgttatcta aattaattgc aattaagatg attagaactt cagacgtaat tttatgaag 780 aaactggaat cctcaagctt gctaaaagat ggcagtttaa gtgcagagca gctattgcta 840
actttattat atatttttca atatccaagt gaaagtgagc aaattcttac ttctgttata 900
gaagtatcac gagccagtca tgaggattct gtagtgtatc aaacatatct atcttctgtt 960
aatgaaagtc ctcatgatat atttaaaagt gaaagtgaaa gagaaattgc gatcaatatt 1020
ctacgagagc ttgtcacaag tgcatacaag aaagagcttt ctagataa 1068

<210> SEQ ID NO 90
<211> LENGTH: 355
<212> TYPE: PRT
<213> ORGANISM: Shigella flexneri

<400> SEQUENCE: 90

Met Leu Asp Val Lys Asn Thr Gly Val Phe Ser Ser Ala Phe Ile Asp
1 5 10 15

Arg Leu Asn Ala Met Thr Asn Ser Asp Asp Gly Asp Glu Thr Ala Asp
20 25 30

Ala Glu Leu Asp Ser Gly Leu Ala Asn Ser Lys Tyr Ile Asp Ser Ser
35 40 45

Asp Glu Met Ala Ser Ala Leu Ser Ser Phe Ile Asn Arg Arg Asp Leu
50 55 60

Glu Lys Leu Lys Gly Thr Asn Ser Asp Ser Gln Glu Arg Ile Leu Asp
65 70 75 80

Gly Glu Glu Asp Glu Ile Asn His Lys Ile Phe Asp Leu Lys Arg Thr
85 90 95

-continued

```
Leu Lys Asp Asn Leu Pro Leu Asp Arg Asp Phe Ile Asp Arg Leu Lys
            100                 105                 110

Arg Tyr Phe Lys Asp Pro Ser Asp Gln Val Leu Ala Leu Arg Glu Leu
        115                 120                 125

Leu Asn Glu Lys Asp Leu Thr Ala Glu Gln Val Glu Leu Leu Thr Lys
    130                 135                 140

Ile Ile Asn Glu Ile Ile Ser Gly Ser Glu Lys Ser Val Asn Ala Gly
145                 150                 155                 160

Ile Asn Ser Ala Ile Gln Ala Lys Leu Phe Gly Asn Lys Met Lys Leu
                165                 170                 175

Glu Pro Gln Leu Leu Arg Ala Cys Tyr Arg Gly Phe Ile Met Gly Asn
            180                 185                 190

Ile Ser Thr Thr Asp Gln Tyr Ile Glu Trp Leu Gly Asn Phe Gly Phe
        195                 200                 205

Asn His Arg His Thr Ile Val Asn Phe Val Glu Gln Ser Leu Ile Val
    210                 215                 220

Asp Met Asp Ser Glu Lys Pro Ser Cys Asn Ala Tyr Glu Phe Gly Phe
225                 230                 235                 240

Val Leu Ser Lys Leu Ile Ala Ile Lys Met Ile Arg Thr Ser Asp Val
                245                 250                 255

Ile Phe Met Lys Lys Leu Glu Ser Ser Ser Leu Leu Lys Asp Gly Ser
            260                 265                 270

Leu Ser Ala Glu Gln Leu Leu Leu Thr Leu Leu Tyr Ile Phe Gln Tyr
        275                 280                 285

Pro Ser Glu Ser Glu Gln Ile Leu Thr Ser Val Ile Glu Val Ser Arg
    290                 295                 300

Ala Ser His Glu Asp Ser Val Val Tyr Gln Thr Tyr Leu Ser Ser Val
305                 310                 315                 320

Asn Glu Ser Pro His Asp Ile Phe Lys Ser Glu Ser Glu Arg Glu Ile
                325                 330                 335

Ala Ile Asn Ile Leu Arg Glu Leu Val Thr Ser Ala Tyr Lys Lys Glu
            340                 345                 350

Leu Ser Arg
        355
```

<210> SEQ ID NO 91
<211> LENGTH: 1119
<212> TYPE: DNA
<213> ORGANISM: Salmonella enterica

<400> SEQUENCE: 91

```
atgattcctg gctcaacctc cggtatttca ttttccagaa tattgtcccg gcagacatct      60

catcaggatg cgacccagca tactgatgcg caacaggcgg aaatacaaca ggccgcagag     120

gattcgtctc caggggcgga agtacaaaaa tttgtccagt cgacggacga aatgtcagcg     180

gcgctggcgc aatttcgtaa ccgtcgcgat tatgaaaaaa aatccagtaa tttatctaac     240

agttttgaac gcgtgctgga ggatgaggct ttaccgaagg cgaagcaaat cttaaagcta     300

attagcgtac atggcggcgc gttagaagat tttttacgtc aggcgcgtag cttatttcct     360

gaccccagtg atttagtcct tgtgttacgc gaattgcttc gtcgtaaaga cctggaagag     420

atcgtgcgga aaaagctgga gtcgttactt aagcacgttg aagagcaaac cgatccgaag     480

accctcaagg cagggattaa ttgtgcgttg aaggcccggc tttttgggaa aacattatcg     540

ttaaaaccag gcttattgcg cgccagctat cggcaattta tccagagtga atcacatgaa     600
```

```
gtggagattt actctgactg gatagccagt tatggctatc aacgtcgact ggtggtactg    660

gattttattg agggttcgct attaaccgat attgacgcga atgacgccag ctgttcgcgc    720

ctggagtttg gccagctttt acgacgcctg acgcaactta aaatgttgcg ctccgctgac    780

ctactgtttg tgagtacatt gttgtcgtat tcgtttacca aagcgtttaa tgcggaggag    840

tcgtcgtggt tactactgat gctttcgcta ttgcaacagc cacatgaagt ggattcgctg    900

ttagccgata ttataggttt gaatgcgtta ttgcttagtc ataaagaaca tgcatccttt    960

ttgcagatat tttatcaagt atgtaaagcc ataccctctt cactctttta tgaagaatat   1020

tggcaggaag aattgttaat ggcgttacgt agtatgaccg atattgccta caagcatgaa   1080

atggcagaac agcgtcgtac tattgaaaag ctgtcttaa                          1119
```

<210> SEQ ID NO 92
<211> LENGTH: 372
<212> TYPE: PRT
<213> ORGANISM: Salmonella enterica

<400> SEQUENCE: 92

```
Met Ile Pro Gly Ser Thr Ser Gly Ile Ser Phe Ser Arg Ile Leu Ser
1               5                   10                  15

Arg Gln Thr Ser His Gln Asp Ala Thr Gln His Thr Asp Ala Gln Gln
            20                  25                  30

Ala Glu Ile Gln Gln Ala Ala Glu Asp Ser Ser Pro Gly Ala Glu Val
        35                  40                  45

Gln Lys Phe Val Gln Ser Thr Asp Glu Met Ser Ala Ala Leu Ala Gln
    50                  55                  60

Phe Arg Asn Arg Arg Asp Tyr Glu Lys Lys Ser Ser Asn Leu Ser Asn
65                  70                  75                  80

Ser Phe Glu Arg Val Leu Glu Asp Glu Ala Leu Pro Lys Ala Lys Gln
                85                  90                  95

Ile Leu Lys Leu Ile Ser Val His Gly Gly Ala Leu Glu Asp Phe Leu
            100                 105                 110

Arg Gln Ala Arg Ser Leu Phe Pro Asp Pro Ser Asp Leu Val Leu Val
        115                 120                 125

Leu Arg Glu Leu Leu Arg Arg Lys Asp Leu Glu Glu Ile Val Arg Lys
    130                 135                 140

Lys Leu Glu Ser Leu Leu Lys His Val Glu Glu Gln Thr Asp Pro Lys
145                 150                 155                 160

Thr Leu Lys Ala Gly Ile Asn Cys Ala Leu Lys Ala Arg Leu Phe Gly
                165                 170                 175

Lys Thr Leu Ser Leu Lys Pro Gly Leu Leu Arg Ala Ser Tyr Arg Gln
            180                 185                 190

Phe Ile Gln Ser Glu Ser His Glu Val Glu Ile Tyr Ser Asp Trp Ile
        195                 200                 205

Ala Ser Tyr Gly Tyr Gln Arg Arg Leu Val Val Leu Asp Phe Ile Glu
    210                 215                 220

Gly Ser Leu Leu Thr Asp Ile Asp Ala Asn Asp Ala Ser Cys Ser Arg
225                 230                 235                 240

Leu Glu Phe Gly Gln Leu Leu Arg Arg Leu Thr Gln Leu Lys Met Leu
                245                 250                 255

Arg Ser Ala Asp Leu Leu Phe Val Ser Thr Leu Leu Ser Tyr Ser Phe
            260                 265                 270

Thr Lys Ala Phe Asn Ala Glu Glu Ser Ser Trp Leu Leu Leu Met Leu
        275                 280                 285
```

```
Ser Leu Leu Gln Gln Pro His Glu Val Asp Ser Leu Leu Ala Asp Ile
    290                 295                 300

Ile Gly Leu Asn Ala Leu Leu Leu Ser His Lys Glu His Ala Ser Phe
305                 310                 315                 320

Leu Gln Ile Phe Tyr Gln Val Cys Lys Ala Ile Pro Ser Ser Leu Phe
                325                 330                 335

Tyr Glu Glu Tyr Trp Gln Glu Glu Leu Leu Met Ala Leu Arg Ser Met
            340                 345                 350

Thr Asp Ile Ala Tyr Lys His Glu Met Ala Glu Gln Arg Arg Thr Ile
        355                 360                 365

Glu Lys Leu Ser
    370


<210> SEQ ID NO 93
<211> LENGTH: 882
<212> TYPE: DNA
<213> ORGANISM: Yersinia pestis

<400> SEQUENCE: 93

atgacgacgc ttcataacct atcttatggc aataccccgc tgcataatga gcgtccagag      60

attgccagta gtcagatcgt aaatcagact ctgggtcaat ttcgggggaga atctgtgcag    120

atagtcagcg gcactctgca gtctatagct gatatggcag aagaggtaac atttgtcttc    180

tccgagcgta aggagttctc cctcgacaaa cgcaaattaa gtgacagcca ggctcgagtt    240

agcgacgttg aggagcaggt taatcaatac cttagcaaag ttccagagtt ggaacaaaaa    300

cagaatgtga gtgagctgct cagtctgttg agtaacagcc ccaatataag cttgtcccag    360

ttaaaggctt atctggaggg gaaatcagaa gaaccgagtg agcaattcaa aatgctctgc    420

ggcttgcgtg atgccctgaa agggcgccct gaattagcac atctttcgca tttggttgaa    480

caagctctgg tcagcatggc tgaagagcaa ggagaaacca ttgtattggg tgccaggata    540

accccggaag cgtacagaga atcccagtcg ggtgttaatc cactgcagcc gctccgtgat    600

acctaccgcg atgcagtgat gggttatcaa ggaatttatg cgatctggag tgatttacaa    660

aaacgttttc ctaatgggga tatagactcg gtgatattat tcctgcaaaa ggcgcttagt    720

gcagatctac aaagtcaaca aagcgggtct ggacgggaaa aattaggaat agttattagt    780

gacttacaga agctaaagga gtttggtagc gtgagtgacc aagttaaagg attttggcaa    840

ttttttttcag agggtaaaac taatggcgta cgacctttct ga                        882


<210> SEQ ID NO 94
<211> LENGTH: 293
<212> TYPE: PRT
<213> ORGANISM: Yersinia pestis

<400> SEQUENCE: 94

Met Thr Thr Leu His Asn Leu Ser Tyr Gly Asn Thr Pro Leu His Asn
1               5                   10                  15

Glu Arg Pro Glu Ile Ala Ser Ser Gln Ile Val Asn Gln Thr Leu Gly
            20                  25                  30

Gln Phe Arg Gly Glu Ser Val Gln Ile Val Ser Gly Thr Leu Gln Ser
        35                  40                  45

Ile Ala Asp Met Ala Glu Glu Val Thr Phe Val Phe Ser Glu Arg Lys
    50                  55                  60

Glu Phe Ser Leu Asp Lys Arg Lys Leu Ser Asp Ser Gln Ala Arg Val
65                  70                  75                  80
```

```
Ser Asp Val Glu Glu Gln Val Asn Gln Tyr Leu Ser Lys Val Pro Glu
                85                  90                  95

Leu Glu Gln Lys Gln Asn Val Ser Glu Leu Leu Ser Leu Leu Ser Asn
            100                 105                 110

Ser Pro Asn Ile Ser Leu Ser Gln Leu Lys Ala Tyr Leu Glu Gly Lys
        115                 120                 125

Ser Glu Glu Pro Ser Glu Gln Phe Lys Met Leu Cys Gly Leu Arg Asp
    130                 135                 140

Ala Leu Lys Gly Arg Pro Glu Leu Ala His Leu Ser His Leu Val Glu
145                 150                 155                 160

Gln Ala Leu Val Ser Met Ala Glu Glu Gln Gly Glu Thr Ile Val Leu
                165                 170                 175

Gly Ala Arg Ile Thr Pro Glu Ala Tyr Arg Glu Ser Gln Ser Gly Val
            180                 185                 190

Asn Pro Leu Gln Pro Leu Arg Asp Thr Tyr Arg Asp Ala Val Met Gly
        195                 200                 205

Tyr Gln Gly Ile Tyr Ala Ile Trp Ser Asp Leu Gln Lys Arg Phe Pro
    210                 215                 220

Asn Gly Asp Ile Asp Ser Val Ile Leu Phe Leu Gln Lys Ala Leu Ser
225                 230                 235                 240

Ala Asp Leu Gln Ser Gln Gln Ser Gly Ser Gly Arg Glu Lys Leu Gly
                245                 250                 255

Ile Val Ile Ser Asp Leu Gln Lys Leu Lys Glu Phe Gly Ser Val Ser
            260                 265                 270

Asp Gln Val Lys Gly Phe Trp Gln Phe Phe Ser Glu Gly Lys Thr Asn
        275                 280                 285

Gly Val Arg Pro Phe
    290
```

<210> SEQ ID NO 95
<211> LENGTH: 1056
<212> TYPE: DNA
<213> ORGANISM: Escherichia coli

<400> SEQUENCE: 95

```
atggctaatg gtattgaatt taatcaaaac cccgcatctg tttttaattc taattcatta      60

gattttgaat tagaatctca gcaattaacg caaaaaaatt cttctaatat ttcttcgcca     120

ttaataaatt tgcaaaatga attagcaatg attactagtt catcgctttc tgaaacgatt     180

gaagggctaa gcctgggata tcgcaaaggt agcgcaagga aagaagagga aggctcgaca     240

atcgagaagc tgctcaatga tatgcaagag ctgcttactc ttaccgatag tgataaaata     300

aaagaactat cattaaaaaa cagcgggctg ctggaacaac acgatcctac tttggcgatg     360

tttggcaaca tgccaaaggg ggaaattgtt gcgctaatat cttctttatt gcaatctaag     420

tttgttaaga ttgaattaaa aaagaaatat gccaggttat tattagattt attaggcgaa     480

gatgattggg agctggctct gctttcctgg ttaggggtgg gtgagttaaa tcaggaaggt     540

atccagaaga tcaagaagct ttatgaaaag gctaaggatg aggattctga aaatggcgcc     600

tctttacttg actggtttat ggagattaag gatcttcccg agcgtgagaa gcacttaaaa     660

gtcattatta gggcgctgtc gttcgatctc tcttatatgt cttcttttga agacaaagta     720

aagacatctt caattattag tgatttatgc agggtaatca ttttttttatc acttgataac     780

tatgcagata ttatttcgat ctctattaag aaagataaag atatcatttt aaatgaagtg     840
```

```
ttatcgatta ttgaacatgt ctggctaaca gaagactggt tgctggagag tccttctcgg    900

gtatcgattg tcgaagataa acatatttat tattttcatt tattgaaaga ctttttttaca    960

tcattaccag atgcttgctt tattgatagt gagcagagag agaatgcatt attaatgatt   1020

ggtaaagtta tcgactataa ggaggaaatt atttga                             1056


<210> SEQ ID NO 96
<211> LENGTH: 351
<212> TYPE: PRT
<213> ORGANISM: Escherichia coli

<400> SEQUENCE: 96

Met Ala Asn Gly Ile Glu Phe Asn Gln Asn Pro Ala Ser Val Phe Asn
1               5                   10                  15

Ser Asn Ser Leu Asp Phe Glu Leu Glu Ser Gln Gln Leu Thr Gln Lys
            20                  25                  30

Asn Ser Ser Asn Ile Ser Ser Pro Leu Ile Asn Leu Gln Asn Glu Leu
        35                  40                  45

Ala Met Ile Thr Ser Ser Ser Leu Ser Glu Thr Ile Glu Gly Leu Ser
    50                  55                  60

Leu Gly Tyr Arg Lys Gly Ser Ala Arg Lys Glu Glu Glu Gly Ser Thr
65                  70                  75                  80

Ile Glu Lys Leu Leu Asn Asp Met Gln Glu Leu Leu Thr Leu Thr Asp
                85                  90                  95

Ser Asp Lys Ile Lys Glu Leu Ser Leu Lys Asn Ser Gly Leu Leu Glu
            100                 105                 110

Gln His Asp Pro Thr Leu Ala Met Phe Gly Asn Met Pro Lys Gly Glu
        115                 120                 125

Ile Val Ala Leu Ile Ser Ser Leu Leu Gln Ser Lys Phe Val Lys Ile
    130                 135                 140

Glu Leu Lys Lys Lys Tyr Ala Arg Leu Leu Leu Asp Leu Leu Gly Glu
145                 150                 155                 160

Asp Asp Trp Glu Leu Ala Leu Leu Ser Trp Leu Gly Val Gly Glu Leu
                165                 170                 175

Asn Gln Glu Gly Ile Gln Lys Ile Lys Lys Leu Tyr Glu Lys Ala Lys
            180                 185                 190

Asp Glu Asp Ser Glu Asn Gly Ala Ser Leu Leu Asp Trp Phe Met Glu
        195                 200                 205

Ile Lys Asp Leu Pro Glu Arg Glu Lys His Leu Lys Val Ile Ile Arg
    210                 215                 220

Ala Leu Ser Phe Asp Leu Ser Tyr Met Ser Ser Phe Glu Asp Lys Val
225                 230                 235                 240

Lys Thr Ser Ser Ile Ile Ser Asp Leu Cys Arg Val Ile Ile Phe Leu
                245                 250                 255

Ser Leu Asp Asn Tyr Ala Asp Ile Ile Ser Ile Ser Ile Lys Lys Asp
            260                 265                 270

Lys Asp Ile Ile Leu Asn Glu Val Leu Ser Ile Ile Glu His Val Trp
        275                 280                 285

Leu Thr Glu Asp Trp Leu Leu Glu Ser Pro Ser Arg Val Ser Ile Val
    290                 295                 300

Glu Asp Lys His Ile Tyr Tyr Phe His Leu Leu Lys Asp Phe Phe Thr
305                 310                 315                 320

Ser Leu Pro Asp Ala Cys Phe Ile Asp Ser Glu Gln Arg Glu Asn Ala
                325                 330                 335
```

```
Leu Leu Met Ile Gly Lys Val Ile Asp Tyr Lys Glu Glu Ile Ile
            340                 345                 350


<210> SEQ ID NO 97
<211> LENGTH: 208
<212> TYPE: PRT
<213> ORGANISM: Shigella flexneri

<400> SEQUENCE: 97

Met Gln Ile Leu Asn Lys Ile Leu Pro Gln Val Glu Phe Ala Ile Pro
1               5                   10                  15

Arg Pro Ser Phe Asp Ser Leu Ser Arg Asn Lys Leu Val Lys Lys Ile
            20                  25                  30

Leu Ser Val Phe Asn Leu Lys Gln Arg Phe Pro Gln Lys Asn Phe Gly
        35                  40                  45

Cys Pro Val Asn Ile Asn Lys Ile Arg Asp Ser Val Ile Asp Lys Ile
    50                  55                  60

Lys Asp Ser Asn Ser Gly Asn Gln Leu Phe Cys Trp Met Ser Gln Glu
65                  70                  75                  80

Arg Thr Thr Tyr Val Ser Ser Met Ile Asn Arg Ser Ile Asp Glu Met
                85                  90                  95

Ala Ile His Asn Gly Val Val Leu Thr Ser Asp Asn Lys Arg Asn Ile
            100                 105                 110

Phe Ala Ala Ile Glu Lys Lys Phe Pro Asp Ile Lys Leu Asp Glu Lys
        115                 120                 125

Ser Ala Gln Thr Ser Ile Ser His Thr Ala Leu Asn Glu Ile Ala Ser
    130                 135                 140

Ser Gly Leu Arg Ala Lys Ile Leu Lys Arg Tyr Ser Ser Asp Met Asp
145                 150                 155                 160

Leu Phe Asn Thr Gln Met Lys Asp Leu Thr Asn Leu Val Ser Ser Ser
                165                 170                 175

Val Tyr Asp Lys Ile Phe Asn Glu Ser Thr Lys Val Leu Gln Ile Glu
            180                 185                 190

Ile Ser Ala Glu Val Leu Lys Ala Val Tyr Arg Gln Ser Asn Thr Asn
        195                 200                 205


<210> SEQ ID NO 98
<211> LENGTH: 538
<212> TYPE: PRT
<213> ORGANISM: Shigella flexneri

<400> SEQUENCE: 98

Met His Ile Thr Asn Leu Gly Leu His Gln Val Ser Phe Gln Ser Gly
1               5                   10                  15

Asp Ser Tyr Lys Gly Ala Glu Glu Thr Gly Lys His Lys Gly Val Ser
            20                  25                  30

Val Ile Ser Tyr Gln Arg Val Lys Asn Gly Glu Arg Asn Lys Gly Ile
        35                  40                  45

Glu Ala Leu Asn Arg Leu Tyr Leu Gln Asn Gln Thr Ser Leu Thr Gly
    50                  55                  60

Lys Ser Leu Leu Phe Ala Arg Asp Lys Ala Glu Val Phe Cys Glu Ala
65                  70                  75                  80

Ile Lys Leu Ala Gly Gly Asp Thr Ser Lys Ile Lys Ala Met Met Glu
                85                  90                  95

Arg Leu Asp Thr Tyr Lys Leu Gly Glu Val Asn Lys Arg His Ile Asn
            100                 105                 110
```

-continued

```
Glu Leu Asn Lys Val Ile Ser Glu Glu Ile Arg Ala Gln Leu Gly Ile
        115                 120                 125

Lys Asn Lys Lys Glu Leu Gln Thr Lys Ile Lys Gln Ile Phe Thr Asp
    130                 135                 140

Tyr Leu Asn Asn Lys Asn Trp Gly Pro Val Asn Lys Asn Ile Ser His
145                 150                 155                 160

His Gly Lys Asn Tyr Ser Phe Gln Leu Thr Pro Ala Ser His Met Lys
                165                 170                 175

Ile Gly Asn Lys Asn Ile Phe Val Lys Glu Tyr Asn Gly Lys Gly Ile
            180                 185                 190

Cys Cys Ala Ser Thr Arg Glu Arg Asp His Ile Ala Asn Met Trp Leu
        195                 200                 205

Ser Lys Val Val Asp Asp Glu Gly Lys Glu Ile Phe Ser Gly Ile Arg
    210                 215                 220

His Gly Val Ile Ser Ala Tyr Gly Leu Lys Lys Asn Ser Ser Glu Arg
225                 230                 235                 240

Ala Val Ala Ala Arg Asn Lys Ala Glu Glu Leu Val Ser Ala Ala Leu
                245                 250                 255

Tyr Ser Arg Pro Glu Leu Leu Ser Gln Ala Leu Ser Gly Lys Thr Val
            260                 265                 270

Asp Leu Lys Ile Val Ser Thr Ser Leu Leu Thr Pro Thr Ser Leu Thr
        275                 280                 285

Gly Gly Glu Glu Ser Met Leu Lys Asp Gln Val Ser Ala Leu Lys Gly
    290                 295                 300

Leu Asn Ser Lys Arg Gly Gly Pro Thr Lys Leu Leu Ile Arg Asn Ser
305                 310                 315                 320

Asp Gly Leu Leu Lys Glu Val Ser Val Asn Leu Lys Val Val Thr Phe
                325                 330                 335

Asn Phe Gly Val Asn Glu Leu Ala Leu Lys Met Gly Leu Gly Trp Arg
            340                 345                 350

Asn Val Asp Lys Leu Asn Asp Glu Ser Ile Cys Ser Leu Leu Gly Asp
        355                 360                 365

Asn Phe Leu Lys Asn Gly Val Ile Gly Gly Trp Ala Ala Glu Ala Ile
    370                 375                 380

Glu Lys Asn Pro Pro Cys Lys Asn Asp Val Ile Tyr Leu Ala Asn Gln
385                 390                 395                 400

Ile Lys Glu Ile Val Asn Asn Lys Leu Gln Lys Asn Asp Asn Gly Glu
                405                 410                 415

Pro Tyr Lys Leu Ser Gln Arg Val Thr Leu Leu Ala Tyr Thr Ile Gly
            420                 425                 430

Ala Val Pro Cys Trp Asn Cys Lys Ser Gly Lys Asp Arg Thr Gly Met
        435                 440                 445

Gln Asp Ala Glu Ile Lys Arg Glu Ile Ile Arg Lys His Glu Thr Gly
    450                 455                 460

Gln Phe Ser Gln Leu Asn Ser Lys Leu Ser Ser Glu Glu Lys Arg Leu
465                 470                 475                 480

Phe Ser Thr Ile Leu Met Asn Ser Gly Asn Met Glu Ile Gln Glu Met
                485                 490                 495

Asn Thr Gly Val Pro Gly Asn Lys Val Met Lys Lys Leu Pro Leu Ser
            500                 505                 510

Ser Leu Glu Leu Ser Tyr Ser Glu Arg Ile Gly Asp Pro Lys Ile Trp
        515                 520                 525

Asn Met Val Lys Gly Tyr Ser Ser Phe Val
```

530 535

<210> SEQ ID NO 99
<211> LENGTH: 129
<212> TYPE: PRT
<213> ORGANISM: Shigella flexneri

<400> SEQUENCE: 99

Met Cys Arg Lys Leu Tyr Asp Lys Leu Tyr Glu Ile Thr Gly Ala Lys
1 5 10 15

Leu Asp Phe Asn Asp Lys Asn Gln Ala Phe Ile Leu Leu Glu Glu Gln
20 25 30

Ile Pro Val Cys Ile Thr Asp Asn Asp Glu Tyr Ile Phe Leu Thr Gly
35 40 45

Leu Leu Asn Glu His Glu Leu Phe Thr Glu Asn Ile Ile Asn Pro Glu
50 55 60

His Ile Leu Ile Leu Asn Tyr Ser Leu Ser Arg Asp Tyr Gly Ser Ser
65 70 75 80

Ile Cys Leu Leu Pro Asp Thr His Gln Cys Val Leu Thr Lys Lys His
85 90 95

Tyr Lys Lys Tyr Leu Ser Pro Asp Glu Leu Ile Glu Ser Leu Tyr Glu
100 105 110

Phe Leu Phe Cys Ile Lys Leu Thr Ile Ala Asn Ile Thr Ser Glu Val
115 120 125

Asn

<210> SEQ ID NO 100
<211> LENGTH: 494
<212> TYPE: PRT
<213> ORGANISM: Shigella flexneri

<400> SEQUENCE: 100

Met Ser Leu Lys Ile Ser Asn Phe Ile Asp Ala Ser Asn Thr Lys Gly
1 5 10 15

Pro Ile Arg Val Glu Asp Thr Glu His Gly Pro Ile Leu Ile Ala Gln
20 25 30

Lys Phe Asn Leu Lys Asp Leu Phe Phe Arg Thr Leu Ser Thr Ile Asn
35 40 45

Ala Lys Ile Asn Ser Gln Ile Leu Asn Glu Gln Leu Lys Asn Tyr Arg
50 55 60

Leu Glu Asn Gln Lys Ser Leu Leu Leu Phe Leu Asn Thr Leu Ala Ser
65 70 75 80

Glu Lys Ser Ala Glu Ser Ala Phe Ala Ala Tyr Glu Ala Ala Lys Asn
85 90 95

Ser Ile Gln His Ser Phe Thr Gly Arg Asp Ile Lys Leu Met Leu Asn
100 105 110

Thr Ala Glu Arg Phe His Gly Ile Gly Thr Ala Lys Asn Leu Glu Arg
115 120 125

His Leu Val Phe Arg Cys Trp Gly Asn Arg Gly Ile Thr His Leu Gly
130 135 140

His Thr Ser Ile Ser Ile Lys Asn Asn Leu Leu Gln Glu Pro Thr His
145 150 155 160

Thr Tyr Leu Ser Trp Tyr Pro Gly Gly Asn Val Thr Lys Asp Thr Glu
165 170 175

Ile Asn Tyr Leu Phe Glu Lys Arg Ser Gly Tyr Ser Val Asp Thr Tyr
180 185 190

Lys Gln Asp Lys Leu Asn Met Ile Ser Glu Gln Thr Ala Glu Arg Leu
195 200 205

Asp Ala Gly Gln Glu Val Arg Asn Leu Leu Asn Ser Lys Gln Asp Gln
210 215 220

Asn Asn Asn Lys Lys Ile Phe Phe Pro Arg Ala Asn Gln Lys Lys Asp
225 230 235 240

Pro Tyr Gly Tyr Trp Gly Val Ser Ala Asp Lys Val Tyr Ile Pro Leu
245 250 255

Ser Gly Asp Asn Lys Thr Lys Asp Gly Lys Ile Ser His Asn Leu Phe
260 265 270

Gly Leu Asp Glu Thr Asn Met Ser Lys Phe Ile Cys Lys Lys Lys Ala
275 280 285

Asp Ala Phe Arg Gln Leu Ala Asn Tyr Lys Leu Ile Ser Lys Ser Glu
290 295 300

Asn Cys Ala Gly Met Ala Leu Asn Val Leu Lys Ala Gly Asn Ser Glu
305 310 315 320

Ile Tyr Phe Pro Leu Pro Asp Val Lys Leu Val Ala Thr Pro Asn Asp
325 330 335

Val Tyr Ala Tyr Ala Asn Lys Val Arg Gln Arg Ile Glu Ser Leu Asn
340 345 350

Gln Ser Tyr Asn Glu Ile Met Lys Tyr Ile Glu Ser Asp Phe Asp Leu
355 360 365

Ser Arg Leu Thr Gln Leu Arg Arg Ser Tyr Leu Lys Ser Phe Asn Lys
370 375 380

Ile Asn Leu Ile His Thr Pro Lys Thr Phe Lys Pro Leu Ser Ile Ser
385 390 395 400

Leu Tyr Lys His Pro Thr Glu Asn Val Ser Ser Glu Asp Phe Asp Ala
405 410 415

Val Ile Asn Ala Cys His Ser Tyr Leu Val Lys Ser Ala Pro Ser Asn
420 425 430

Met Thr Arg Val Leu Asn Glu Leu Lys Thr Glu Ala Thr Asp Lys Lys
435 440 445

Glu Glu Ile Ile Glu Lys Ser Ile Lys Ile Ile Asp Tyr Tyr Asn Ser
450 455 460

Leu Lys Ser Pro Asp Leu Gly Thr Lys Leu Tyr Ile His Asp Leu Leu
465 470 475 480

Gln Ile Asn Lys Leu Leu Leu Asn Asn Ser His Ser Asn Ile
485 490

<210> SEQ ID NO 101
<211> LENGTH: 561
<212> TYPE: PRT
<213> ORGANISM: Salmonella enterica

<400> SEQUENCE: 101

Met Gln Ile Gln Ser Phe Tyr His Ser Ala Ser Leu Lys Thr Gln Glu
1 5 10 15

Ala Phe Lys Ser Leu Gln Lys Thr Leu Tyr Asn Gly Met Gln Ile Leu
20 25 30

Ser Gly Gln Gly Lys Ala Pro Ala Lys Ala Pro Asp Ala Arg Pro Glu
35 40 45

Ile Ile Val Leu Arg Glu Pro Gly Ala Thr Trp Gly Asn Tyr Leu Gln
50 55 60

His Gln Lys Ala Ser Asn His Ser Leu His Asn Leu Tyr Asn Leu Gln

-continued

```
65                  70                  75                  80

Arg Asp Leu Leu Thr Val Ala Ala Thr Val Leu Gly Lys Gln Asp Pro
                85                  90                  95

Val Leu Thr Ser Met Ala Asn Gln Met Glu Leu Ala Lys Val Lys Ala
            100                 105                 110

Asp Arg Pro Ala Thr Lys Gln Glu Glu Ala Ala Ala Lys Ala Leu Lys
        115                 120                 125

Lys Asn Leu Ile Glu Leu Ile Ala Ala Arg Thr Gln Gln Gln Asp Gly
    130                 135                 140

Leu Pro Ala Lys Glu Ala His Arg Phe Ala Ala Val Ala Phe Arg Asp
145                 150                 155                 160

Ala Gln Val Lys Gln Leu Asn Asn Gln Pro Trp Gln Thr Ile Lys Asn
                165                 170                 175

Thr Leu Thr His Asn Gly His His Tyr Thr Asn Thr Gln Leu Pro Ala
            180                 185                 190

Ala Glu Met Lys Ile Gly Ala Lys Asp Ile Phe Pro Ser Ala Tyr Glu
        195                 200                 205

Gly Lys Gly Val Cys Ser Trp Asp Thr Lys Asn Ile His His Ala Asn
    210                 215                 220

Asn Leu Trp Met Ser Thr Val Ser Val His Glu Asp Gly Lys Asp Lys
225                 230                 235                 240

Thr Leu Phe Cys Gly Ile Arg His Gly Val Leu Ser Pro Tyr His Glu
                245                 250                 255

Lys Asp Pro Leu Leu Arg His Val Gly Ala Glu Asn Lys Ala Lys Glu
            260                 265                 270

Val Leu Thr Ala Ala Leu Phe Ser Lys Pro Glu Leu Leu Asn Lys Ala
        275                 280                 285

Leu Ala Gly Glu Ala Val Ser Leu Lys Leu Val Ser Val Gly Leu Leu
    290                 295                 300

Thr Ala Ser Asn Ile Phe Gly Lys Glu Gly Thr Met Val Glu Asp Gln
305                 310                 315                 320

Met Arg Ala Trp Gln Ser Leu Thr Gln Pro Gly Lys Met Ile His Leu
                325                 330                 335

Lys Ile Arg Asn Lys Asp Gly Asp Leu Gln Thr Val Lys Ile Lys Pro
            340                 345                 350

Asp Val Ala Ala Phe Asn Val Gly Val Asn Glu Leu Ala Leu Lys Leu
        355                 360                 365

Gly Phe Gly Leu Lys Ala Ser Asp Ser Tyr Asn Ala Glu Ala Leu His
    370                 375                 380

Gln Leu Leu Gly Asn Asp Leu Arg Pro Glu Ala Arg Pro Gly Gly Trp
385                 390                 395                 400

Val Gly Glu Trp Leu Ala Gln Tyr Pro Asp Asn Tyr Glu Val Val Asn
                405                 410                 415

Thr Leu Ala Arg Gln Ile Lys Asp Ile Trp Lys Asn Asn Gln His His
            420                 425                 430

Lys Asp Gly Gly Glu Pro Tyr Lys Leu Ala Gln Arg Leu Ala Met Leu
        435                 440                 445

Ala His Glu Ile Asp Ala Val Pro Ala Trp Asn Cys Lys Ser Gly Lys
    450                 455                 460

Asp Arg Thr Gly Met Met Asp Ser Glu Ile Lys Arg Glu Ile Ile Ser
465                 470                 475                 480

Leu His Gln Thr His Met Leu Ser Ala Pro Gly Ser Leu Pro Asp Ser
                485                 490                 495
```

Gly Gly Gln Lys Ile Phe Gln Lys Val Leu Leu Asn Ser Gly Asn Leu
500 505 510

Glu Ile Gln Lys Gln Asn Thr Gly Gly Ala Gly Asn Lys Val Met Lys
515 520 525

Asn Leu Ser Pro Glu Val Leu Asn Leu Ser Tyr Gln Lys Arg Val Gly
530 535 540

Asp Glu Asn Ile Trp Gln Ser Val Lys Gly Ile Ser Ser Leu Ile Thr
545 550 555 560

Ser

<210> SEQ ID NO 102
<211> LENGTH: 685
<212> TYPE: PRT
<213> ORGANISM: Salmonella enterica

<400> SEQUENCE: 102

Met Val Thr Ser Val Arg Thr Gln Pro Pro Val Ile Met Pro Gly Met
1 5 10 15

Gln Thr Glu Ile Lys Thr Gln Ala Thr Asn Leu Ala Ala Asn Leu Ser
20 25 30

Ala Val Arg Glu Ser Ala Thr Ala Thr Leu Ser Gly Glu Ile Lys Gly
35 40 45

Pro Gln Leu Glu Asp Phe Pro Ala Leu Ile Lys Gln Ala Ser Leu Asp
50 55 60

Ala Leu Phe Lys Cys Gly Lys Asp Ala Glu Ala Leu Lys Glu Val Phe
65 70 75 80

Thr Asn Ser Asn Asn Val Ala Gly Lys Lys Ala Ile Met Glu Phe Ala
85 90 95

Gly Leu Phe Arg Ser Ala Leu Asn Ala Thr Ser Asp Ser Pro Glu Ala
100 105 110

Lys Thr Leu Leu Met Lys Val Gly Ala Glu Tyr Thr Ala Gln Ile Ile
115 120 125

Lys Asp Gly Leu Lys Glu Lys Ser Ala Phe Gly Pro Trp Leu Pro Glu
130 135 140

Thr Lys Lys Ala Glu Ala Lys Leu Glu Asn Leu Glu Lys Gln Leu Leu
145 150 155 160

Asp Ile Ile Lys Asn Asn Thr Gly Gly Glu Leu Ser Lys Leu Ser Thr
165 170 175

Asn Leu Val Met Gln Glu Val Met Pro Tyr Ile Ala Ser Cys Ile Glu
180 185 190

His Asn Phe Gly Cys Thr Leu Asp Pro Leu Thr Arg Ser Asn Leu Thr
195 200 205

His Leu Val Asp Lys Ala Ala Ala Lys Ala Val Glu Ala Leu Asp Met
210 215 220

Cys His Gln Lys Leu Thr Gln Glu Gln Gly Thr Ser Val Gly Arg Glu
225 230 235 240

Ala Arg His Leu Glu Met Gln Thr Leu Ile Pro Leu Leu Leu Arg Asn
245 250 255

Val Phe Ala Gln Ile Pro Ala Asp Lys Leu Pro Asp Pro Lys Ile Pro
260 265 270

Glu Pro Ala Ala Gly Pro Val Pro Asp Gly Gly Lys Lys Ala Glu Pro
275 280 285

Thr Gly Ile Asn Ile Asn Ile Asn Ile Asp Ser Ser Asn His Ser Val
290 295 300

-continued

```
Asp Asn Ser Lys His Ile Asn Asn Ser Arg Ser His Val Asp Asn Ser
305                 310                 315                 320

Gln Arg His Ile Asp Asn Ser Asn His Asp Asn Ser Arg Lys Thr Ile
                325                 330                 335

Asp Asn Ser Arg Thr Phe Ile Asp Asn Ser Gln Arg Asn Gly Glu Ser
            340                 345                 350

His His Ser Thr Asn Ser Ser Asn Val Ser His Ser His Ser Arg Val
        355                 360                 365

Asp Ser Thr Thr His Gln Thr Glu Thr Ala His Ser Ala Ser Thr Gly
    370                 375                 380

Ala Ile Asp His Gly Ile Ala Gly Lys Ile Asp Val Thr Ala His Ala
385                 390                 395                 400

Thr Ala Glu Ala Val Thr Asn Ala Ser Ser Glu Ser Lys Asp Gly Lys
                405                 410                 415

Val Val Thr Ser Glu Lys Gly Thr Thr Gly Glu Thr Thr Ser Phe Asp
            420                 425                 430

Glu Val Asp Gly Val Thr Ser Lys Ser Ile Ile Gly Lys Pro Val Gln
        435                 440                 445

Ala Thr Val His Gly Val Asp Asp Asn Lys Gln Gln Ser Gln Thr Ala
    450                 455                 460

Glu Ile Val Asn Val Lys Pro Leu Ala Ser Gln Leu Ala Gly Val Glu
465                 470                 475                 480

Asn Val Lys Thr Asp Thr Leu Gln Ser Asp Thr Thr Val Ile Thr Gly
                485                 490                 495

Asn Lys Ala Gly Thr Thr Asp Asn Asp Asn Ser Gln Thr Asp Lys Thr
            500                 505                 510

Gly Pro Phe Ser Gly Leu Lys Phe Lys Gln Asn Ser Phe Leu Ser Thr
        515                 520                 525

Val Pro Ser Val Thr Asn Met His Ser Met His Phe Asp Ala Arg Glu
    530                 535                 540

Thr Phe Leu Gly Val Ile Arg Lys Ala Leu Glu Pro Asp Thr Ser Thr
545                 550                 555                 560

Pro Phe Pro Val Arg Arg Ala Phe Asp Gly Leu Arg Ala Glu Ile Leu
                565                 570                 575

Pro Asn Asp Thr Ile Lys Ser Ala Ala Leu Lys Ala Gln Cys Ser Asp
            580                 585                 590

Ile Asp Lys His Pro Glu Leu Lys Ala Lys Met Glu Thr Leu Lys Glu
        595                 600                 605

Val Ile Thr His His Pro Gln Lys Glu Lys Leu Ala Glu Ile Ala Leu
    610                 615                 620

Gln Phe Ala Arg Glu Ala Gly Leu Thr Arg Leu Lys Gly Glu Thr Asp
625                 630                 635                 640

Tyr Val Leu Ser Asn Val Leu Asp Gly Leu Ile Gly Asp Gly Ser Trp
                645                 650                 655

Arg Ala Gly Pro Ala Tyr Glu Ser Tyr Leu Asn Lys Pro Gly Val Asp
            660                 665                 670

Arg Val Ile Thr Thr Val Asp Gly Leu His Met Gln Arg
        675                 680                 685
```